United States Patent [19]
Jakobi et al.

[11] Patent Number: 6,107,299
[45] Date of Patent: Aug. 22, 2000

[54] SUBSTITUTED PYRIDINE AND PYRIMIDINE, PROCESSES FOR THEIR PREPARATION AND THEIR USE AS PESTICIDES

[75] Inventors: Harald Jakobi, Frankfurt; Matthias Eckhardt, Wetzlar; Wolfgang Schaper, Diedorf; Ralf Braun, Büttelborn; Gerhard Krautstrunk, Bad Vilbel; Oswald Ort, Glashütten; Ulrich Sanft, Eppstein/Ts.; Maria-Theresia Thönessen, Heidesheim; Werner Bonin, Kelkheim, all of Germany

[73] Assignee: Hoechst Schering AgrEvo GmbH, Berlin, Germany

[21] Appl. No.: 09/313,410

[22] Filed: May 18, 1999

[30] Foreign Application Priority Data

May 20, 1998 [GB] United Kingdom .................. 9810862

[51] Int. Cl.⁷ ...................... A01N 43/54; C07D 239/00; C07D 239/02; C07D 471/02; C07D 211/78
[52] U.S. Cl. ...................... 514/256; 544/255; 544/319; 544/326; 544/243; 546/114; 546/286; 546/289; 546/290; 546/301; 546/304; 514/269; 514/86; 514/89; 514/258; 514/345; 514/352
[58] Field of Search ...................... 514/256, 258, 514/269, 345, 352, 86, 89; 544/255, 319, 326, 243; 546/114, 286, 289, 22, 290, 301, 304, 312

[56] References Cited

U.S. PATENT DOCUMENTS 5,723,450 3/1998 Reuschling et al.
5,852,023 12/1998 Schaper et al.
5,925,644 7/1999 Jakobi et al. .................. 514/269

OTHER PUBLICATIONS

U.S. application No. 08/549,088 which relates to DE 4438807 identified as AGR 94/M 222, filed Oct. 27, 1995.
U.S. application No. 08/970,163 which relates to DE 19647402 identified as AGR 96/M 219, filed Nov. 13, 1997.
U.S. application No. 08/970,164 which relates to DE 19647413 identified as AGR 1996/M 220, filed Nov. 13, 1997.

*Primary Examiner*—Joseph McKane
*Assistant Examiner*—Joseph Murray
*Attorney, Agent, or Firm*—Frommer Lawrence & Haug LLP

[57] ABSTRACT

Compounds of formula I, N-oxides or salts, thereof

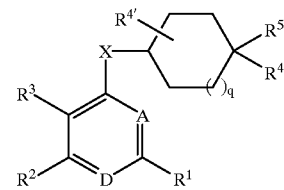

(I)

in which
q is 0, 1 or 2
A is CH and D is $N^+R \times 1/n \; Q^{n-}$ or A is N and D is $N^+R \times 1/n \; Q^{n-}$ or A is CH or N and D is N
or A is $N^+R \times 1/n \; Q^{n-}$ and D is N, R is $CR^6R^7D^aR^8$,
$Q^{n-}$ is an inorganic or organic anion, n being 1, 2, 3 or 4;
X is NH, O or $S(O)_q$, (q is 0, 1 or 2); and the R groups have various meanings as defined in the claims are useful pesticidal, especially insecticidal activity.

3 Claims, No Drawings

SUBSTITUTED PYRIDINE AND PYRIMIDINE, PROCESSES FOR THEIR PREPARATION AND THEIR USE AS PESTICIDES

Substituted pyridine and pyrimidines, processes for their preparation and their use as pesticides The invention relates to novel substituted pyridines and pyrimidines and condensed systems derived therefrom, processes for their preparation and their use as pesticides, especially insecticides and acaricides.

It is already known that certain 4-cycloalkylamino- and -alkoxy-heterocycles have fungicidal, acaricidal and insecticidal activity (for example DE 42 08 254)

However, the biological activity of these compounds, in particular at low application rates and concentrations, is not satisfactory in all use examples.

It has now been found that compounds of formula I have been found

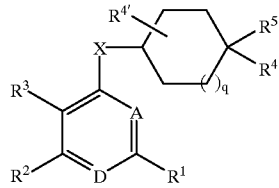

(I)

in which the radicals and groups are as defined below, which, while showing good tolerance by plants and favourable toxicity in respect of warm-blooded animals, are highly suitable as pesticides and especially for controlling insects and acarids. Some compounds also show fungicidal activity.

The invention therefore relates to compounds of the formula I, their N-oxides and salts in which q is 0, 1 or 2

$R^1$ is hydrogen, halogen, $(C_1-C_8)$-alkyl, $(C_1-C_8)$-haloalkyl, $(C_1-C_8)$-alkoxy or $(C_3-C_6)$-cycloalkyl;

$R^2$ and $R^3$ are identical or different and are each hydrogen, $(C_1-C_8)$-alkyl, $(C_2-C_8)$-alkenyl, $(C_2-C_8)$-alkynyl, $(C_1-C_8)$-alkoxy, halogen, hydroxy, cyano, nitro, thiocyanato, $(C_1-C_8)$-alkoxycarbonyl, $(C_1-C_8)$-alkylthio, $(C_1-C_8)$-alkylsulfinyl, $(C_1-C_8)$-alkylsulfonyl, amino; $(C_1-C_8)$-alkylamino, $(C_1-C_8)$-dialkylamino or $(C_3-C_6)$-cycloalkyl, and in which in the alkyl, cycloalkyl, alkenyl, alkynyl groups or the groups derived from them, such as alkoxy, alkynyl, alkanoyl, alkoxycarbonyl, alkylthio, alkylsulfinyl, alkylsulfonyl, alkylamino or dialkylamino, a saturated carbon unit can be replaced by a hetero atom unit such as oxygen, $S(O)_x$, where x=0, 1 or 2 or by dimethylsilyl and further in these groups or derived groups up to 3 hydrogen atoms can be replaced by halogen and in the case of fluorine also all hydrogen atoms can be replaced by fluorine; or $R^2$ and $R^3$ together with the carbon atoms to which they are attached form an unsaturated 5- or 6-membered carbocyclic ring which may, if it is a 5-membered ring, contain an oxygen or sulfur atom instead of $CH_2$, or which may, if it is a 6-membered ring, contain one or two nitrogen atoms instead of one or two CH units, and which may be substituted by 1, 2 or 3 identical or different radicals, these radicals being $(C_1-C_4)$-alkyl, $(C_1-C_4)$-haloalkyl, preferably trifluoromethyl, halogen, $(C_1-C_4)$-alkoxy or $(C_1-C_4)$-haloalkoxy; or $R^2$ and $R^3$ together with the carbon atoms to which they are attached form a saturated 5-, 6- or 7-membered carbocyclic ring which may contain oxygen and/or sulfur instead of one or two $CH_2$ groups and which may be substituted by 1, 2 or 3 $(C_1-C_4)$-alkyl groups;

A is CH and D is $N^+R \times 1/n\ Q^{n-}$ or
A is N and D is $N^+R \times 1/n\ Q^{n-}$ or
A is CH or N and D is N or
A is $N^+R \times 1/n\ Q^{n-}$ and D is N,
R is $CR^6R^7D^aR^8$,
$Q^{n-}$ an inorganic or organic anion, n being 1, 2, 3 or 4;
X is NH, O or $S(O)_q$, (q is 0, 1 or 2);
$R^4$ and $R^{4'}$, which may be the same or different, are hydrogen, halogen, $(C_1-C_4)$-alkyl, $(C_1-C_4)$-halogenalkyl, $(C_1-C_4)$-alkoxy or $(C_1-C_4)$-alkylthio;
$R^5$ is the group

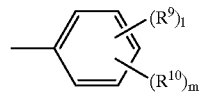

l is 1, 2, 3, 4 or 5;
m is 0, 1, 2, 3 or 4,
each $R^9$, which may be the same or different from any other $R^9$, is $(C_2-C_8)$-haloalkenyloxy, $(C_2-C_8)$-haloalkynyl, $(C_2-C_8)$-haloalkynyloxy, $(C_1-C_4)$-haloalkoxy-$(C_1-C_4)$-haloalkoxy, oxiran-2-ylmethoxy, oxetan-2-ylmethoxy, isopropylidenoamino-oxy, isopropylidenamino-oxy-$(C_1-C_4)$-alkoxy, formyl, $—SF_5$, hydroxy or heterocyclyloxy, in which the last named group may be substituted by up to three (in the case of fluorine up to the maximum number), of the same or different $D^1R^{12}$, cyano, nitro or halogen, or
$R^9$ is a group $Z—R^{11}$, in which
Z is $OSO_2$, $NR^{13}SO_2$, $UC(=W)V$, $U^1P(W^1)(V^1R^{11})V^2$, $SO_2NR^{13}$, $SO_2O$, $NR^{13}SO_2NR^{13}$, $OSO_2NR^{13}$, $NR^{13}SO_2O$, $Si(OR)^{13}R^{13}$, $N(O)R^{13}$, $NR^{13}O$, $NR^{13}NR^{13}$, $N=N$, $N=$, $NR^{13}—N=$, $D^1—N=$ and
$U^1$ is a direct bond, oxygen, $NR^{13}$ or sulfur,
U is oxygen, $NR^{13}$ or sulfur, or when W or V is $NR^{13}$ or sulfur, it can also be a direct bond,
W is oxygen, $NR^{130}$ or sulfur, preferably oxygen, and
$R^{130}$ is hydrogen, nitro, cyano, optionally substituted alkyl, optionally substituted acyloxy, optionally substituted aryl, optionally substituted heteroaryl, hydroxy, optionally substituted alkoxy, optionally substituted aryloxy, optionally substituted heteroaryloxy, mono- or disubstituiertes amino;
$W^1$ is oxygen or sulfur,
V, $V^1$, $V^2$, independently of each other are a direct bond, $NR^{13}$, oxygen or sulfur,
each $R^{13}$, which may be the same or different from any other $R^{13}$, is hydroxy, alkyl, optionally substituted alkoxy, optionally substituted aryloxy, optionally substituted aryl, optionally substituted heteroaryl, optionally substituted heteroaryloxy, mono- or disubstituiertes amino, optionally substituted acyl or optionally substituted acyloxy,
$R^{11}$ is $(C_1-C_{20})$-alkyl, $(C_2-C_{20})$-alkenyl, $(C_2-C_{20})$-alkynyl, $(C_3-C_8)$-cycloalky or $(C_4-C_8)$-cycloalkenyl, in which groups optionally one or more, generally up to three, $CH_2$-groups can be replaced by carbonyl-, thiocarbonyl or heteroatom units, preferably O, S, SO, $SO_2$, $NR^{13}$ or $SiR^{16}R^{17}$, and these groups may be substituted by up to three (in the case of fluorine up to the maximum number), of the same or different $D^2R^{14}$, cyano, nitro or halogen, or $R^{11}$ is hydrogen, aryl or heterocyclyl, in which the last named group may be substituted by up to three (in the case of fluorine up to the maximum number), of the same or different $D^3R^{15}$, cyano, nitro or halogen, or when V is $NR^{13}$, $R^{13}$ and $R^{11}$ can together form a 4- to 8-membered ring, in which one or two $CH_2$-groups, preferably one $CH_2$-group is replaced by a hetero atom unit, preferably oxygen, $S(O)_n$, (where=0, 1 or 2), or $NR^{19}$, in which $D^1$, $D^2$ and $D^3$, independently of each other, are a direct bond, oxygen, $S(O)_k$, $SO_2O$, $OSO_2$, CO, OCO, COO, $NR^{13'}$, $SO_2$—$NR^{13'}$, $NR^{13'}SO_2$, $ONR^{13'}$, $NR^{13'}O$, $NR^{13'}CO$, $CONR^{13'}$ or $SiR^{16}R^{17}$, and k=0, 1 or 2 and $R^{13'}$ has the same meaning as $R^{13}$, $R^{16}$, $R^{17}$, independently of each other, are $(C_1-C_4)$-alkyl;

$R^{12}$, $R^{14}$ and $R^{15}$ are hydrogen, $C_1-C_8$-alkyl, $C_2-C_8$-alkenyl, $C_2-C_8$-alkynyl, $C_3-C_8$-cycloalkyl, $C_4-C_8$-cycloalkenyl, $C_3-C_8$-cycloalkyl-$C_1-C_4$-alkyl, $C_4-C_8$-cycloalkenyl-$C_1-C_4$-alkyl, aryl, heterocyclyl, aryl-$C_1-C_4$-alkyl or heterocyclyl-$C_1-C_4$-alkyl bedeutet, in which in any alkyl-, alkenyl- and alkynyl based groups optionally one or more, preferably up to three, $CH_2$-group can be replaced by hetero atom units O or S, the alkyl, alkenyl- and alkynyl groups, with or without the named variations, can also be optionally substituted by one or more, preferably up to three, (in the case of halogen up to the maximum number), of the same or different groups selected from halogen, hydroxy and cyano and in the case of of the last named 8 groups, the cycloaliphatic, aromatic or heterocyclic rings are unsubstituted or substituted by one or more, preferably up to three, (in the case of halogen up to the maximum number), of the same or different substituents $R^{18}$;

$R^{18}$ is $(C_1-C_4)$-alkyl, $(C_1-C_4)$-haloalkyl, $(C_1-C_4)$-alkoxy, $(C_1-C_4)$-haloalkoxy, cyano, nitro or halogen;

$R^{19}$ is hydrogen, $(C_1-C_8)$-alkyl, $(C_1-C_4)$-haloalkyl, $(C_1-C_4)$-alkoxy, $(C_1-C_4)$-alkythio, $(C_3-C_5)$-cycloalkyl, $(C_2-C_4)$-alkenyl, $(C_2-C_4)$-alkynyl, $(C_1-C_4)$-alkanoyl, $(C_2-C_4)$-haloalkanoyl, $(C_2-C_4)$-alkoxyalkyl, phenyl-$(C_1-C_4)$-alkyl or phenyl and the phenyl groups are unsubstituted or substituted by one or more, preferably up to three, (in the case of fluorine up to the maximum number), of the same or different substituents $R^{20}$, $R^{20}$ is $(C_1-C_4)$-alkyl, $(C_1-C_4)$-haloalkyl, $(C_1-C_4)$-alkoxy, $(C_1-C_4)$-alkylthio, halogen or cyano;

$R^{10}$ is cyano, nitro, halogen, $C_1-C_8$-alkyl, $C_2-C_8$-alkenyl, $C_2-C_8$-alkynyl, $C_3-C_8$-cycloalkyl, $C_4-C_8$-cycloalkenyl, $C_3-C_8$-cycloalkyl-$C_1-C_4$-alkyl, $C_4-C_8$-cycloalkenyl-$C_1-C_4$-alkyl, aryl, heterocyclyl, aryl-$C_1-C_4$-alkyl or heterocyclyl-$C_1-C_4$-alkyl in which in any alkyl-, alkenyl- and alkynyl based groups optionally one or more, preferably up to three, $CH_2$-group can be replaced by hetero atom units O or S, the alkyl, alkenyl- and alkynyl groups, with or without the named varations, can also be optionally substituted by one or more, preferably up to three, (in the case of halogen up to the maximum number), of the same or different groups selected from halogen, hydroxy and cyano and in the case of of the last named 8 groups, the cycloaliphatic, aromatic or heterocyclic rings are unsubstituted or substituted by one or more, preferably up to three, (in the case of halogen up to the maximum number), of the same or different substituents $R^{21}$, $R^{21}$ has the same meaning as $R^{18}$, or two adjacent $R^9$ and/or $R^{10}$ groups together with the carbon atoms two which they are attached can form an unsaturated 5- or 6-membered carbocyclic ring, which in a 5 membered ring, a $CH_2$ can be replaced by an oxygen- or sulfur atom and in a 6 membered ring, one or two CH units can be replaced by one or two nitrogen atoms or substituted by 1, 2 or 3 of the same or different groups selected from $(C_1-C_4)$-alkyl, $(C_1-C_4)$-haloalkyl, (preferably trifluormethyl), halogen, $(C_1-C_4)$-alkoxy or $(C_1-C_4)$-haloalkoxy; or two adjacent $R^9$ and/or $R^{10}$ groups together with the carbon atoms to which they are attached can form a saturated 5- or 6- or 7 membered carbocyclic ring, in which, one or two $CH_2$ units can be replaced by one or two oxygen and/or sulfur and can be substituted by 1, 2 or 3 $(C_1-C_4)$-alkyl groups, and further when A is CH and D is $N^+R \times 1/n\ Q^{n-}$ or A is N and D is $N^+R \times 1/n\ Q$ or A is $N^+R \times 1/n\ Q^{n-}$ and D is N $R^9$ can also be $(C_2-C_6)$-alkynyl, $(C_2-C_6)$-alkynyloxy or $(C_2-C_6)$-haloalkenyl;

$R^6$ is hydrogen, halogen or $C_1-C_4$-alkyl or a negative charge, which can represent $Q^{n-}$ $R^7$ is hydrogen, halogen, CN, nitro, $(C_1-C_4)$-alkoxycarbonyl, $(C_1-C_4)$-alkylcarbamoyl, di-$(C_1-C_4)$-alkylcarbamoyl, $(C_1-C_8)$-alkoxy, $(C_1-C_8)$-alkyl, $(C_2-C_8)$-alkenyl, $(C_2-C_8)$-alkynyl, aryl or $(C_3-C_8)$-cycloalkyl.

$D^a$ is a direct bond, $NR^{70}$, $N(O)R^{70}$, O, S, SO, $SO_2$, $C(=W^a)$, $OC(=W^a)$, $U^a(C=W^a)V^a$ ($U^a$ and $V^a$ are a direct bond, $NR^{70}$, S or O, except $V^a$ is not a bond when $U^a$ is bond or O), $SiR^{72}R^{73}$, $U^b(P=W^b)V^bV^c$, $U^b(SO_2)U^c$ (one of $U^b$ and $U^c$ is a direct bond, $NR^{70}$, S or O and the other is $NR^{70}$), $U^a(CW^a)(CW^a)V^b$, $NR^{70}O$, O $NR^{70}$, $NR^{70}$ $NR^{70}$, N=N, —N=, —$NR^{70}$—N= —O—N=, and $W^a$ is O, S or $NR^{71}$;

$W^b$ is O or S;

$U^a$, $V^b$ and $V^c$, independently of each other are a direct bond, $NR^{70}$, S or O each $R^{70}$, which may be the same or different from any other $R^{70}$, is hydrogen, hydroxy, optionally substituted alkyl, optionally substituted alkoxy, optionally substituted aryloxy, optionally substituted aryl, optionally substituted heteroaryl, optionally substituted heteroaryloxy, mono- or disubstituted amino, optionally substituted acyloxy, and may also form a 4 to 8 membered with $R^6$, $R^{112}$ OR $R^{113}$, respectively with the $D^a$, $D^{12}$ OR. $D^{13}$ to which they are attached.

each $R^{71}$, which may be the same or different from any other $R^{71}$, is hydrogen, nitro, cyano, hydroxy, optionally substituted alkyl, optionally substituted alkoxy, optionally substituted aryloxy, optionally substituted aryl, optionally substituted heteroaryl, optionally substituted heteroaryloxy, mono- or disubstituted amino or optionally substituted acyloxy;

$R^{72}$ and $R^{73}$ are alkyl or optionally substituted aryl; and $R^8$ is hydrogen, cyano, alkyl, alkenyl, alkynyl, cycloalkyl, cycloalkenyl, aryl or heterocyclyl, in which up to three $CH_2$ units in a carbon containing group can be replaced by carbonyl-, thiocarbonyl or O, S, SO, $SO_2$, $NR^{70}$ or Si $R^{72}R^{73}$ and can also be substituted by nitro, halogen, $SF_5$ or $D^{12}R^{112}$, and in the case $D^a$ is $U^bP(=W^b)V^bV^c$, the two $R^6$ groups together with the $V^bPV^c$, to which they are attached can form a 4 to 8 membered ring, $D^{12}$ is a direct bond, $NR^{70}$, $N(O)R^{70}$, O, S, SO, $SiR^{72}R^{73}$, U'(CW')V', $U^{1'}(PW^{1'})V^{1'}V^{2'}$, $U^{2'}(SO_2)U^{3'}$, $Si(OR^{72})R^{73}$, $Si(OR^{72})(OR^{73})$, $NR^{70}O$, $ONR^{70}$, $NR^{70}NR^{70}$, N=N, =N—, =N—NR70— =N—O—, —N=, —$NR^{70}$—N= or —O—N= and U', $U^{1'}$, V', $V^{1'}$ and $V^{2'}$, independently of each other are a direct bond, $NR^{70}$, S or O W' is O, S or $NR^{71}$;

W$^{1'}$ is or S;

$U^{2'}$ and $U^{3'}$, independently of each other are a direct bond, $NR^{70}$ or O;

$R^{112}$ is hydrogen, cyano, alkyl, alkenyl, alkynyl, cycloalkyl, cycloalkenyl, aryl or heterocyclyl, in which up to CH$_2$ units in a carbon containing group can be replaced by carbonyl-, thiocarbonyl or O, S, SO, SO$_2$, $NR^{70}$ or $SiR^{72}R^{73}$ and can also be substituted by nitro, halogen, SF$_5$ or $D^{13}R^{113}$ and in which two adjacent $D^{12}R^{112}$ together with the carbons to which they are attached can form a condensed ring comprising 4 to 6 ring atoms which can be substituted one or more halogen or $C_1$–$C_4$-alkyl; is a negative charge for $D^{12}$= (CO)O, (SO$_2$)O, $U^{1'}(PW^{1'})V^{1'}$O which replaces the ion $Q^{n-}$; or $R^{112}$ is hydrogen when $D^{12}$ is O(CO)NH, $NR^{70}$(CO)NH, O(CS)NH, $NR^{70}$(CS)NH, (CO)NH, (CS)NH, O(CO), $NR^{70}$(CO), SO2NH;

$D^{13}$ has the same meaning as $D^{12}$ and $R^{113}$ has the same meaning as $R^{112}$.

Aryl is usually a naphthyl or phenyl group, optionally substituted by one or more, preferably up to five, in particular up to three, identical or different radicals selected from the group consisting of halogen, ($C_3$–$C_8$)-cycloalkyl, ($C_3$–$C_8$)-cycloalkenyl, phenoxy, substituted phenoxy, phenylthio, substituted phenylthio, phenyl, substituted phenyl, optionally substituted heterocyclyl, optionally substituted heterocyclyloxy, optionally substituted heterocyclylthio

NO$_2$,

—C(O)—$R^{133}$, acetoxy, hydroxyl, cyano, $SiR^{144}R^{155}R^{166}$,

O—$SiR^{144}R^{155}R^{166}$, $NR^{177}R^{188}$

S(O)$R^{199}$,

SO$_2R^{199}$, ($C_1$–$C_{12}$)-alkyl, ($C_2$–$C_{12}$)-alkenyl, ($C_1$–$C_{12}$)-alkoxy and ($C_1$–$C_{12}$)-alkylthio; and $R^{133}$ is ($C_1$–$C_7$)-alkyl, halo-($C_1$–$C_7$)-alkyl, ($C_3$–$C_7$)-cycloalkyl, halo-(C–$C_7$)-cycloalkyl, ($C_1$–$C_7$)-alkoxy, phenyl or substituted phenyl;

$R^{144}$, $R^{155}$ and $R^{166}$ are identical or different and are each independently of one another ($C_1$–$C_4$)-alkyl, phenyl and/or substituted phenyl;

$R^{177}$ and $R^{188}$ are identical or different and are each independently of the other hydrogen, ($C_1$–$C_4$)-alkyl and/or ($C_1$–$C_4$)-acyl;

$R^{199}$ is ($C_1$–$C_{10}$)-alkyl, phenyl or substituted phenyl; wherein in ($C_1$–$C_{12}$)-alkyl, ($C_1$–$C_{12}$)-alkoxy, ($C_1$–$C_{12}$)-alkylthio and ($C_2$–$C_{12}$)-alkenyl one or more, preferably up to 3, CH$_2$ groups may be replaced by hetero atom radicals such as O, S, SO, SO$_2$, $NR^{10'}$ or $SiR^{11'}R^{12'}$; $R^{10'}$, $R^{11'}$ and $R^{12'}$ have the meanings of $R^{10}$, $R^{11}$, $R^{12}$;

the ($C_1$–$C_{12}$)-alkyl radical with or without the abovementioned variations may also be substituted by one or more, preferably up to three (in the case of halogen up to the maximum number), identical or different radicals selected from the group below consisting of halogen, halo-($C_1$–$C_4$)-alkoxy, hydroxyl, ($C_3$–$C_8$)-cycloalkyl, ($C_3$–$C_8$)-cycloalkenyl, ($C_1$–$C_4$)-acyl, phenoxy, substituted phenoxy, phenyl, substituted phenyl, phenylthio and substituted phenylthio; in the ($C_1$–$C_7$)-alkoxy and ($C_1$–$C_7$)-alkylthio radicals, one or more, preferably up to three, CH$_2$ groups may be replaced by O, and these radicals may be substituted by one or more, preferably up to three (in the case of halogen up to the maximum number), identical or different radicals selected from the group consisting of halogen, phenyl, substituted phenyl, ($C_3$–$C_8$)-cycloalkyl, ($C_3$–$C_8$)-cycloalkenyl, phenoxy and substituted phenoxy; or, if not included in the above definitions the definitions the carbon containing groups defined under $R^6$, $R^7$ or $R^8$, it can be substituted by one or more, preferably up to three (in the case of halogen up to the maximim number of the same or different groups selected from halogen, cycloalkyl, phenoxy, substituted phenoxy, phenyl or substituted phenyl.

An inorganic anion is an anion of an inorganic acid, for example F—, Cl—, Br—, I—, NO$_3$—, SO$_4^{2-}$—, HSO$_4$—, PO$_4^{3-}$—, HPO$_4^{2-}$—, H$_2$PO$_4$—, PO$_3^{3-}$— or N$_3$—, or a complex anion, for example BF$_4$—, PF$_6$— or tetraphenylborate.

An organic anion is an anion of an organic acid (carboxylic acid, sulfonic acid, phosphonic acid and the like) or an aromatic or heteroaromatic phenol-like compound. These are, for example, anions of mono- or bifunctional carboxylic acids and hydroxycarboxylic acids such as acetic acid, propionic acid, maleic acid, succinic acid, glycolic acid, oxalic acid, fumaric acid, tartaric acid, citric acid, salicylic acid, sorbic acid or lactic acid, and sulfonic acids such as p-toluenesulfonic acid, dodecylsulfonic acid or 1,5-naphthalenedisulfonic acid, or saccharine.

If A and D are part of a pyrimidine system, it is assumed that A is nitrogen and D is N$^+$R. However, it cannot be excluded with absolute certainty that the radical R is in position 3 (i.e. that A is N$^+$R and D is nitrogen).

Preferred compounds of formula I are those in which $R^1$ is hydrogen, halogen, ($C_1$–$C_4$)-alkyl, ($C_1$–$C_4$)-haloalkyl or ($C_3$–$C_5$)-cycloalkyl;

$R^2$ and $R^3$ are identical or different and are each hydrogen, ($C_1$–$C_4$)-alkyl, ($C_1$–$C_4$)-haloalkyl, ($C_2$–$C_4$)-alkenyl, ($C_2$–$C_4$)-haloalkenyl, ($C_2$–$C_4$)-alkynyl, ($C_2$–$C_4$)-haloalkynyl, trimethylsilylalkynyl, ($C_1$–$C_4$)-alkoxy, ($C_1$–$C_4$)-haloalkoxy, ($C_1$–$C_4$)-alkoxy-($C_1$–$C_4$)-alkyl, ($C_1$–$C_4$)-haloalkoxy-($C_1$–$C_4$)-alkyl, ($C_1$–$C_4$)-alkoxy-($C_1$–$C_4$)-haloalkyl, ($C_1$–$C_4$)-haloalkoxy-($C_1$–$C_4$)-haloalkyl, halogen, hydroxy, ($C_1$–$C_4$)-hydroxyalkyl, ($C_1$–$C_4$)-alkanoyl, ($C_1$–$C_4$)-haloalkanoyl, ($C_3$–$C_5$)-cycloalkyl, ($C_3$–$C_5$)-halocycloalkyl, cyano, ($C_1$–$C_4$)-cyanoalkyl, nitro, ($C_1$–$C_4$)-nitroalkyl, thiocyanato, ($C_1$–$C_4$)-thiocyanatoalkyl, ($C_1$–$C_4$)-alkoxycarbonyl, ($C_1$–$C_4$)-alkoxycarbonyl-($C_1$–$C_4$)-alkyl, ($C_1$–$C_4$)-haloalkoxycarbonyl, ($C_1$–$C_4$)-alkylthio, ($C_1$–$C_4$)-alkylthio-($C_1$–$C_4$)-alkyl, ($C_1$–$C_4$)-haloalkylthio, ($C_1$–$C_4$)-alkylsulfinyl, ($C_1$–$C_4$)-haloalkylsulfinyl, ($C_1$–$C_4$)-alkylsulfonyl ($C_1$–$C_4$)-haloalkylsulfonyl; amino, ($C_1$–$C_4$)-alkylamino or $C_1$–$C_4$)-dialkylamino $R^2$ and $R^3$ together with the linking carbon atoms form an unsaturated 5- or 6-membered carbocyclic ring which, if it is a 5-membered ring, may contain an oxygen or sulfur atom in the place of a $CH_2$ or which, or which may, if it is a 6-membered ring, contain one or two nitrogen atoms instead of one or two CH units, and which may be substituted by 1, 2 or 3 identical or different radicals, these radicals being $(C_1-C_4)$-alkyl, $(C_1-C_4)$-haloalkyl, preferably trifluoromethyl, halogen, $(C_1-C_4)$-alkoxy or $(C_1-C_4)$-haloalkoxy; or $R^2$ and $R^3$ together with the linking carbon atoms form a 5-, 6- or 7-membered alicyclic ring which may contain oxygen and/or sulfur in the place of one or two carbon ring members and which is, if desired, substituted by 1, 2 or 3 $(C_1-C_4)$-alkyl groups.

It is also preferred that $R^1$ is hydrogen, methyl, fluorine or chlorine;

$R^2$ and $R^3$ are each hydrogen, $(C_1-C_4)$-alkyl, $(C_2-C_4)$-alkenyl, $(C_2-C_4)$-alkynyl, amino, $(C_1-C_4)$-alkylamino, $(C_1-C_4)$-dialkylamino, trimethysilylethynyl, methoxycarbonyl, $(C_1-C_4)$-haloalkyl, $(C_2-C_4)$-haloalkenyl, methoxy, ethoxy, halogen, methoxymethyl or cyano; or $R^2$ and $R^3$ join with the linking carbon atoms to form an unsaturated 5- or 6-membered ring with or without substitution which may, in the case of the 5-membered ring, contain a sulfur atom instead of a $CH_2$ unit; or $R^2$ and $R^3$ join with the linking carbon atoms to form a saturated 5- or 6-membered ring which may contain a sulfur or oxygen atom instead of a $CH_2$ unit;

X is NH or oxygen.

Similarly preferred compounds are those in which $R^4$ and $R^{4'}$ are hydrogen, fluorine, chlorine; methyl or trifluoromethyl, especially e hydrogen or methyl q is preferably 0 to 1, especially 1, whereby the aromatic ring system on the cycloalkyl group is cis or trans to the X group and in the case that the cycloalkyl group is cyclohexyl (n=1) and the above preferred units are in the 1,4 position then the cis configuration is preferred.

l is preferably 1 or 2 and m is preferably 0 or 1.

Each $R^9$ which may be the same or different from any other $R^9$ substituent is preferably $(C_2-C_4)$-haloalkenyloxy, $(C_2-C_4)$-haloalkynyloxy, $(C_1-C_4)$-haloalkoxy-$(C_1-C_4)$-haloalkoxy, oxiran-2-ylmethoxy, oxetan-2-ylmethoxy, hydroxy, heterocyclyoxy, in which the heterocyclyloxy can be substituted with up to 3 and, in the case of fluorine up to the maximum amount, of the same or different substituents $D^1R^{12}$, cyano, nitro or halogen or $R^9$ is $Z—R^{11}$, Z is $OSO_2$, $OSO_2NR^{13}$, $U^1P$ $(W^1)$ $V^1V^2$ or $U$ $C(W)V$; and U, $U^1$ and W are oxygen, V, $V^1$ and $V^2$ are a direct bond, $NR^{13}$, oxygen, in which $R^{13}$ is hydrogen $(C_1-C_4)$-alkyl or $(C_1-C_4)$-alkanoyl in which on the $V^1$ and $V^2$ groups is a group $R^{11}$ which together with the phosphorus atom can form a cyclic group, such as

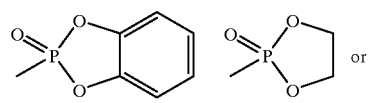

-continued

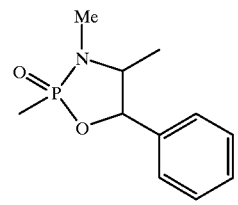

$R^{11}$ is $(C_1-C_8)$-alkyl, aryl $(C_1-C_2)$-alkyl, $(C_2-C_8)$-alkenyl, $(C_2-C_8)$-alkynyl, $(C_3-C_8)$-alkynyl, $(C_3-C_8)$-cycloalkyl, $(C_4-C_8)$-cycloalkenyl and these groups can be optionally substituted with up 3 and in the case of fluorine up to the maximum amount of the same or different groups $D^2R^{14}$ or $R^{11}$ is aryl or heterocyclyl in which both groups are unsubstituted or can be substituted with up to 3 and, in the case of fluorine, up to the maximum amount of the same or different groups $D^3R^{15}$ or each $R^{10}$ which can be the same or different from any other $R^{10}$ group is hydrogen, cyano, nitro, halogen, $(C_1-C_4)$-alkyl, $(C_1-C_2)$-haloalkyl or $(C_2-C_4)$-alkenyl or 2 adjacent groups $R^9$ and/or $R^{10}$ together with carbon atom to which they are attached can form an unsaturated 6-membered carbocyclic ring or 2 adjacent groups $R^9$ and/or $R^{10}$ together with a carbon atom to which they are attached can form a saturated 5 or 6-membered, cyclic ring which a $CH_2$ group can be replaced by an oxygen or sulphur.

Particularly preferred are compounds of formula 1 in which $R^1$ is hydrogen or methyl and $R^2$ and $R^3$ are hydrogen, methyl, ethyl, propyl, methoxy, $(C_2-C_3)$-alkenyl, amino, $(C_1-C_4)$-alkylamino, di-$(C_1-C_4)$-alkylamino, $(C_2-C_3)$-chloro- or fluoro-alkenyl $(C_2-C_3)$-alkynyl, trimethylsilylethynyl, $(C_2-C_3)$-chloro- or fluoro-alkyl, methoxymethyl, halo or cyano or $R^2$ and $R^3$ together with a ring system to which they are bound can form a quinazoline or quinoline system in which the carbocylic part can be substituted by fluorine or $R^2$ and $R^3$ together with the carbon atoms to which they are attached can form a saturated 6-membered ring which in place of the $CH_2$ group can contain an oxygen or sulphur atom.

Particularly preferred compounds are those wherein $R^1$ is hydrogen or methyl, $R^2$ is methyl, ethyl, propyl, isopropyl, vinyl, ethynyl, $(C_1-C_2)$-fluoroalkyl or methoxymethyl, $R^3$ is fluorine, chlorine, bromine, cyano, vinyl, ethynyl, $(C_1-C_2)$-fluoroalkyl, amino, $(C_1-C_2)$-alkylamino $(C_1-C_2)$-dialkylamino or methoxy or in the case that A is nitrogen, $R^2$ and $R^3$ together with a ring system to which they are formed can form a quinazoline group which can be substituted with fluorine and X is NH.

Also preferred are compounds of formula I, in which $R^4$ and $R^{4'}$ are hydrogen, q is 1 whereby in the aromatic system attached to the 4 position of the cyclohexyl group is in the cis configuration in relation to X, l is 1 and m is 0, $R^9$ is defined above and each $R^{10}$ independently of each other are hydrogen, methyl, cyano, nitro, fluorine or chlorine.

Even more preferred are compounds of formula I in which $R^1$ is hydrogen, $R^2$ is ethyl or methoxymethyl,
$R^3$ is fluorine, chlorine, bromine or methoxy and especially $R^2$=ethyl, and $R^3$=chlorine,
A is nitrogen,
X is NH,
$R^4$ and $R^{4'}$ are H,
$R^9$ is as defined above and is preferably in the 4 position of the aromatic ring whereby the aromatic group on the cyclohexane ring and the substituent X are in the cis configuration in relation to each other,
$R^{10}$ is hydrogen.

Of these, preferred compounds are those in which
$R^9$ is $(C_2-C_4)$-haloalkenyloxy, $(C_2-C_4)$-haloalkynyloxy, oxetan-2-ylmethoxy, hydroxy, heterocyclyloxy, heterocyclyoxy substituted with $D^1R^{12}$, cyano nitro or halo or is a group $ZR^{11}$, in which
Z is $OSO_2$, $U^1P(W^1)V^1V^2$ or UC(W)V and
W is oxygen,
$W^1$ is oxygen or sulphur,
V, $V^1$ and $V^2$ are a direct bond, $NR^{13}$ or oxygen in which $R^{13}$ is hydrogen or $(C_1-C_4)$-alkyl,
$R^{11}$ is $(C_{1-4})$-alkyl, aryl $CH_2-(C_{2-4})$-alkenyl, $(C_2-C_4)$-alkynyl, $(C_3-C_6)$-cycloalky and these groups can optionally be substituted by up to 3 and, in the case of fluorine up to the maximum amount, of the same or different groups $D^3R^{15}$, or
$R^{11}$ is aryl or heterocyclyl in which both these groups are unsubstituted or substituted with up to 3 and, in the case of fluorine up the maximum amount, of the same or different groups $D^3R^{15}$ or in which
$D^1$, $D^2$ and $D^3$ independently of each other are a direct bond or oxygen
$R^{12}$, $R^{14}$ and $R^{15}$, independently of each other, are hydrogen, cyano, nitro, halogen, $(C_{1-4})$-alkyl, $(C_{1-4})$-haloalkyl, $(C_2-C_4)$-alkenyl, $(C_2-C_4)$-haloalkenyl, $(C_2-C_4)$-alkynyl, $(C_2-C_4)$-haloalkynyl, $(C_3-C_6)$-cycloalkyl, $(C_4-C_6)$-cycloalkenyl, aryl, heterocyclyl, whereby in the last named 4 groups the cycloaliphatic, aromatic or heterocyclic ring system are unsubstituted or substituted with up to 3, and in the case of fluorine up to the maximum amount, of the same or different substituents of $R^{18}$, in which
$R^{18}$ is $(C_1-C_4)$-alkyl, $(C_{1-4})$-haloalkyl, $(C_{1-4})$-alkoxy, $(C_1-C_4)$-haloalkoxy, cyano, nitro or halogen.

It is also preferred that
A is nitrogen and D is $N^+R$ or nitrogen; and
$Q^{n-}$ is an anion, such as $Hal^-$, $NO_3^-$, $BF_4^-$, $BPh_4^-$ or $PF_6^-$;

In the above formula I, the radicals alkyl, alkoxy, haloalkyl, haloalkoxy, alkylamino and alkylthio and the corresponding unsaturated and/or substituted radicals can in each case be straight-chain or branched in the carbon skeleton. Unless specifically mentioned, the lower carbon skeletons, for example those having 1 to 6 carbon atoms or, in the case of unsaturated groups, 2 to 6 carbon atoms, are preferred for these radicals. alkyl radicals, also in the composite meanings such as alkoxy, haloalkyl and the like, are, for example, methyl, ethyl, n- or i-propyl, n-, i-, t- or 2-butyl, pentyl radicals, hexyl radicals, such as n-hexyl, i-hexyl and 1,3-dimethylbutyl, heptyl radicals, such as n-heptyl, 1-methylhexyl and 1,4-dimethylpentyl; alkenyl and alkynyl radicals have the meanings of the unsaturated radicals which are possible and which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl. cycloalkyl is a carbocyclic saturated ring system preferably having 3–8 carbon atoms, for example cyclopropyl, cyclopentyl or cyclohexyl, but also bicyclic systems, for example the norbornyl group, the bicyclo[2.2.2]octane radical and tricyclic systems, for example adamantyl.

halogen is, for example, fluorine, chlorine, bromine or iodine. haloalkyl, haloalkenyl and haloalkynyl are alkyl, alkenyl and alkynyl, respectively, which are partially or fully substituted by halogen, preferably by fluorine, chlorine and/or bromine, in particular by fluorine or chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies analogously to haloalkenyl and other halogen-substituted radicals.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl. Preferably, a hydrocarbon radical is alkyl, alkenyl or alkynyl having up to 12 carbon atoms or cycloalkyl having 3, 4, 5, 6 or 7 ring atoms or phenyl. The same applies analogously to a hydrocarbon radical in a hydrocarbonoxy radical.

aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocycle) can be saturated, unsaturated or heteroaromatic; it preferably contains one or more hetero units in the ring, i.e. hetero atoms or ring members, including substituted hetero atoms, preferably selected from the group consisting of N, O, S, SO, $SO_2$; it is preferably an aliphatic heterocyclyl radical having 3 to 7 ring atoms or a heteroaromatic radical having 5 or 6 ring atoms and it contains 1, 2 or 3 hetero units. The heterocyclic radical can be, for example, a heteroaromatic radical or ring (heteroaryl), for example a mono-, bi- or polycyclic aromatic system in which at least 1 ring contains one or more hetero atoms, in particular an aromatic system in which at least 1, preferably up to 4, in particular up to 2 CH are replaced by N and/or at least 1, preferably up to 3, —CH=CH-units is replaced by NH, S or O adjacent oxygen atoms being excluded, for example pyridyl, pyrimidinyl, pyridazinyl, pyrazinyl, thienyl, thiazolyl, oxazolyl, furyl, pyrrolyl, pyrazolyl and imidazolyl, or it is a partially or fully hydrogenated radical such as oxiranyl, pyrrolidinyl, piperidinyl, piperazinyl, dioxolanyl, morpholinyl, tetrahydrofuryl. Substituents which are suitable for a substituted heterocyclic radical are the substituents mentioned further below, and additionally oxo. The oxo group can also be present on the hetero ring atoms, which can exist at various oxidation levels, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxy, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl, cycloalkyl and haloalkyl; the term "substituted radicals" such as substituted alkyl etc. includes as substituents, in addition to the saturated hydrocarbon-containing radicals mentioned, corresponding unsaturated aliphatic and aromatic radicals, such as alkenyl, alkynyl, alkenyloxy, alkynyloxy, phenyl, phenoxy, etc., with or without substitution. Preferred among the radicals having carbon atoms are those having 1 to 4 carbon atoms, in particular 1 or 2 carbon atoms. Preferred substituents are generally selected from the group consisting of halogen, for example fluorine and chlorine, $(C_1-C_4)$-alkyl, preferably methyl or ethyl, $(C_1-C_4)$-haloalkyl, preferably trifluoromethyl, $(C_1-C_4)$-alkoxy, preferably methoxy or ethoxy, $(C_1-C_4)$-haloalkoxy, nitro and cyano. Especially preferred are the substituents methyl, methoxy and chlorine.

Mono- or disubstituted amino is a chemically stable radical selected from the group consisting of the substituted amino radicals which are N-substituted, for example by one or two identical or different radicals selected from the group consisting of alkyl, alkoxy, acyl and aryl; preferably monoalkylamino, dialkylamino, acylamino, arylamino, N-alkyl-N-arylamino and N-heterocycles; preference is given to alkyl radicals having 1 to 4 carbon atoms; aryl is preferably phenyl or substituted phenyl; acyl is defined as indicated further below and is preferably $(C_1-C_4)$-alkanoyl. The same applies analogously to substituted hydroxylamino or hydrazino.

Unsubstituted or substituted phenyl is preferably phenyl which is unsubstituted or mono- or polysubstituted, preferably up to trisubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

An acyl radical is the radical of an organic acid, for example the radical of a carboxylic acid and radicals of acids derived therefrom, such as thiocarboxylic acid, iminocarboxylic acids with or without N-substitution, or the radical of carbonic monoesters, carbamic acid with or without N-substitutien, sulfonic acids, sulfinic acids, phosphonic acids, phosphinic acids. acyl is, for example, formyl, alkylcarbonyl such as [$(C_1-C_4)$alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. In each case, the radicals may be substituted even further in the alkyl or phenyl moiety, for example in the alkyl moiety by one or more radicals selected from the group consisting of halogen, alkoxy, phenyl and phenoxy; examples of substituents in the phenyl moiety are the substituents already mentioned further above in general for substituted phenyl.

Furthermore, in the above formulae the term "dimethyl-$(C_1-C_8)$-alkylsilylethynyl" denotes, for example, the trimemethylsilylethynyl or the tert-butyldimethylsilylethynyl group;

the term "$(C_1-C_4)$-hydroxyalkyl" denotes, for example, the hydroxymethyl, 1-hydroxyethyl, 2-hydroxyethyl, 1-hydroxy-1-methylethyl or the 1-hydroxypropyl group;

the term "$(C_1-C_4)$-alkanoyl" denotes, for example, the formyl, acetyl, propionyl, 2-methylpropionyl or butyryl group;

the term "$(C_1-C_{12})$-alkanoyl" denotes, for example, the abovementioned radicals and, for example, the valeroyl, pivaloyl, hexanoyl, decanoyl or the dodecanoyl group;

the term "$(C_2-C_4)$-haloalkanoyl" denotes a $(C_1-C_4)$-alkanoyl group in which the hydrogen atoms are partly, in the case of fluorine partly or wholly, replaced by halogen atoms, preferably fluorine or chlorine;

the term "$(C_2-C_{12})$-haloalkanoyl" denotes a $(C_1-C_{20})$-alkanoyl group in which the hydrogen atoms are partly, in the case of fluorine partly or wholly, replaced by halogen atoms, preferably fluorine or chlorine;

the term "cyano-$(C_1-C_4)$-alkyl" denotes a cyanoalkyl group whose hydrocarbon radical has the meanings given for the term "$(C_1-C_4)$-alkyl";

the term "$(C_1-C_4)$-alkylamino" denotes, for example, methylamino, ethylamino, isopropylamino;

the term "$(C_1-C_4)$-dialkylamino" denotes, for example, dimethylamino, N-ethyl-N-methylamino, diethylamino, the term "$(C_1-C_4)$-alkoxycarbonyl" denotes, for example, the methoxycarbonyl, ethoxycarbonyl, propoxycarbonyl, butoxycarbonyl or tert-butoxycarbonyl group;

the term "$(C_1-C_{12})$-alkoxycarbonyl" denotes the abovementioned radicals and, for example, the hexyloxycarbonyl, 2-methylhexyloxycarbonyl, decyloxycarbonyl or dodecyloxycarbonyl group;

the term "$(C_1-C_4)$-haloalkoxycarbonyl" denotes a $(C_1-C_4)$-alkoxycarbonyl group in which one or more, in the case of fluorine possibly all, hydrogen atoms are replaced by halogen, preferably fluorine or chlorine;

the term "$(C_1-C_4)$-haloalkylthio" denotes a $(C_1-C_4)$-alkylthio group in which one or more, in the case of fluorine possibly all, hydrogen atoms of the hydrocarbon moiety are replaced by halogen, in particular chlorine or fluorine;

the term "$(C_1-C_4)$-alkylsulfinyl" denotes, for example, the methyl-, ethyl-, propyl-, isopropyl-, butyl-, isobutyl-, sec-butyl- or tert-butylsulfinyl group;

the term "$(C_1-C_4)$-alkylsulfonyl" denotes, for example, the methyl-, ethyl-, propyl-, isopropyl-, butyl-, isobutyl-, sec-butyl- or tert-butylsulfonyl group;

the terms "$(C_1-C_4)$-haloalkylsulfinyl" and "$(C_1-C_4)$-haloalkylsulfonyl" denote $(C_1-C_4)$-alkylsulfinyl and -sulfonyl radicals having the abovementioned meanings in which one or more, in the case of fluorine possibly all, hydrogen atoms of the hydrocarbon moiety are replaced by halogen, in particular chlorine or fluorine;

the term "$(C_1-C_4)$-alkoxy-$(C_1-C_4)$-alkyl" denotes, for example, a 1-methoxyethylene group, a 2-methoxyethyl group, a 2-ethoxyethyl group, a methoxymethyl or ethoxymethyl group, a 3-methoxypropyl group or a 4-butoxybutyl group;

the terms "$(C_1-C_4)$-haloalkoxy-$(C_1-C_4)$-alkyl", "$(C_1-C_4)$-alkoxy-$(C_1-C_4)$-haloalkyl" and "$(C_1-C_4)$-haloalkoxy-$(C_1-C_4)$-haloalkyl" denote $(C_1-C_4)$-alkoxy-$(C_1-C_4)$-alkyl radicals having the abovementioned meanings where one or more, in the case of fluorine possibly all, hydrogen atoms of the appropriate hydrocarbon moieties are replaced by halogen, preferably chlorine or fluorine;

the term "$(C_1-C_4)$-alkylthio-$(C_1-C_4)$-alkyl" denotes, for example, methylthiomethyl, ethylthiomethyl, propylthiomethyl, 2-methylthioethyl, 2-ethylthioethyl or 3-methylthiopropyl;

the term "arylthio" denotes, for example, the phenylthio or the 1- or 2-naphthylthio group;

the term "aryloxy" denotes, for example, the phenoxy- or 1- or 2-naphthyloxy group;

the term "heterocyclyloxy" or "heterocyclylthio" denotes one of the abovementioned heterocyclic radicals which are linked via an oxygen or sulfur atom;

the term "cycloalkoxy" or "cycloalkylthio" denotes one of the abovementioned cycloalkyl radicals which are linked via an oxygen or sulfur atom;

the term "aroyl" denotes, for example, the benzoyl, naphthoyl or the biphenylcarbonyl group;

the term "aryl-$(C_1-C_4)$-alkanoyl" denotes, for example, the phenylacetyl, 3-phenylpropionyl, 2-phenylpropionyl, 2-methyl-2-phenylpropionyl, 4-phenylbutyryl or the naphthylacetyl group;

the term "$(C_3-C_8)$-cycloalkyl-$(C_1-C_4)$-alkanoyl" denotes, for example, the cyclopropylcarbonyl, cyclobutylcarbonyl, cyclopentylcarbonyl, cyclohexylcarbonyl, cyclohexylacetyl or the cyclohexylbutyryl group;

the term "heterocyclyl-$(C_1-C_4)$-alkanoyl" denotes, for example, the thenoyl, furoyl, nicotinoyl, thienylacetyl or the pyridinepropionyl group;

the term "$(C_3-C_8)$-cycloalkoxycarbonyl" denotes, for example, the cyclobutyloxycarbonyl, cyclopentyloxycarbonyl, cyclohexyloxycarbonyl or the cycloheptyloxycarbonyl group;

the term "$(C_3-C_8)$-cycloalkyl-$(C_1-C_4)$-alkoxycarbonyl" denotes, for example, the cyclopropylmethoxycarbonyl, cyclobutylmethoxycarbonyl, cyclopentyloxymethoxycarbonyl, cyclohexyloxymethoxycarbonyl, 1-(cyclohexyl)-ethoxycarbonyl or the 2-(cyclohexyl)ethoxycarbonyl group;

the term "aryl-$(C_1-C_4)$-alkoxycarbonyl" denotes, for example, the benzyloxycarbonyl, 1-naphthylmethoxycarbonyl, 2-naphthylmethoxycarbonyl, 1-phenylethoxycarbonyl or the 2-phenylethoxycarbonyl group;

the term "heterocyclyl-$(C_1-C_4)$-alkoxycarbonyl" denotes, for example, the thienylmethoxycarbonyl, furylmethoxycarbonyl, tetrahydrofurylmethoxycarbonyl or the pyridylethoxycarbonyl group;

the term "aryloxycarbonyl" denotes, for example, the phenoxycarbonyl, naphthoxycarbonyl or the biphenyloxycarbonyl group;

the term "heterocyclyloxycarbonyl" denotes, for example, the tetrahydropyran-4-oxycarbonyl group;

the term "$(C_1-C_{20})$-alkanoyloxy" denotes, for example, the formyloxy, acetoxy, propionyloxy, butyryloxy, pivaloyloxy, valeroyloxy or the hexanoyloxy group;

the term "$(C_2-C_{20})$-haloalkanoyloxy" denotes a $(C_2-C_{20})$-alkanoyloxy group in which one or more, in the case of fluorine possibly all, hydrogen atoms of the hydrocarbon moiety are replaced by halogen, in particular fluorine or chlorine;

the term "$(C_3-C_8)$-cycloalkanoyloxy" denotes, for example, the cyclopropanoyloxy, cyclobutenoyloxy, cyclopentanoyloxy, cyclohexanoyloxy or the cycloheptanoyloxy group;

the term "$(C_3-C_8)$-cycloalkyl-$(C_1-C_4)$-alkanoyloxy" denotes, for example, the cyclopropylcarbonyloxy, cyclopropylacetoxy, cyclobutylcarbonyloxy, cyclopentylcarbonyloxy, cyclohexylcarbonyloxy, cyclohexylacetoxy or the 4-cyclohexylbutyryloxy group;

the term "aroyloxy" denotes, for example, the benzoyloxy or the naphthoyloxy group;

the term "aryl-$(C_1-C_4)$-alkanoyloxy" denotes, for example, the benzyloxy, naphthoyloxy, biphenylcarbonyloxy, phenylacetoxy or the phenylbutyryloxy group;

the term "heterocyclyl-$(C_1-C_4)$-alkanoyloxy" denotes, for example, the thienylcarbonyloxy, thienylacetoxy, pyridylcarbonyloxy or the pyrimidinylcarbonyloxy group;

the term "$(C_1-C_{20})$-alkylsulfonyloxy" denotes, for example, the methane-, ethane-, butane- or hexanesulfonyloxy group;

the term "arylsulfonyloxy" denotes, for example, the phenylsulfonyloxy or the toluenesulfonyloxy group;

a bivalent hydrocarbon chain denotes a radical which is derived from n-alkanes or n-alkenes by removal of in each case one hydrogen atom from each of the two terminal carbon atoms of the chain, such as methylene, ethanediyl, trimethylene, tetramethylene;

the term $(C_1-C_{18})$-alkanediyldioxy denotes a bivalent radical derived from $(C_1-C_{18})$-alkanes by replacement of two hydrogen atoms by two —O— radicals.

The illustration given above applies correspondingly to homologues or to radicals derived therefrom.

In addition to the cis/trans isomerism mentioned, some of the compounds of the formula I have one or more asymmetric carbon atoms or stereoisomers at double bonds. Enantiomers or diastereomers may therefore be present. The invention embraces both the pure isomers and mixtures thereof. Mixtures of diastereomers can be separated into the components by conventional methods, for example by selective crystallisation from suitable solvents or by chromatography. Racemates can be separated into the enantiomers by conventional methods, for example by salt formation with an optically active acid, separation of the diastereomeric salts and liberation of the pure enantiomers using a base.

The invention furthermore relates to a process for preparing compounds of the formula I which comprises reacting a compound of the formula II

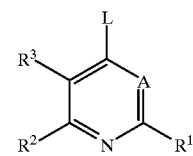

(II)

where $R^1$, $R^2$ and $R^3$ have the meanings given above, A is CH or N and L is a leaving group, for example halogen, alkylthio, alkanesulfonyloxy or arylsulfonyloxy, alkylsulfonyl or arylsulfonyl, with a nucleophile of formula III

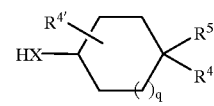

(III)

where X, q, $R^4$, $R^{4'}$ and $R^5$ are as defined under formula I, and, if desired, converting the compound of the formula I obtained in this manner or in another manner, into its N-oxide and/or salt and optionally the nitrogen heterocycle or the side chain $R^5$ can be derivatised in known manner A typical reaction scheme is as follows

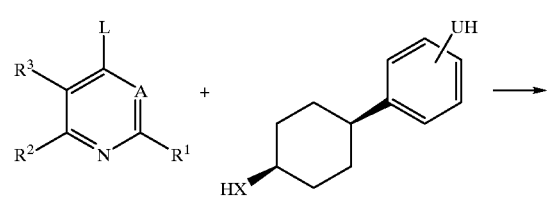

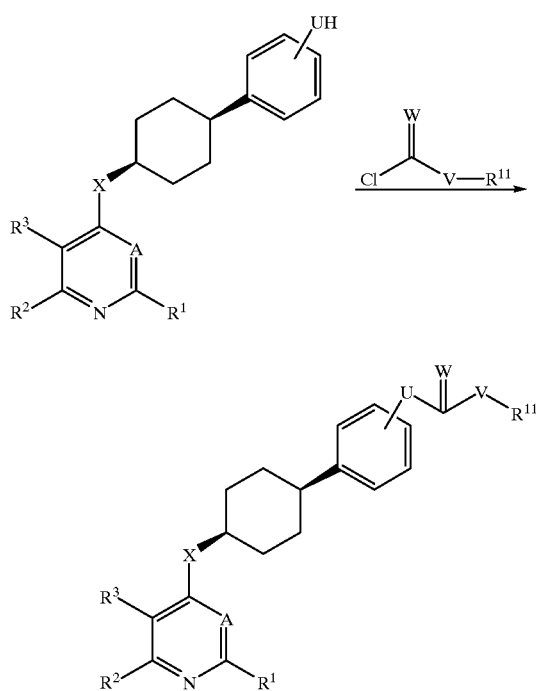

The substitution reaction described above is known in principle. The leaving group L can be varied within wide limits and can be, for example, a halogen atom, such as fluorine, chlorine, bromine or iodine; or alkylthio, such as methyl- or ethylthio; or alkylsulfonyloxy, such as methane-, trifluoromethyl- or ethylsulfonyloxy; or arylsulfonyloxy, such as benzenesulfonyloxy; or toluenesulfonyloxy, or alkylsulfonyl such as methyl- or ethylsulfonyl; or arylsulfonyl such as phenyl- or toluenesulfonyl.

The abovementioned reaction is carried out in a temperature range from 20–150° C., advantageously in the presence of a base and, if appropriate, in an inert organic solvent such as N,N-dimethylformamide, N,N-dimethylacetamide, dimethyl sulfoxide, N-methylpyrrolidin-2-one, dioxane, tetrahydrofuran, 4-methyl-2-pentanone, methanol, ethanol, butanol, ethylene glycol, ethylene glycol dimethyl ether, toluene, chlorobenzene or xylene. It is also possible to employ mixtures of these solvents.

Suitable bases in the case where X is oxygen are, for example, alkali metal or alkaline earth metal carbonates, bicarbonates, amides or hydrides, such as sodium carbonate, sodium bicarbonate, potassium carbonate, sodium amide or sodium hydride, and in the case where X is NH, these are, for example, alkali metal or alkaline earth metal carbonates, bicarbonates, hydroxides, amides or hydrides such as sodium carbonate, sodium bicarbonate, potassium carbonate, sodium hydroxide, sodium amide or sodium hydride, or organic bases, such as triethylamine or pyridine, or else a second equivalent of the nucleophile where X=NH.

The compounds of the formula II required as starting materials are in most cases known from the literature or can be prepared by methods similar to those that are known (cf. EP-A-370 391, EP-A-470 600, DE-A-43 31 179, DE-A-44 04 702).

To prepare the nucleophiles of the formula III, suitably substituted cyclopentanones, cyclohexanones or cycloheptanones which are either known commercially or can be obtained in known manner are converted into the corresponding amines by reductive amination ($H_2$, $NH_3$, metal catalyst or ammonium acetate/sodium cyanoborohydride) or by a Leuckart-Wallach reduction) or into the corresponding alcohols by reduction with a complex metal hydride. For the preparation of the especially preferred cis derivatives this can be done suitably by reductive amination especially using a rhodium or a rhodium/palladium mixed catalyst, and as the complex metal hydride especially suitable are those which besides the hydrogen carry bulky alkyl substituents, such as for example L-Selectride.

Alternatively, there is the possibility that cycloalkanones, can be reduced with a complex metal hydride ($LiAlH_4$, $NaBH_4$) to the corresponding alcohols, and from these via the mesylate or tosylate ($CH_3SO_2Cl/CH_3C_6H_4SO_2Cl$, pyridine) and azide ($NaN_3$, DMF) to obtain the amine (H2/Pd or $LiAlH_4$) (see C. D. Lednicer, D. E. Emmert, R. Lakti, A. D. Rudzik, J. Med. Chem. 15, 1239, (97-2). The chosen alcohols can be obtained also directly from aldehydes and glycerines with acid catalysis (P. E. Verkade, J. D. van Roon, Rec. Trav. Chim. Holland, 61, 831 (1942); E. Juaristi, S. Antunez, Tetrahedron 48, 5941 (1992)).

Compounds of formula I in which A or D have the meaning $N^+Rx1/nQ^{n-}$ can be obtained in known methods by quaternisation of the compounds of formula I in which A is CH or N and D is N (e.g. as described in our DE 19647402, 19647413 1967317 and 19719590.

While being tolerated well by plants and having favourable toxicity toward warm-blooded animals, the active substances are suitable for controlling animal pests, especially insects, arachnids, helminths and molluscs, and very particularly preferably for controlling insects and arachnids, which are encountered in agriculture, in animal breeding, in forestry, in the protection of stored products and materials, and in the hygiene sector. They are active against normally sensitive and resistant species and against all or certain stages of development. The abovementioned pests include:

From the order of the Acarina, for example *Acarus siro*, Argas spp., Omithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp. and Eutetranychus spp.

From the order of the isopoda, for example *Oniscus asselus, Armadium vulgar* and *Porcellio scaber*.

From the order of the Diplopoda, for example *Blaniulus guttulatus*.

From the order of the Chilopoda, for example *Geophilus carpophagus* and Scutigera spp.

From the order of the Symphyla, for example *Scutigerella immaculata*.

From the order of the Thysanura, for example *Lepisma saccharina*.

From the order of the Collembola, for example *Onychiurus armatus*.

From the order of the Orthoptera, for example *Blatta orientalis, Periplaneta americana, Leucophaea madeirae, Blatella germanica, Acheta domesticus*, Gryllotalpa spp., *Locusta migratoria migratorioides, Melanoplus differentialis* and *Schistocerca gregaria*.

From the order of the isoptera, for example Reticulitermes spp.

From the order of the Anoplura, for example *Phylloera vastatrix*, Pemphigus spp., *Pediculus humanus corporis*, Haematopinus spp. and Linognathus spp.

From the order of the Mallophaga, for example Trichodecte spp. and Damalinea spp.

From the order of the Thysanoptera, for example *Hercinothrips femoralis, Thrips tabaci* and Frankliniella spp.

From the order of the heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum*, Aphis spp., *Brevicoryne brassicae, Cryptomyzus ribis, Doralis fabae, Doralis pomi, Eriosoma lanigerum, Hyalopterus arandinis, Macrosiphum avenae*, Myzus spp., *Phorodon humuli, Rhopalosiphum padi*, Empoasca spp., *Euscelus bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp., *Bucculatrix thurberiella, Phyllocnistis citrella*, Agrotis spp., Euxoa spp., Feltia spp., *Earias insulana*, Heliothis spp., *Laphygma exigua, Mamestra brassicae, Panolis flammea, Prodenia litura*, Spodoptera spp., *Trichoplusia ni, Carpocapsa pomonella*, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima, Tortrix viridana*, Cuaphalocrocis spp. and Manduca spp.

From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae*, Diabrotica spp., *Psylloides chrysocephala, Epilachna varivestis*, Atomaria spp., *Oryzaephilus surinamensis*, Anthonumus spp., Sitophilus spp., *Otiorrhynchus sulcatus, Cosmopolites sordidus, Ceuthorrynchus assimilis, Hypera postica*, Dermestes spp., Trogorma, Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conorus spp., *Melolontha melolontha, Amphimallon solstitialis, Costelytra zealandica* and Lissorhoptus spp.

From the order of the Hymenoptera, for example Diprion spp., Hoplocampa spp., Lasius spp., *Monomorium pharaonis* and Vespa spp.

From the order of the Diptera, for example Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hypobosca spp., Stomoxys spp., Oestrus spp., Hyporma spp., Tabanus spp., Tannia spp., *Bibio hortulanus, Oscinella frit*, Phorbia spp., *Pegomyia hyoscyami, Ceratitis capitata, Dacus oleae* and *Tipula paludosa*.

From the order of the Siphonaptera, for example *Xenopsylla cheopsis* and Ceratophyllus spp.

From the order of the Arachnida, for example *Scorpio maurus* and *Latrodectus mactans*.

From the class of the helminths, for example Haemonchus, Trichostrongulus, Ostertagia, Cooperia, Chabertia, Strongyloides, Oesophagostomum, Hyostrongulus, Ancylostoma, Ascaris and Heterakis and also Fasciola.

From the class of the Gastropoda, for example, Deroceras spp., Arion spp., Lymnaea spp., Galba spp., Succinea spp., Biomphalaria spp., Bulinus spp. and Oncomelania spp.

From the class of the Bivalva, for example Dreissena spp.

The plant-parasitic nematodes which can be controlled in accordance with the invention include, for example, the root-parasitic soil nematodes such as, for example, those of the genera Meloidogyne (root-knot nematodes, such as Meloidogyne incognita, *Meloidogyne hapla* and *Meloidogyne javanica*), heterora and Globora (cyst-forming nematodes, such as *Globora rostochiensis, Globora pallida, heterora trifolii*) and of the genera Radopholus (such as *Radopholus similis*), Pratylenchus (such as *Pratylenchus neglectus, Pratylenchus penetrans* and *Pratylenchus curvitatus*), Tylenchulus (such as *Tylenchulus semipenetrans*), Tylenchorhynchus (such as *Tylenchorhynchus dubius* and *Tylenchorhynchus claytoni*), Rotylenchus (such as *Rotylenchus robustus*), Helicotylenchus (such as *Helicotylenchus multicinctus*), Belonoaimus (such as *Belonoaimus longicaudatus*), Longidorus (such as *Longidorus elongatus*), Trichodorus (such as *Trichodorus primitivus*) and Xiphinema (such as *Xiphinema index*).

The compounds according to the invention can also be used to control the nematode genera Ditylenchus (stem parasites, such as *Ditylenchus dipsaci* and *Ditylenchus destriuctor*), Aphelenchoides (leaf nematodes, such as *Aphelenchoides ritzemabosi*) and Anguina (leaf-gall nematodes, such as *Anguina tritici*).

The invention also relates to compositions, especially insecticidal and acaricidal compositions, which comprise the compounds of the formula I in addition to suitable formulation auxiliaries.

The compositions according to the invention comprise the active substances of the formulae I in general in a proportion of from 1 to 95% by weight. They can be formulated in various ways depending on the biological and/or chemico-physical parameters which prevail. Possible formulations which are suitable are therefore:

wettable powders (WP), emulsifiable concentrates (EC), aqueous solutions (SL), emulsions, sprayable solutions, oil- or water-based dispersions (SC), suspoemulsions (SE), dusts (DP), seed-dressing products, granules in the form of microgranules, spray granules, coated granules and adsorption granules, water-dispersible granules (WG), ULV formulations, microcapsules, waxes or baits.

These individual types of formulation are known in principle and are described, for example, in:

Winnacker-Küchler, "Chemische Technologie" [Chemical Technology], Volume 7, C. Hauser Verlag Munich, 4th ed. 1986; van Falkenberg, "Pesticides formulations", Marcel Dekker N.Y., 2nd ed. 1972–73; K. Martens, "Spray Drying Handbook", 3rd ed. 1979, G. Goodwin Ltd. London.

The formulation auxiliaries required, such as inert materials, surfactants, solvents and other additives, are likewise known and are described, for example, in:

Watkins, "Handbook of Insecticide Dust Diluents and Carriers", 2nd ed., Darland Books, Caldwell N.J.; H.v. Olphen, "Introduction to Clay Colloid Chemistry", 2nd ed., J. Wiley & Sons, N.Y.; Marsden, "Solvents Guide", 2nd ed., Interscience, N.Y. 1950; McCutcheon's, "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1967; Winnacker-Küchler, "Chemische Technologie", Volume 7, C. Hauser Verlag Munich, 4th ed. 1986.

Based on these formulations, it is also possible to produce combinations with other pesticidally active substances, fertilisers and/or growth regulators, for example in the form of a ready-mix or a tank mix. Wettable powders are preparations, uniformly dispersible in water, which contain, beside the active substance and in addition to a diluent or inert material, wetting agents, for example polyoxyethylated alkylphenols, polyoxyethylated fatty alcohols, alkyl- or alkylphenolsulfonates, and dispersing agents, for example sodium ligninsulfonate or sodium 2,2'-dinaphthylmethane-6,6'-disulfonate. Emulsifiable concentrates are prepared by dissolving the active substance in an organic solvent, for example butanol, cyclohexanone, dimethylformamide, xylene or higher-boiling aromatics or hydrocarbons, with addition of one or more emulsifiers. As emulsifiers, the following can be used, for example: calcium salts of alkylaryl-sulfonates, such as Ca dodecylbenzenesulfonate, or nonionic emulsifiers such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusts are obtained by grinding the active substance with finely divided solid substances, for example talc, natural clays such as kaolin, bentonite, pyrophillite or diatomaceous earth. Granules can be prepared either by atomizing the active substance onto adsorptive, granulated inert material or by applying active substance concentrates onto the surface of carrier materials such as sand or kaolinites, or of granulated inert material, by means of adhesives, for example polyvinyl alcohol or sodium polyacrylate, or alternatively mineral oils. Suitable active substances can also be granulated in the fashion conventional for the preparation of fertilizer granules, if desired as a mixture with fertilisers.

In wettable powders, the concentration of active substance is, for example, from approximately 10 to 90% by weight, the remainder to 100% by weight being composed of customary formulation components. In the case of emulsifiable concentrates, the concentration of active substance may be from approximately 5 to 80% by weight. Dust formulations comprise in most cases from 5 to 20% by weight of active substance, sprayable solutions from about 2 to 20% by weight. In the case of granules, the content of active substance depends partly on whether the active compound is in liquid or solid form and on which granulation auxiliaries, fillers, etc. are being used.

In addition, the abovementioned formulations of active substance comprise, if appropriate, the adhesives, wetting agents, dispersants, emulsifiers, penetrants, solvents, fillers or carriers which are customary in each case.

The concentrates, which are in the commercially customary form, are if appropriate diluted in the customary manner for their use, for example using water in the case of wettable powders, emulsifiable concentrates, dispersions and some microgranules. Dust and granule preparations, and also sprayable solutions, are normally not diluted any further with other inert substances before being used.

The application rate required varies with the external conditions, such as temperature and humidity among others. It can fluctuate within wide limits, for example between 0.0005 and 10.0 kg/ha or more of active substance, but is preferably between 0.001 and 5 kg/ha.

The active substances according to the invention may be present in their commercially customary formulations, and in the application forms prepared from these formulations, as mixtures with other active substances, such as insecticides, attractants, sterilants, acaricides, nematicides, fungicides, growth regulators or herbicides.

The active substance content of the use forms prepared from the commercially customary formulations can be from 0.00000001 to 95% by weight of active substance, preferably between 0.00001 and 1% by weight.

Application is effected in a conventional fashion, matched to the use forms.

The active substances according to the invention are also suitable for controlling ecto- and endoparasites in the veterinary medicine sector or in the sector of animal husbandry.

The active substances according to the invention are in this case applied in a known fashion, such as by oral application in the form of, for example, tablets, capsules, potions or granules, by dermal application in the form of, for example, dipping, spraying, pouring-on and spotting-on and powdering, and also by parenteral application in the form of, for example, injection.

The novel compounds, according to the invention, of the formula I can accordingly also be employed particularly advantageously in livestock husbandry (for example cattle, sheep, pigs and poultry such as chickens, geese etc.). In a preferred embodiment of the invention, the novel compounds, if appropriate in suitable formulations (cf. above) and if appropriate with the drinking water or feed, are administered orally to the animals. Since they are excreted in active form in the droppings, the development of insects in the animal droppings can be prevented very simply in this fashion. The dosages and formulations suitable in each case are particularly dependent on the type and stage of development of the productive animals and also on the degree of infestation, and can easily be determined and fixed by conventional methods. In the case of cattle, the novel compounds can be employed, for example, in dosages of 0.01 to 1 mg/kg of body weight.

Some compounds of the formula I according to the invention are also distinguished by an fungicidal action. Fungal pathogens which have already penetrated the plant tissue can be successfully subjected to curative control. This is particularly important and advantageous in the case of those fungal diseases which can no longer be controlled effectively with the otherwise customary fungicides when infection has taken place already. The spectrum of action of the claimed compounds embraces various economically important phytopathogenic fungi, for example *Plasmopara viticola, Phytophthora infestans, Erysiphe graminis, Pyricularia oryzae, Pyrenophora teres, Leptosphaeria nodorum, Pellicularia sasakii* and *Puccinia recondita*.

In addition, the compounds according to the invention are also suitable for use in technical fields, for example as wood preservatives, as preservatives in paints, in cooling lubricants for metalworking, or as preservatives in drilling and cutting oils.

The active substances according to the invention in their commercially customary formulations can be employed either alone or in combination with other fungicides known from the literature.

The abovementioned components for combinations are known active substances of which many are described in The Pesticide Manual, edited by C D S Tomlin, 11th edition (1997), bublished by the British Crop Protection Council. The active substance content of the use forms prepared from commercially customary formulations can vary within wide limits, and the concentration of active substance in the use forms can be from 0.0001 up to 95% by weight of active substance, preferably between 0.0001 and 1% by weight. The formulations are applied in a customary manner adapted to suit the use forms.

The examples which follow illustrate the invention without limiting it thereto.

A. FORMULATION EXAMPLES a) A dust is obtained by mixing 10 parts by weight of active substance and 90 parts by weight of talc as inert material and comminuting in a hammer mill.
b) A wettable powder which is easily dispersible in water is obtained by mixing 25 parts by weight of active substance, 65 parts by weight of kaolin-containing quartz as inert material, 10 parts by weight of potassium lign-insulfonate and 1 part by weight of sodium oleoylmethyltaurinate as wetting and dispersing agent, and grinding in a pinned disk mill.
c) A dispersion concentrate which is easily dispersible in water is prepared by mixing 40 parts by weight of active substance with 7 parts by weight of a sulfosuccinic monoester, 2 parts by weight of a sodium ligninsulfonate and 51 parts by weight of water and grinding in a ball mill to a fineness of below 5 microns.
d) An emulsifiable concentrate can be prepared from 15 parts by weight of active substance, 75 parts by weight of cyclohexane as solvent and 10 parts by weight of ethoxylated nonylphenol (10 EO) as emulsifier.
e) Granules can be prepared from 2 to 15 parts by weight of active substance and an inert granule carrier material such as attapulgite, granulated pumice and/or quartz sand. It is advantageous to use a suspension of the wettable powder of Example b) with a solids content of 30% which is sprayed onto the surface of attapulgite granules which are then dried and intimately mixed. The proportion by weight of the wettable powder in this case is about 5% and that of the inert carrier material is about 95% of the finished granules.

B. PREPARATION EXAMPLES

Example 1

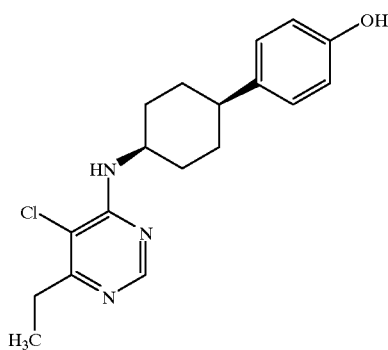

5-Chloro-6-ethyl-4-[cis-4-(4-hydroxy) phenylcyclohexylamino]pyrimidine 9.3 g 4,5-dichloro-6-ethylpyrimidine, 10 g cis-4-(4-hydroxyphenylcyclohexylamine and 15 ml triethylamine were heated in 100 ml dimethylformamide at 80° C. for 7 hours. The mixture was poured into water and stirred for 0.5 hours at 25° C. The resulting crystals were separated, washed once with a small amount of cold ethyl acetate and dried in vacuo to give the title product, m.p. 228° C. (compound 1).

Example 2

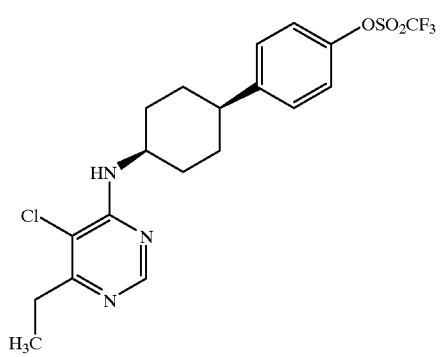

5-Chloro-6-ethyl-4-[cis-4-(4-trifluoromethylsulfonyloxy) phenylcyclohexylamino]-pyrimidine 1.36 g triethylamine were added at 10° C. to a solution of 3.00 g of compound 1 and 3.3 g trifluoromethanesulfonic acid anhydride in 30 ml of dichloromethane. The reaction mixture was stirred for 4 hours at 25° C. and then quenched with water. The organic layer was dried with sodium sulfate and the solvent was removed under reduced pressure. Chromatography (silica gel, ethyl acetate) gave the title product as a yellowish oil (compound 2).

Example 3

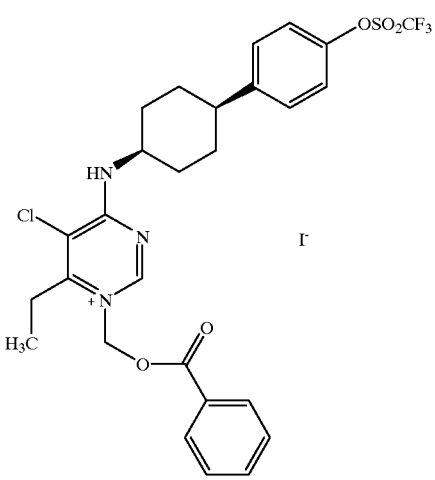

5-Chloro-6-ethyl-4-[cis-4-(4-trifluoromethylsulfonyloxy)phenylcyclohexylamino]-1-(benzoyloxymethyl)pyrimidinium iodide 0.7 g of compound 2, 0.3 g of chloromethyl benzoate and 0.23 g of sodium iodide in 20 ml of acetonitrile were heated under reflux for 12 hours. The reaction mixture was diluted with dichloromethane and washed with water. The organic layer was dried with sodium sulfate and the solvent removed. Chromatography (silica gel, ethyl acetate/methanol) gave the title product, m.p. 184° C. (Compound 3)

Example 4

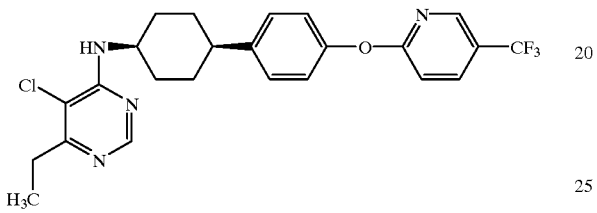

5-Chloro-6-ethyl-4-[cis4-[4-(5-trifluoromethylpyrid-2-yloxy)phenyl]-cyclohexylamino]pyrimidine 3.5 g 4,5-dichloro-6-ethyl-pyrimidine, 6.7 g 4-(5-trifluoromethyl-pyrid-2-yloxy)phenyl]cyclohexylamine and 3.0 g triethylamine were heated without solvent at 80–90° C. for 6 hours. The mixture was taken up in water/dichloromethane and the organic phase was dried and concentrated. For purification and for the separation of the cis/trans isomers, the residue was chromatographed over silica gel with ethyl acetate/petroleum ether (7:3), to give the title product, m.p. 114–6° C.). (Compound 4)

Preparation of the Starting Materials

4-(5-trifluoromethylpyrid-2-yloxy)phenyl]cyclohexylamine 33.5 g 4-(5-trifluoromethylpyrid-2-yloxy)phenyl] cyclohexanone and 38.5 g ammonium acetate were dissolved in 350 ml of methanol and stirred for 30 minutes. 31.4 g sodium cyanoborohydride was added portionwise at 0° C. The mixture was stirred at room temperature for 24 hours. The mixture was concentrated and the residue was taken up in toluene/dilute sodium hydroxide solution. The organic phase was dried and concentrated, to give the title product as a yellow oil, which was reacted without further purification.

4-(5-trifluoromethylpyridine-2-yloxy)phenyl]cyclohexylamine

To a suspension of 9.0 g sodium hydride (80% dispersion in mineral oil) in 300 ml of dimethylformamide was added, with cooling, a solution of 54 g 4-(4-hydroxyphenylcyclohexanone. After stirring for 30 minutes at room temperature, a solution of 54.3 g 5-trifluoromethyl-2-chloropyridine in 100 ml of dimethylformamide was added and the mixture was reheated at 90° C. for 6 hours. The mixture was concentrated and taken up in toluene/water. The toluene layer was washed twice with water, dried and concentrated. Recrystallisation of the solid residue from methanol gave the title product, m.p. 81–3° C.

The compounds of the tables below are obtained in a similar manner to one of to Examples 1 to 4.

TABLE 1

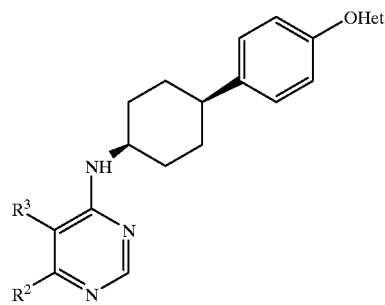

| Cmp | Het | R² | R³ | m.p./° C. |
|---|---|---|---|---|
| 5 | 3,5-diCl-2-pyridyl | Et | Cl | 121–122 |
| 6 | 5-CF₃-2-pyridyl | —CH₂OMe | MeO | oil |
| 7 | 6-MeO-pyridazin-3-yl | —CH₂OMe | MeO | 135 |
| 8 | pyrimidin-2-yl | Et | Cl | 137 |
| 9 | 6-MeO-pyridazin-3-yl | Et | Cl | resin |
| 10 | 3,6-diMe-pyrazin-2-yl | Et | Cl | 163–165 |
| 11 | 2,6-diMeO-pyrimidin-4-yl | Et | Cl | resin |
| 12 | 5-Cl-6-Et-pyrimidin-4-yl | Et | Cl | resin |

TABLE 2

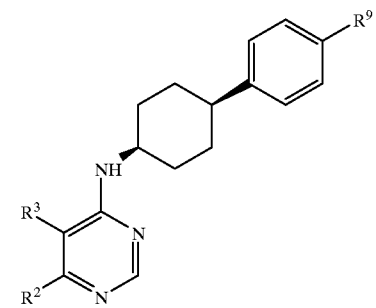

| Cmp | R² | R³ | R⁹ | m.p./° C. |
|---|---|---|---|---|
| 13 | Et | Br | —OSO₂Me | resin |
| 14 | Et | Br | OH | resin |
| 15 | Cl | Br | —OSO₂Me | 227–228 |
| 16 | Cl | Br | OH | 227–228 |

TABLE 3

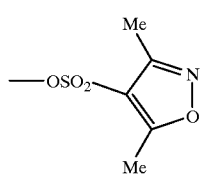

| Cmp | R¹ | R² | R³ | R⁹ | m.p./° C. |
|---|---|---|---|---|---|
| 17 | H | Et | Cl | —OSO₂Me | wax |
| 18 | H | Et | Cl | —OSO₂-p-tolyl | 152 |
| 19 | H | Et | H | OH | 88 |
| 20 | H | Et | Cl | —OC(=O)CH₂-(4-PhO-phenyl) | oil |
| 21 | H | Et | Cl | pyrrolidinecarbonyloxy | wax |
| 22 | H | Me | Cl | OH | 220 |
| 23 | Cl | Et | Cl | OH | 173 |
| 24 | H | Et | Cl | —OC(=O)Me | 68 |
| 25 | H | Et | Cl | —OC(=O)NPrⁱ₂ | oil |
| 26 | H | Et | Cl | morpholinecarbonyloxy | 124 |
| 27 | H | Et | Cl | phenacyloxy | 147 |
| 28 | H | Et | Cl | —OC(=O)OEt | 102 |
| 29 | Me | Et | Cl | —OSO₂CF₃ | oil |
| 30 | Me | Et | Cl | —OSO₂Me | oil |
| 31 | H | Et | Cl | —OC(=O)NHMe | 107 |
| 32 | H | Et | Cl | —OC(=O)OMe | wax |
| 33 | H | Et | Cl | phenylsulfonyloxy | oil |
| 34 | H | Et | Cl | 4-F-phenylsulfonyloxy | wax |
| 35 | H | Et | Cl | 4-Cl-phenylsulfonyloxy | wax |
| 36 | H | Et | Cl | 2-Cl-phenylsulfonyloxy | wax |
| 37 | H | Et | Cl | 4-tBu-phenylsulfonyloxy | 84 |
| 38 | H | Et | Cl | ethylsufonyloxy | |
| 39 | H | Et | Cl | 4-(acetamido)phenylsulfonyloxy | |
| 40 | H | Et | Cl | 2,4-diCl-phenylsulfonyloxy | oil |
| 41 | H | Et | Cl | 3,4-diMeO-phenylsulfonyloxy | |
| 42 | H | Et | Cl | 4-MeO-phenylsulfonyloxy | 156–9 |
| 43 | H | Et | Cl | 2-CF₃-phenylsulfonyloxy | oil |
| 44 | H | Et | Cl | 3-Cl-4-Me-phenylsulfonyloxy | oil |
| 45 | H | Et | Cl | 3-NO₂-4-Me-phenylsulfonyloxy | |
| 46 | H | Et | Cl | propylsulfonyloxy | oil |
| 47 | H | Et | Cl | 3-NO₂-phenylsulfonyloxy | wax |
| 48 | H | Et | Cl | 4-NO₂-phenylsulfonyloxy | 128–34 |
| 49 | H | Et | Cl | 2-NO₂-phenylsulfonyloxy | wax |
| 50 | H | Et | Cl | 4-I-phenylsulfonyloxy | oil |
| 51 | H | Et | Cl | isopropylsulfonyloxy | |
| 52 | H | Et | Cl | 2-CF₃O-phenylsulfonyloxy | oil |
| 53 | H | Et | Cl | —OSO₂CCl₃ | |
| 54 | H | Et | Cl | —OSO₂CCl₂ | |
| 55 | H | Et | Cl | butylsulfonyloxy | |
| 56 | H | Et | Cl | benzylsulfonyloxy | |
| 57 | H | Et | Cl | octylsulfonyloxy | |
| 58 | H | Et | Cl | 2-NO₂-benzylsulfonyloxy | |
| 59 | H | Et | Cl | 5-Br-2-thienylsulfonyloxy | |
| 60 | H | Et | Cl | 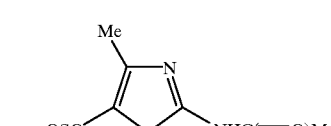 | |
| 61 | H | Et | Cl | —OSO₂NMe₂ | |
| 62 | H | Et | Cl |  | |

TABLE 3-continued

| Cmp | R¹ | R² | R³ | R⁹ | m.p./° C. |
|---|---|---|---|---|---|
| 63 | H | Et | Cl | —OP(O)Me₂ | |
| 64 | H | Et | Cl | —OP(O)Et₂ | |
| 65 | H | Et | Cl | —OP(O)Ph₂ | |
| 66 | H | Et | Cl | —OP(O)(Me)Ph | |
| 67 | H | Et | Cl | —OP(O)(cyclohexyl)₂ | |
| 68 | H | Et | Cl | —OP(O)(methoxy)₂ | |
| 69 | H | Et | Cl | —OP(O)(ethoxy)₂ | |
| 70 | H | Et | Cl | —OP(O)(propoxy)₂ | |
| 71 | H | Et | Cl | —OP(O)(isopropoxy)₂ | |
| 72 | H | Et | Cl | —OP(O)(butoxy)₂ | |
| 73 | H | Et | Cl | —OP(O)(pentoxy)₂ | |
| 74 | H | Et | Cl | —OP(O)(phenoxy)₂ | |
| 75 | H | Et | Cl | —OP(O)(4-Cl-phenoxy)₂ | |
| 76 | H | Et | Cl | —OP(O)(4-toloxy)₂ | |
| 77 | H | Et | Cl | —OP(O)(NMe₂)₂ | |
| 78 | H | Et | Cl | —OP(O)(NEt₂)₂ | |
| 79 | H | Et | Cl | —OP(O)(NPrⁱ₂)₂ | |
| 80 | H | Et | Cl | —OP(O)(NHPh)₂ | |
| 81 | H | Et | Cl | —OP(O)(NHPh)(OPh) | |
| 82 | H | Et | Cl | —OP(S)Me₂ | |
| 83 | H | Et | Cl | —OP(S)Et₂ | |
| 84 | H | Et | Cl | —OP(S)Ph₂ | |
| 85 | H | Et | Cl | —OP(S)(Me)Ph | |
| 86 | H | Et | Cl | —OP(S)(OMe)₂ | |
| 87 | H | Et | Cl | —OP(S)(OEt)₂ | |
| 88 | H | Et | Cl | —OP(S)(OPr)₂ | |
| 89 | H | Et | Cl | —OP(S)(OBu)₂ | |
| 90 | H | Et | Cl | —OP(S)(NMe₂)₂ | |
| 91 | H | Et | Cl | 2,4,5-triCl-phenylsulfonyloxy | wax |
| 92 | H | Et | Cl | 2-MeO—NO₂-phenylsulfonyloxy | oil |
| 93 | H | Et | Cl | 2,4,6-triMe-phenylsulfonyloxy | wax |
| 94 | H | Et | Cl | 3,4-diCl-phenylsulfonyloxy | oil |
| 95 | H | Et | Cl | 3,6-diCl-phenylsulfonyloxy | oil |
| 96 | H | Et | Cl | 3-NO₂-6-Me-phenylsulfonyloxy | oil |
| 97 | H | Et | Cl | 1-naphthylsulfonyloxy | wax |
| 98 | H | Et | Cl | 4-Br-phenylsulfonyloxy | wax |
| 99 | H | Et | Cl | 3-CF₃-phenylsulfonyloxy | oil |
| 100 | H | Et | Cl | 2-Br-phenylsulfonyloxy | oil |
| 101 | H | Et | Cl | 3-Cl-phenylsulfonyloxy | oil |
| 102 | H | Et | Cl | 4-Cl-2,5-diMe-phenylsulfonyloxy | oil |
| 103 | H | Et | Cl | 2-CF₃-phenylsulfonyloxy | wax |
| 104 | H | Et | Cl | 2,4-diF-phenylsulfonyloxy | oil |
| 105 | H | Et | Cl | 4-Pr-phenylsulfonyloxy | oil |
| 106 | H | Et | Cl | 4-Prⁱ-phenylsulfonyloxy | oil |
| 107 | H | Et | Cl | 2-Br-phenylsulfonyloxy | oil |
| 108 | H | Et | Cl | 2-naphthylsulfonyloxy | oil |
| 109 | H | Et | Cl | 3-Cl-2-NO₂-phenylsulfonyloxy | oil |
| 110 | H | Et | Cl | 2-NO₂-4-CF₃-phenylsulfonyloxy | 141–3 |
| 111 | H | Et | Cl | 3,5-diCl-phenylsulfonyloxy | oil |
| 112 | H | Et | Cl | 4-MeO-2,3,6-triMe-phenylsulfonyloxy | oil |
| 113 | H | Et | Cl | 3-Me-phenylsulfonyloxy | oil |
| 114 | H | Et | Cl | 5-F-2-Me-phenylsulfonyloxy | oil |
| 114 | H | Et | Cl | penta-F-phenylsulfonyloxy | oil |
| 115 | H | Et | Cl | 2-F-phenylsulfonyloxy | oil |
| 116 | H | Et | Cl | 4-Prⁱ-phenylsulfonyloxy | oil |
| 117 | H | Et | Cl | 2,4-diF-anilinocarbonyloxy | wax |
| 118 | H | Et | Cl | 3,5-di CF₃-phenylsulfonyloxy | oil |

TABLE 3-continued

| Cmp | R¹ | R² | R³ | R⁹ | m.p./° C. |
|---|---|---|---|---|---|
| 119 | H | Et | Cl | | oil |
| 120 | H | Et | Cl | 3-Cl-2-Me-phenylsulfonyloxy | oil |
| 121 | H | Et | Cl | 2,3-diCl-phenylsulfonyloxy | oil |
| 122 | H | Et | Cl | 2,4,6-triCl-phenylsulfonyloxy | oil |
| 123 | H | Et | Cl | 4-(1,1-diMe-propyl)-phenylsulfonyloxy | 92–4 |
| 124 | H | Et | Cl | 2-Cl-4-F-phenylsulfonyloxy | wax |
| 125 | H | Et | Cl | 4-Br-2,5-diF-phenylsulfonyloxy | wax |
| 126 | H | Et | Cl | 2,5-di-MeO-phenylsulfonyloxy | wax |
| 127 | H | Et | Cl | 3-Br-phenylsulfonyloxy | wax |
| 128 | H | Et | Cl | 2,6-di-Cl-phenylsulfonyloxy | oil |
| 129 | H | Et | Cl | 2-cyanophenylsulfonyloxy | oil |
| 130 | H | Et | Cl | 2,3,4-tri-Cl-phenylsulfonyloxy | 97–9 |
| 131 | H | Et | Cl | 4-biphenylylsulfonyloxy | oil |
| 132 | H | Et | Cl | 2-MeO-anilinocarbonyloxy | oil |
| 133 | H | Et | Cl | 2,4-di-MeO-anilinocarbonyloxy | 149 |
| 135 | H | Et | Cl | 3-F-anilinocarbonyloxy | wax |
| 136 | H | Et | Cl | N-cyclohexylcarbamoyloxy | 118–22 |
| 137 | H | Et | Cl | 2-NO₂-anilinocarbonyloxy | 189 |
| 138 | H | Et | Cl | 2-MeOCO-anilinocarbonyloxy | wax |
| 139 | H | Et | Cl | 4-MeS-anilinocarbonyloxy | 148–52 |
| 140 | H | Et | Cl | 2-Ph-anilinocarbonyloxy | 196–204 |
| 141 | H | Et | Cl | N-[1-(1-naphthyl)ethyl]-carbamoyloxy | wax |
| 142 | H | Et | Cl | N-[3-(tri-EtO-Si)propyl]-carbamoyloxy | wax |
| 143 | H | Et | Cl | 4-CF₃O-anilinocarbonyloxy | wax |
| 144 | H | Et | Cl | N-Bu-carbamoyloxy | 90–1 |
| 145 | H | Et | Cl | N-Prⁱ-carbamoyloxy | wax |
| 146 | H | Et | Cl | N-(2-chloroethyl)carbamoyloxy | oil |
| 147 | H | Et | Cl | 2-F-anilinocarbonyloxy | wax |
| 148 | H | Et | Cl | 2,3-diCl-anilinocarbonyloxy | wax |
| 149 | H | Et | Cl | 3-Cl-4-F-phenylsulfonyloxy | oil |
| 150 | H | Et | Cl | 4-Et-phenylsulfonyloxy | oil |
| 151 | H | Et | Cl | pivaloyloxy | oil |
| 152 | H | Et | Cl | benzoyloxy | 123–6 |
| 153 | H | Et | Cl | isobutyryloxy | 61 |
| 154 | H | Et | Cl | 2,4-diCl-benzoyloxy | wax |
| 155 | H | Et | Cl | 3-F-benzoyloxy | wax |
| 156 | H | Et | Cl | 2-furoyloxy | wax |
| 157 | H | Et | Cl | 2-Cl-benzoyloxy | wax |
| 158 | H | Et | Cl | —OCOCH(Me)Et | oil |
| 159 | H | Et | Cl | isovaleryloxy | oil |
| 160 | H | Et | Cl | cyclohexylcarbonyloxy | oil |
| 161 | H | Et | Cl | 2-(MeOCO)-benzoyloxy | oil |
| 162 | H | Et | Cl | 3,4-diCl-benzoyloxy | wax |
| 163 | H | Et | Cl | 4-Cl-nicotinyloxy | oil |
| 164 | H | Et | Cl | cyclopentylcarbonyloxy | oil |
| 165 | H | Et | Cl | 2-phenylbutyryloxy | oil |
| 166 | H | Et | Cl | 4-F-benzoyloxy | wax |
| 167 | H | Et | Cl | valeryloxy | oil |
| 168 | H | Et | Cl | 2-thenoyloxy | wax |
| 169 | H | Et | Cl | propionyloxy | oil |
| 170 | H | Et | Cl | 3-Cl-benzoyloxy | oil |

For compound 119, R⁹ = —OSO₂-(7-position of 2-(trifluoroacetyl)-1,2,3,4-tetrahydroisoquinolin-7-yl)

TABLE 3-continued

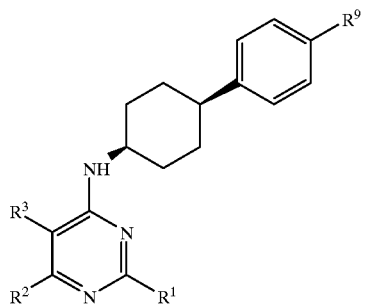

| Cmp | R¹ | R² | R³ | R⁹ | m.p./° C. |
|---|---|---|---|---|---|
| 171 | H | Et | Cl | 4-Cl-benzoyloxy | wax |
| 172 | H | Et | Cl | 2-Me-benzoyloxy | wax |
| 173 | H | Et | Cl | 2,3-diCl-benzoyloxy | wax |
| 174 | H | Et | Cl | 4-CF₃-benzoyloxy | oil |
| 175 | H | Et | Cl | 2-F-benzoyloxy | wax |
| 176 | H | Et | Cl | 2,6-diF-benzoyloxy | wax |
| 177 | H | Et | Cl | 4-Me-benzoyloxy | wax |
| 178 | H | Et | Cl | 2,4-diF-benzoyloxy | wax |
| 179 | H | Et | Cl | 2-MeO-benzoyloxy | oil |
| 180 | H | Et | Cl | 4-Br-benzoyloxy | wax |
| 181 | H | Et | Cl | 4-Buᵗ-benzoyloxy | oil |
| 182 | H | Et | Cl | 2-Cl-4-NO₂-benzoyloxy | oil |
| 183 | H | Et | Cl | 2-Cl-5-NO₂-benzoyloxy | wax |
| 184 | H | Et | Cl | 2-Cl-4-F-benzoyloxy | oil |
| 185 | H | Et | Cl | 3,5-diF-benzoyloxy | wax |
| 186 | H | Et | Cl | hexanoyloxy | oil |
| 187 | H | Et | Cl | cyclopropanylcarbonyloxy | oil |
| 188 | H | Et | Cl | methoxyacetyloxy | wax |
| 189 | H | Et | Cl | palmitoyloxy | wax |
| 190 | H | Et | Cl | 3-CF₃-benzoyloxy | oil |
| 191 | H | Et | Cl | butyryloxy | oil |
| 192 | H | Et | Cl | 2,5-diF-benzoyloxy | wax |
| 193 | H | Et | Cl | 1-naphthoyloxy | wax |
| 194 | H | Et | Cl | 2-naphthoyloxy | wax |
| 195 | H | Et | Cl | 4-I-benzoyloxy | oil |
| 196 | H | Et | Cl | cinnamoyloxy | solid |
| 197 | H | Et | Cl | methacryolyl | wax |

TABLE 4

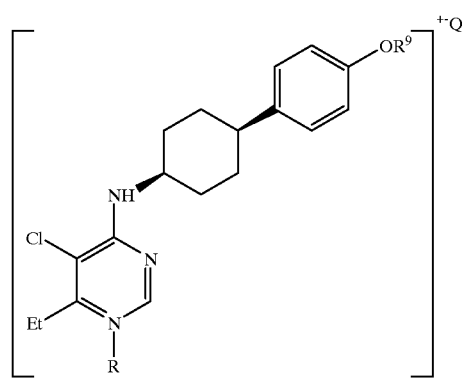

| Cmp | R⁹ | Q | R | m.p./° C. |
|---|---|---|---|---|
| 500 | —OSO₂CF₃ | Br | —CH₂C(=O)-p-phenylene-OC(=O)Ph | >200 |
| 501 | —OSO₂Me | Br | —CH₂C(=O)-p-phenylene-OC(=O)Ph | >200 |
| 502 | —OSO₂Me | I | —CH₂OC(=O)Ph | 98 |
| 503 | —OSO₂CF₃ | Br | —CH₂C(=O)-p-phenylene-OC(=O)Buᵗ | |
| 504 | —OSO₂Me | Br | —CH₂C(=O)-p-phenylene- | |

TABLE 4-continued

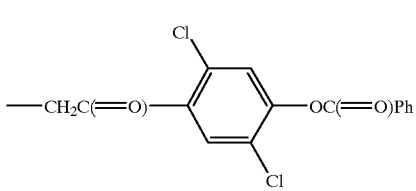

| Cmp | R⁹ | Q | R | m.p./° C. |
|---|---|---|---|---|
| | | | OC(=O)Buᵗ | |
| 505 | —OSO$_2$CF$_3$ | Br | —CH$_2$C(=O)-p-phenylene-OC(=O)Prⁱ | |
| 506 | —OSO$_2$Me | Br | —CH$_2$C(=O)-p-phenylene-OC(=O)Prⁱ | |
| 507 | —OSO$_2$CF$_3$ | Br | —CH$_2$C(=O)-o-phenylene-OC(=O)Ph | |
| 508 | —OSO$_2$Me | Br | —CH$_2$C(=O)-o-phenylene-OC(=O)Ph | |
| 509 | —OSO$_2$CF$_3$ | I | —CH$_2$O(C=O)Buᵗ | |
| 510 | —OSO$_2$Me | I | —CH$_2$O(C=O)Buᵗ | |
| 511 | —OSO$_2$CF$_3$ | Br | 4-(propionyloxy)benzyl | |
| 512 | —OSO$_2$Me | Br | 4-(propionyloxy)benzyl | |
| 513 | —OSO$_2$CF$_3$ | Br | 2-(ethoxycarbonyloxy)benzyl | |
| 514 | —OSO$_2$Me | Br | 2-(ethoxycarbonyloxy)benzyl | |
| 515 | —OSO$_2$CF$_3$ | Br | —CH$_2$C(=O)-m-phenylene-OC(=O)Ph | |
| 516 | —OSO$_2$Me | Br | —CH$_2$C(=O)-m-phenylene-OC(=O)Ph | |
| 517 | —OSO$_2$CF$_3$ | Br | 4-(CF$_3$O-benzoyl)methyl | |
| 518 | —OSO$_2$Me | Br | 4-(CF$_3$O-benzoyl)methyl | |
| 519 | —OSO$_2$CF$_3$ | Br | 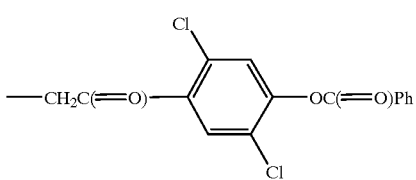 | |
| 520 | —OSO$_2$Me | Br | (same structure as 519) | |
| 521 | —OSO$_2$-p-tolyl | Br | —CH$_2$C(=O)-p-phenylene-OC(=O)Ph | |
| 522 | —OSO$_2$-p-tolyl | I | —CH$_2$OC(=O)Ph | |
| 523 | —OSO$_2$-p-tolyl | Br | —CH$_2$C(=O)-p-phenylene-OC(=O)Buᵗ | |
| 524 | —OSO$_2$-p-tolyl | Br | —CH$_2$C(=O)-p-phenylene-OC(=O)Prⁱ | |
| 525 | —OSO$_2$-p-tolyl | Br | —CH$_2$C(=O)-o-phenylene-OC(=O)Ph | |
| 526 | —OSO$_2$-p-tolyl | I | —CH$_2$O(C=O)Buᵗ | |
| 527 | —OSO$_2$-p-tolyl | Br | 4-(propionyloxy)benzyl | |
| 528 | —OSO$_2$-p-tolyl | Br | 2-(ethoxycarbonyloxy)benzyl | |
| 529 | —OSO$_2$-p-tolyl | Br | —CH$_2$C(=O)-m-phenylene-OC(=O)Ph | |
| 530 | —OSO$_2$-p-tolyl | Br | 4-(CF$_3$O-benzoyl)methyl | |

TABLE 4-continued

| Cmp | R⁹ | Q | R | m.p./° C. |
|---|---|---|---|---|
| 531 | —OSO₂-p-tolyl | Br | (3,5-dichloro-4-(PhC(=O)O)phenyl)C(=O)CH₂— | |
| 532 | OH | Br | —CH₂C(=O)-p-phenylene-OC(=O)Ph | |
| 533 | OH | I | —CH₂OC(=O)Ph | |
| 534 | OH | Br | —CH₂C(=O)-p-phenylene-OC(=O)Buᵗ | |
| 535 | OH | Br | —CH₂C(=O)-p-phenylene-OC(=O)Prⁱ | |
| 536 | OH | Br | —CH₂C(=O)-o-phenylene-OC(=O)Ph | |
| 537 | OH | I | —CH₂O(C=O)Buᵗ | |
| 538 | OH | Br | 4-(propionyloxy)benzyl | |
| 539 | OH | Br | 2-(ethoxycarbonyloxy)benzyl | |
| 540 | OH | Br | —CH₂C(=O)-m-phenylene-OC(=O)Ph | |
| 541 | OH | Br | 4-(CF₃O-benzoyl)methyl | |
| 542 | OH | Br | (3,5-dichloro-4-(PhC(=O)O)phenyl)C(=O)CH₂— | |
| 543 | —OC(=O)CH₂-(4-PhO-phenyl) | Br | —CH₂C(=O)-p-phenylene-OC(=O)Ph | |
| 544 | —OC(=O)CH₂-(4-PhO-phenyl) | I | —CH₂OC(=O)Ph | |
| 545 | —OC(=O)CH₂-(4-PhO-phenyl) | Br | —CH₂C(=O)-p-phenylene-OC(=O)Buᵗ | |
| 546 | —OC(=O)CH₂-(4-PhO-phenyl) | Br | —CH₂C(=O)-p-phenylene-OC(=O)Prⁱ | |
| 547 | —OC(=O)CH₂-(4-PhO-phenyl) | Br | —CH₂C(=O)-o-phenylene-OC(=O)Ph | |
| 548 | —OC(=O)CH₂-(4-PhO-phenyl) | I | —CH₂O(C=O)Buᵗ | |
| 549 | —OC(=O)CH₂-(4-PhO-phenyl) | Br | 4-(propionyloxy)benzyl | |
| 550 | —OC(=O)CH₂-(4-PhO-phenyl) | Br | 2-(ethoxycarbonyloxy)benzyl | |
| 551 | —OC(=O)CH₂-(4-PhO-phenyl) | Br | —CH₂C(=O)-m-phenylene-OC(=O)Ph | |
| 552 | —OC(=O)CH₂-(4-PhO-phenyl) | Br | 4-(CF₃O-benzoyl)methyl | |

TABLE 4-continued

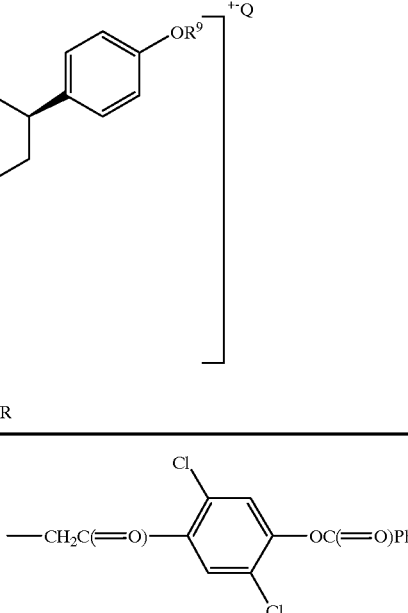

| Cmp | R⁹ | Q | R | m.p./° C. |
|---|---|---|---|---|
| 553 | —OC(=O)CH₂-(4-PhO-phenyl) | Br | 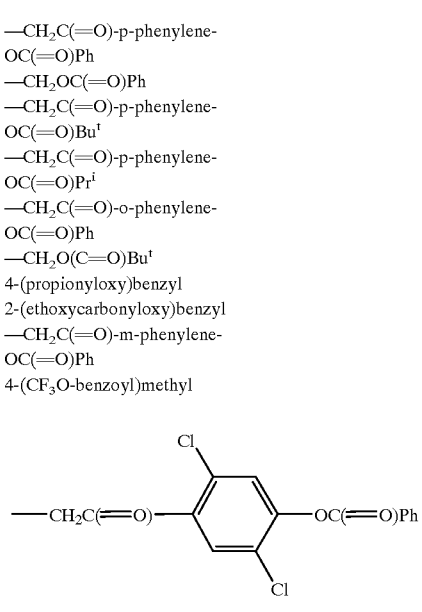 | |
| 554 | pyrrolidinecarbonyloxy | Br | —CH₂C(=O)-p-phenylene-OC(=O)Ph | |
| 555 | pyrrolidinecarbonyloxy | I | —CH₂OC(=O)Ph | |
| 556 | pyrrolidinecarbonyloxy | Br | —CH₂C(=O)-p-phenylene-OC(=O)Buᵗ | |
| 557 | pyrrolidinecarbonyloxy | Br | —CH₂C(=O)-p-phenylene-OC(=O)Prⁱ | |
| 558 | pyrrolidinecarbonyloxy | Br | —CH₂C(=O)-o-phenylene-OC(=O)Ph | |
| 559 | pyrrolidinecarbonyloxy | I | —CH₂O(C=O)Buᵗ | |
| 560 | pyrrolidinecarbonyloxy | Br | 4-(propionyloxy)benzyl | |
| 561 | pyrrolidinecarbonyloxy | Br | 2-(ethoxycarbonyloxy)benzyl | |
| 562 | pyrrolidinecarbonyloxy | Br | —CH₂C(=O)-m-phenylene-OC(=O)Ph | |
| 563 | pyrrolidinecarbonyloxy | Br | 4-(CF₃O-benzoyl)methyl | |
| 564 | pyrrolidinecarbonyloxy | Br | 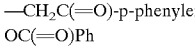 | |
| 565 | —OC(=O)Me | Br | —CH₂C(=O)-p-phenylene-OC(=O)Ph | |
| 566 | —OC(=O)Me | I | —CH₂OC(=O)Ph | |
| 567 | —OC(=O)Me | Br | —CH₂C(=O)-p-phenylene-OC(=O)Buᵗ | |
| 568 | —OC(=O)Me | Br | —CH₂C(=O)-p-phenylene-OC(=O)Prⁱ | |
| 569 | —OC(=O)Me | Br | —CH₂C(=O)-o-phenylene-OC(=O)Ph | |
| 570 | —OC(=O)Me | I | —CH₂O(C=O)Buᵗ | |
| 571 | —OC(=O)Me | Br | 4-(propionyloxy)benzyl | |
| 572 | —OC(=O)Me | Br | 2-(ethoxycarbonyloxy)benzyl | |
| 573 | —OC(=O)Me | Br | —CH₂C(=O)-m-phenylene-OC(=O)Ph | |
| 574 | —OC(=O)Me | Br | 4-(CF₃O-benzoyl)methyl | |

TABLE 4-continued

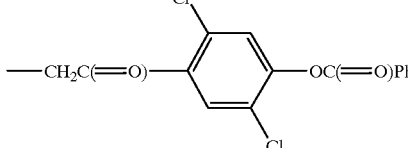

| Cmp | R⁹ | Q | R | m.p./° C. |
|---|---|---|---|---|
| 575 | —OC(=O)Me | Br | 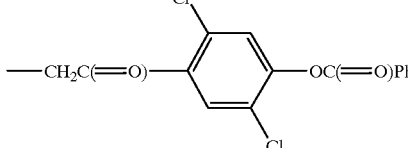 | |
| 576 | —OC(=O)NPr$^i_2$ | Br | —CH$_2$C(=O)-p-phenylene-OC(=O)Ph | |
| 577 | —OC(=O)NPr$^i_2$ | I | —CH$_2$OC(=O)Ph | |
| 578 | —OC(=O)NPr$^1_2$ | Br | —CH$_2$C(=O)-p-phenylene-OC(=O)Bu$^t$ | |
| 579 | —OC(=O)NPr$^i_2$ | Br | —CH$_2$C(=O)-p-phenylene-OC(=O)Pr$^i$ | |
| 580 | —OC(=O)NPr$^i_2$ | Br | —CH$_2$C(=O)-o-phenylene-OC(=O)Ph | |
| 581 | —OC(=O)NPr$^i_2$ | I | —CH$_2$O(C=O)Bu$^t$ | |
| 582 | —OC(=O)NPr$^i_2$ | Br | 4-(propionyloxy)benzyl | |
| 583 | —OC(=O)NPr$^i_2$ | Br | 2-(ethoxycarbonyloxy)benzyl | |
| 584 | —OC(=O)NPr$^i_2$ | Br | —CH$_2$C(=O)-m-phenylene-OC(=O)Ph | |
| 585 | —OC(=O)NPr$^i_2$ | Br | 4-(CF$_3$O-benzoyl)methyl | |
| 586 | —OC(=O)NPr$^i_2$ | Br | 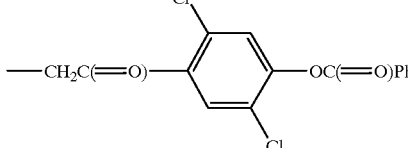 | |
| 587 | morpholinecarbonyloxy | Br | —CH$_2$C(=O)-p-phenylene-OC(=O)Ph | |
| 588 | morpholinecarbonyloxy | I | —CH$_2$OC(=O)Bu$^t$ | |
| 589 | morpholinecarbonyloxy | Br | —CH$_2$C(=O)-p-phenylene-OC(=O)Bu$^t$ | |
| 590 | morpholinecarbonyloxy | Br | —CH$_2$C(=O)-p-phenylene-OC(=O)Pr$^i$ | |
| 591 | morpholinecarbonyloxy | Br | —CH$_2$C(=O)-o-phenylene-OC(=O)Ph | |
| 592 | morpholinecarbonyloxy | I | —CH$_2$O(C=O)Bu$^t$ | |
| 593 | morpholinecarbonyloxy | Br | 4-(propionyloxy)benzyl | |
| 594 | morpholinecarbonyloxy | Br | 2-(ethoxycarbonyloxy)benzyl | |
| 595 | morpholinecarbonyloxy | Br | —CH$_2$C(=O)-m-phenylene-OC(=O)Ph | |
| 596 | morpholinecarbonyloxy | Br | 4-(CF$_3$O-benzoyl)methyl | |

TABLE 4-continued

| Cmp | R⁹ | Q | R | m.p./° C. |
|---|---|---|---|---|
| 597 | morpholinecarbonyloxy | Br | —CH₂C(=O)-(2,5-dichloro-4-(OC(=O)Ph)phenyl) | |
| 598 | phenacyloxy | Br | —CH₂C(=O)-p-phenylene-OC(=O)Ph | |
| 599 | phenacyloxy | I | —CH₂OC(=O)Ph | |
| 600 | phenacyloxy | Br | —CH₂C(=O)-p-phenylene-OC(∇O)Buᵗ | |
| 601 | phenacyloxy | Br | —CH₂C(=O)-p-phenylene-OC(=O)Prⁱ | |
| 602 | phenacyloxy | Br | —CH₂C(=O)-o-phenylene-OC(=O)Ph | |
| 603 | phenacyloxy | I | —CH₂O(C=O)Buᵗ | |
| 604 | phenacyloxy | Br | 4-(propionyloxy)benzyl | |
| 605 | phenacyloxy | Br | 2-(ethoxycarbonyloxy)benzyl | |
| 606 | phenacyloxy | Br | —CH₂C(=O)-m-phenylene-OC(=O)Ph | |
| 607 | phenacyloxy | Br | 4-(CF₃O-benzoyl)methyl | |
| 608 | phenacyloxy | Br | —CH₂C(=O)-(2,5-dichloro-4-(OC(=O)Ph)phenyl) | |
| 609 | —OC(=O)OEt | Br | —CH₂C(=O)-p-phenylene-OC(=O)Ph | |
| 610 | —OC(=O)OEt | I | —CH₂OC(=O)Ph | |
| 611 | —OC(=O)OEt | Br | —CH₂C(=O)-phenylene-OC(=O)Buᵗ | |
| 612 | —OC(=O)OEt | Br | —CH₂C(=O)-p-phenylene-OC(=O)Prⁱ | |
| 613 | —OC(=O)OEt | Br | —CH₂C(=O)-o-phenylene-OC(=O)Ph | |
| 614 | —OC(=O)OEt | I | —CH₂O(C=O)Buᵗ | |
| 615 | —OC(=O)OEt | Br | 4-(propionyloxy)benzyl | |
| 616 | —OC(=O)OEt | Br | 2-(ethoxycarbonyloxy)benzyl | |
| 617 | —OC(=O)OEt | Br | —CH₂C(=O)-m-phenylene-OC(=O)Ph | |
| 618 | —OC(=O)OEt | Br | 4-(CF₃O-benzoyl)methyl | |

TABLE 4-continued

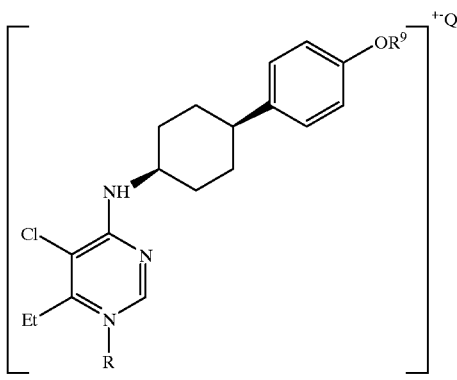

| Cmp | R⁹ | Q | R | m.p./° C. |
|---|---|---|---|---|
| 619 | —OC(=O)OEt | Br | 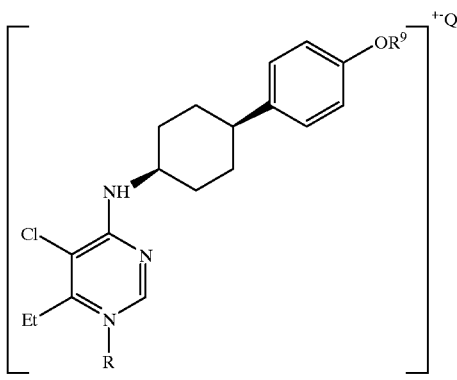 | |
| 620 | —OC(=O)NHMe | Br | —CH₂C(=O)-p-phenylene-OC(=O)Ph | |
| 621 | —OC(=O)NHMe | I | —CH₂OC(=O)Ph | |
| 622 | —OC(=O)NHMe | Br | —CH₂C(=O)-p-phenylene-OC(=O)Buᵗ | |
| 623 | —OC(=O)NHMe | Br | —CH₂C(=O)-p-phenylene-OC(=O)Prⁱ | |
| 624 | —OC(=O)NHMe | Br | —CH₂C(=O)-o-phenylene-OC(=O)Ph | |
| 625 | —OC(=O)NHMe | I | —CH₂O(C=O)Buᵗ | |
| 626 | —OC(=O)NHMe | Br | 4-(propionyloxy)benzyl | |
| 627 | —OC(=O)NHMe | Br | 2-(ethoxycarbonyloxy)benzyl | |
| 628 | —OC(=O)NHMe | Br | —CH₂C(=O)-m-phenylene-OC(=O)Ph | |
| 629 | —OC(=O)NHMe | Br | 4-(CF₃O-benzoyl)methyl | |
| 630 | —OC(=O)NHMe | Br | 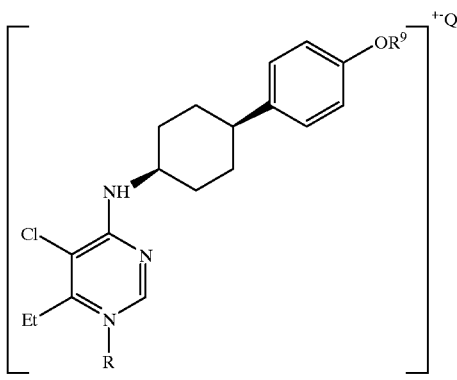 | |
| 631 | —OC(=O)OMe | Br | —CH₂C(=O)-p-phenylene-OC(=O)Ph | |
| 632 | —OC(=O)OMe | I | —CH₂OC(=O)Ph | |
| 633 | —OC(=O)OMe | Br | —CH₂C(=O)-p-phenylene-OC(=O)Buᵗ | |
| 634 | —OC(=O)OMe | Br | —CH₂C(=O)-p-phenylene-OC(=O)Prⁱ | |
| 635 | —OC(=O)OMe | Br | —CH₂C(=O)-o-phenylene-OC(=O)Ph | |
| 636 | —OC(=O)OMe | I | —CH₂O(C=O)Buᵗ | |
| 637 | —OC(=O)OMe | Br | 4-(propionyloxy)benzyl | |
| 638 | —OC(=O)OMe | Br | 2-(ethoxycarbonyloxy)benzyl | |
| 639 | —OC(=O)OMe | Br | —CH₂C(=O)-m-phenylene-OC(=O)Ph | |
| 640 | —OC(=O)OMe | Br | 4-(CF₃O-benzoyl)methyl | |

TABLE 4-continued

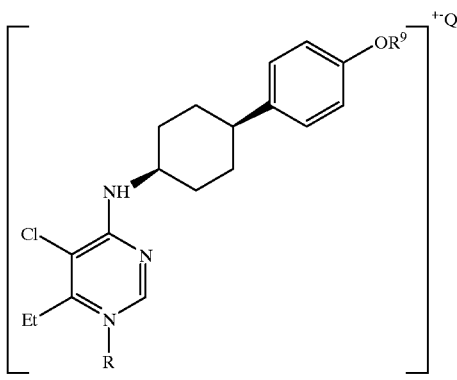

| Cmp | R⁹ | Q | R | m.p./° C. |
|---|---|---|---|---|
| 641 | —OC(=O)OMe | Br | 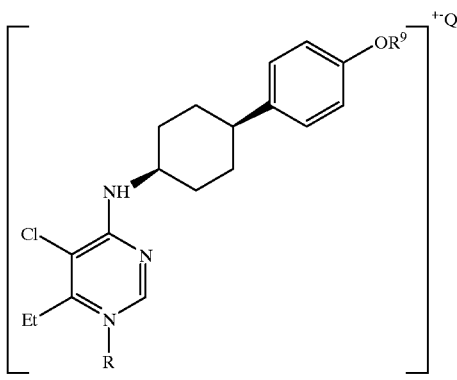 | |
| 642 | phenylsulfonyloxy | Br | —CH₂C(=O)-p-phenylene-OC(=O)Ph | |
| 643 | phenylsulfonyloxy | I | —CH₂OC(=O)Ph | |
| 644 | phenylsulfonyloxy | Br | —CH₂C(=O)-p-phenylene-OC(=O)Buᵗ | |
| 645 | phenylsulfonyloxy | Br | —CH₂C(=O)-p-phenylene-OC(=O)Prⁱ | |
| 646 | phenylsulfonyloxy | Br | —CH₂C(=O)-o-phenylene-OC(=O)Ph | |
| 647 | phenylsulfonyloxy | I | —CH₂O(C=O)Buᵗ | |
| 648 | phenylsulfonyloxy | Br | 4-(propionyloxy)benzyl | |
| 649 | phenylsulfonyloxy | Br | 2-(ethoxycarbonyloxy)benzyl | |
| 650 | phenylsulfonyloxy | Br | —CH₂C(=O)-m-phenylene-OC(=O)Ph | |
| 651 | phenylsulfonyloxy | Br | 4-(CF₃O-benzoyl)methyl | |
| 652 | phenylsulfonyloxy | Br | 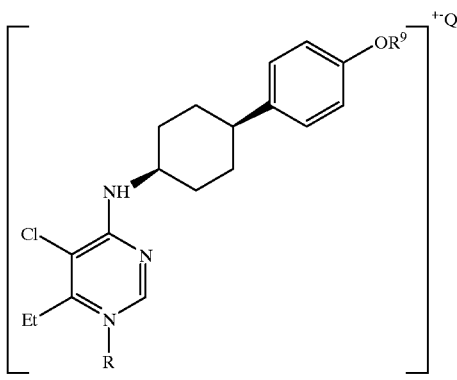 | |
| 653 | 4-F-phenylsulfonyloxy | Br | —CH₂C(=O)-p-phenylene-OC(=O)Ph | |
| 654 | 4-F-phenylsulfonyloxy | I | —CH₂OC(=O)Ph | |
| 655 | 4-F-phenylsulfonyloxy | Br | —CH₂C(=O)-p-phenylene-OC(=O)Buᵗ | |
| 656 | 4-F-phenylsulfonyloxy | Br | —CH₂C(=O)-p-phenylene-OC(=O)Prⁱ | |
| 657 | 4-F-phenylsulfonyloxy | Br | —CH₂C(=O)-o-phenylene-OC(=O)Ph | |
| 658 | 4-F-phenylsulfonyloxy | I | —CH₂O(C=O)Buᵗ | |
| 659 | 4-F-phenylsulfonyloxy | Br | 4-(propionyloxy)benzyl | |
| 660 | 4-F-phenylsulfonyloxy | Br | 2-(ethoxycarbonyloxy)benzyl | |
| 661 | 4-F-phenylsulfonyloxy | Br | —CH₂C(=O)-m-phenylene-OC(=O)Ph | |
| 662 | 4-F-phenylsulfonyloxy | Br | 4-(CF₃O-benzoyl)methyl | |

TABLE 4-continued

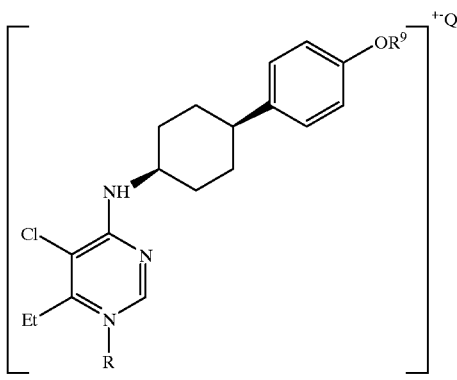

| Cmp | R⁹ | Q | R | m.p./° C. |
|---|---|---|---|---|
| 663 | 4-F-phenylsulfonyloxy | Br | 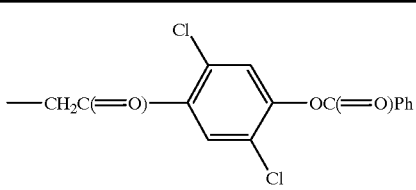 | |
| 664 | 4-Cl-phenylsulfonyloxy | Br | —CH₂C(=O)-p-phenylene-OC(=O)Ph | |
| 665 | 4-Cl-phenylsulfonyloxy | I | —CH₂OC(=O)Ph | |
| 666 | 4-Cl-phenylsulfonyloxy | Br | —CH₂C(=O)-p-phenylene-OC(=O)Bu$^t$ | |
| 667 | 4-Cl-phenylsulfonyloxy | Br | —CH₂C(=O)-p-phenylene-OC(=O)Pr$^i$ | |
| 668 | 4-Cl-phenylsulfonyloxy | Br | —CH₂C(=O)-o-phenylene-OC(=O)Ph | |
| 669 | 4-Cl-phenylsulfonyloxy | I | —CH₂O(C=O)Bu$^t$ | |
| 670 | 4-Cl-phenylsulfonyloxy | Br | 4-(propionyloxy)benzyl | |
| 671 | 4-Cl-phenylsulfonyloxy | Br | 2-(ethoxycarbonyloxy)benzyl | |
| 672 | 4-Cl-phenylsulfonyloxy | Br | —CH₂C(=O)-m-phenylene-OC(=O)Ph | |
| 673 | 4-Cl-phenylsulfonyloxy | Br | 4-(CF₃O-benzoyl)methyl | |
| 674 | 4-Cl-phenylsulfonyloxy | Br | 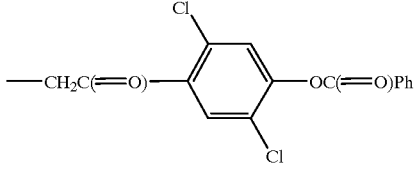 | |
| 675 | 2-Cl-phenylsulfonyloxy | Br | —CH₂C(=O)-p-phenylene-OC(=O)Ph | |
| 676 | 2-Cl-phenylsulfonyloxy | I | —CH₂OC(=O)Ph | |
| 677 | 2-Cl-phenylsulfonyloxy | Br | —CH₂C(=O)-p-phenylene-OC(=O)Bu$^t$ | |
| 678 | 2-Cl-phenylsulfonyloxy | Br | —CH₂C(=O)-p-phenylene-OC(=O)Pr$^i$ | |
| 679 | 2-Cl-phenylsulfonyloxy | Br | —CH₂C(=O)-o-phenylene-OC(=O)Ph | |
| 680 | 2-Cl-phenylsulfonyloxy | I | —CH₂O(C=O)Bu$^t$ | |
| 681 | 2-Cl-phenylsulfonyloxy | Br | 4-(propionyloxy)benzyl | |
| 682 | 2-Cl-phenylsulfonyloxy | Br | 2-(ethoxycarbonyloxy)benzyl | |
| 683 | 2-Cl-phenylsulfonyloxy | Br | —CH₂C(=O)-m-phenylene-OC(=O)Ph | |
| 684 | 2-Cl-phenylsulfonyloxy | Br | 4-(CF₃O-benzoyl)methyl | |

TABLE 4-continued

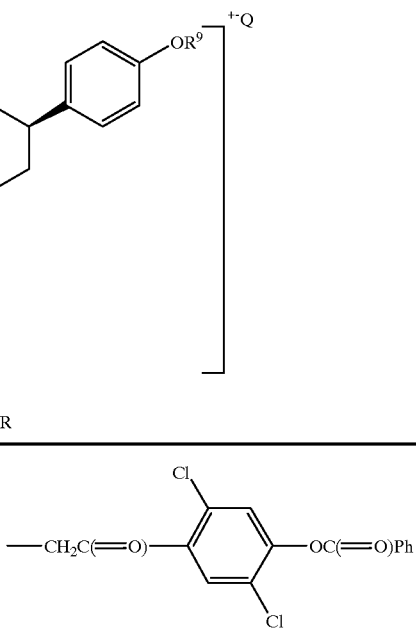

| Cmp | R⁹ | Q | R | m.p./° C. |
|---|---|---|---|---|
| 685 | 2-Cl-phenylsulfonyloxy | Br | 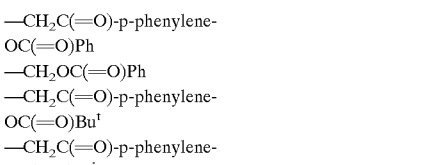 | |
| 686 | 4-tBu-phenylsulfonyloxy | Br | —CH$_2$C(=O)-p-phenylene-OC(=O)Ph | |
| 687 | 4-tBu-phenylsulfonyloxy | I | —CH$_2$OC(=O)Ph | |
| 688 | 4-tBu-phenylsulfonyloxy | Br | —CH$_2$C(=O)-p-phenylene-OC(=O)Bu$^t$ | |
| 689 | 4-tBu-phenylsulfonyloxy | Br | —CH$_2$C(=O)-p-phenylene-OC(=O)Pr$^i$ | |
| 690 | 4-tBu-phenylsulfonyloxy | Br | —CH$_2$C(=O)-o-phenylene-OC(=O)Ph | |
| 691 | 4-tBu-phenylsulfonyloxy | I | —CH$_2$O(C=O)Bu$^t$ | |
| 692 | 4-tBu-phenylsulfonyloxy | Br | 4-(propionyloxy)benzyl | |
| 693 | 4-tBu-phenylsulfonyloxy | Br | 2-(ethoxycarbonyloxy)benzyl | |
| 694 | 4-tBu-phenylsulfonyloxy | Br | —CH$_2$C(=O)-m-phenylene-OC(=O)Ph | |
| 695 | 4-tBu-phenylsulfonyloxy | Br | 4-(CF$_3$O-benzoyl)methyl | |
| 696 | 4-tBu-phenylsulfonyloxy | Br | 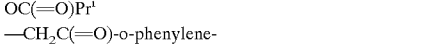 | |
| 697 | ethylsufonyloxy | Br | —CH$_2$C(=O)-p-phenylene-OC(=O)Ph | |
| 698 | ethylsufonyloxy | I | —CH$_2$OC(=O)Ph | |
| 699 | ethylsufonyloxy | Br | —CH$_2$C(=O)-p-phenylene-OC(=O)Bu$^t$ | |
| 700 | ethylsufonyloxy | Br | —CH$_2$C(=O)-p-phenylene-OC(=O)Pr$^i$ | |
| 701 | ethylsufonyloxy | Br | —CH$_2$C(=O)-o-phenylene-OC(=O)Ph | |
| 702 | ethylsufonyloxy | I | —CH$_2$O(C=O)Bu$^t$ | |
| 703 | ethylsufonyloxy | Br | 4-(propionyloxy)benzyl | |
| 704 | ethylsufonyloxy | Br | 2-(ethoxycarbonyloxy)benzyl | |
| 705 | ethylsufonyloxy | Br | —CH$_2$C(=O)-m-phenylene-OC(=O)Ph | |
| 706 | ethylsufonyloxy | Br | 4-(CF$_3$O-benzoyl)methyl | |

TABLE 4-continued

| Cmp | R⁹ | Q | R | m.p./° C. |
|---|---|---|---|---|
| 707 | ethylsufonyloxy | Br | —CH₂C(=O)-[2,5-diCl-4-(OC(=O)Ph)phenyl] | |
| 708 | 4-(acetamido)-phenylsufonyloxy | Br | —CH₂C(=O)-p-phenylene-OC(=O)Ph | |
| 709 | 4-(acetamido)-phenylsufonyloxy | I | —CH₂OC(=O)Ph | |
| 710 | 4-(acetamido)-phenylsufonyloxy | Br | —CH₂C(=O)-p-phenylene-OC(=O)Buᵗ | |
| 711 | 4-(acetamido)-phenylsufonyloxy | Br | —CH₂C(=O)-p-phenylene-OC(=O)Prⁱ | |
| 712 | 4-(acetamido)-phenylsufonyloxy | Br | —CH₂C(=O)-o-phenylene-OC(=O)Ph | |
| 713 | 4-(acetamido)-phenylsufonyloxy | I | —CH₂O(C=O)Buᵗ | |
| 714 | 4-(acetamido)-phenylsufonyloxy | Br | 4-(propionyloxy)benzyl | |
| 715 | 4-(acetamido)-phenylsufonyloxy | Br | 2-(ethoxycarbonyloxy)benzyl | |
| 716 | 4-(acetamido)-phenylsufonyloxy | Br | —CH₂C(=O)-m-phenylene-OC(=O)Ph | |
| 717 | 4-(acetamido)-phenylsufonyloxy | Br | 4-(CF₃O-benzoyl)methyl | |
| 718 | 4-(acetamido)-phenylsufonyloxy | Br | —CH₂C(=O)-[2,5-diCl-4-(OC(=O)Ph)phenyl] | |
| 719 | 2,4-diCl-phenylsulfonyloxy | Br | —CH₂C(=O)-p-phenylene-OC(=O)Ph | |
| 720 | 2,4-CiCl-phenylsulfonyloxy | I | —CH₂OC(=O)Ph | |
| 721 | 2,4-diCl-phenylsulfonyloxy | Br | —CH₂C(=O)-p-phenylene-OC(=O)Buᵗ | |
| 722 | 2,4-CiCl-phenylsulfonyloxy | Br | —CH₂C(=O)-p-phenylene-OC(=O)Prⁱ | |
| 723 | 2,4-CiCl-phenylsulfonyloxy | Br | —CH₂C(=O)-o-phenylene-OC(=O)Ph | |
| 724 | 2,4-CiCl-phenylsulfonyloxy | I | —CH₂O(C=O)Buᵗ | |
| 725 | 2,4-CiCl-phenylsulfonyloxy | Br | 4-(propionyloxy)benzyl | |
| 726 | 2,4-CiCl-phenylsulfonyloxy | Br | 2-(ethoxycarbonyloxy)benzyl | |
| 727 | 2,4-CiCl-phenylsulfonyloxy | Br | —CH₂C(=O)-m-phenylene-OC(=O)Ph | |
| 728 | 2,4-CiCl-phenylsulfonyloxy | Br | 4-(CF₃O-benzoyl)methyl | |

TABLE 4-continued

[Structure: pyrimidine with Cl, Et, R on N; NH linked to cyclohexyl linked to phenyl-OR⁹, with counterion ⁺Q]

| Cmp | R⁹ | Q | R | m.p./° C. |
|---|---|---|---|---|
| 729 | 2,4-CiCl-phenylsulfonyloxy | Br | —CH₂C(=O)- [2,5-dichloro-4-(OC(=O)Ph)phenyl] | |
| 730 | 3,4-diMeO-phenylsulfonyloxy | Br | —CH₂C(=O)-p-phenylene-OC(=O)Ph | |
| 731 | 3,4-diMeO-phenylsulfonyloxy | I | —CH₂OC(=O)Ph | |
| 732 | 3,4-diMeO-phenylsulfonyloxy | Br | —CH₂C(=O)-p-phenylene-OC(=O)Buᵗ | |
| 733 | 3,4-diMeO-phenylsulfonyloxy | Br | —CH₂C(=O)-p-phenylene-OC(=O)Prⁱ | |
| 734 | 3,4-diMeO-phenylsulfonyloxy | Br | —CH₂C(=O)-o-phenylene-OC(=O)Ph | |
| 735 | 3,4-diMeO-phenylsulfonyloxy | I | —CH₂O(C=O)Buᵗ | |
| 736 | 3,4-diMeO-phenylsulfonyloxy | Br | 4-(propionyloxy)benzyl | |
| 737 | 3,4-diMeO-phenylsulfonyloxy | Br | 2-(ethoxycarbonyloxy)benzyl | |
| 738 | 3,4-diMeO-phenylsulfonyloxy | Br | —CH₂C(=O)-m-phenylene-OC(=O)Ph | |
| 739 | 3,4-diMeO-phenylsulfonyloxy | Br | 4-(CF₃O-benzoyl)methyl | |
| 740 | 3,4-diMeO-phenylsulfonyloxy | Br | —CH₂C(=O)- [2,5-dichloro-4-(OC(=O)Ph)phenyl] | |
| 741 | 4-MeO-phenylsulfonyloxy | Br | —CH₂C(=O)-p-phenylene-OC(=O)Ph | |
| 742 | 4-MeO-phenylsulfonyloxy | I | —CH₂OC(=O)Ph | |
| 743 | 4-MeO-phenylsulfonyloxy | Br | —CH₂C(=O)-p-phenylene-OC(=O)Buᵗ | |
| 744 | 4-MeO-phenylsulfonyloxy | Br | —CH₂C(=O)-p-phenylene-OC(=O)Prⁱ | |
| 745 | 4-MeO-phenylsulfonyloxy | Br | —CH₂C(=O)-o-phenylene-OC(=O)Ph | |
| 746 | 4-MeO-phenylsulfonyloxy | I | —CH₂O(C=O)Buᵗ | |
| 747 | 4-MeO-phenylsulfonyloxy | Br | 4-(propionyloxy)benzyl | |
| 748 | 4-MeO-phenylsulfonyloxy | Br | 2-(ethoxycarbonyloxy)benzyl | |
| 749 | 4-MeO-phenylsulfonyloxy | Br | —CH₂C(=O)-m-phenylene-OC(=O)Ph | |
| 750 | 4-MeO-phenylsulfonyloxy | Br | 4-(CF₃O-benzoyl)methyl | |

TABLE 4-continued

| Cmp | R⁹ | Q | R | m.p./° C. |
|---|---|---|---|---|
| 751 | 4-MeO-phenylsulfonyloxy | Br |  | |
| 752 | 2-CF₃-phenylsulfonyloxy | Br | —CH₂C(═O)-p-phenylene-OC(═O)Ph | |
| 753 | 2-CF₃-phenylsulfonyloxy | I | —CH₂OC(═O)Ph | |
| 754 | 2-CF₃-phenylsulfonyloxy | Br | —CH₂C(═O)-p-phenylene-OC(═O)Buᵗ | |
| 755 | 2-CF₃-phenylsulfonyloxy | Br | —CH₂C(═O)-p-phenylene-OC(═O)Prⁱ | |
| 756 | 2-CF₃-phenylsulfonyloxy | Br | —CH₂C(═O)-o-phenylene-OC(═O)Ph | |
| 757 | 2-CF₃-phenylsulfonyloxy | I | —CH₂O(C═O)Buᵗ | |
| 758 | 2-CF₃-phenylsulfonyloxy | Br | 4-(propionyloxy)benzyl | |
| 759 | 2-CF₃-phenylsulfonyloxy | Br | 2-(ethoxycarbonyloxy)benzyl | |
| 760 | 2-CF₃-phenylsulfonyloxy | Br | —CH₂C(═O)-m-phenylene-OC(═O)Ph | |
| 761 | 2-CF₃-phenylsulfonyloxy | Br | 4-(CF₃O-benzoyl)methyl | |
| 762 | 2-CF₃-phenylsulfonyloxy | Br |  | |
| 763 | 3-Cl-4-Me-phenylsulfonyloxy | Br | —CH₂C(═O)-p-phenylene-OC(═O)Ph | |
| 764 | 3-Cl-4-Me-phenylsulfonyloxy | I | —CH₂OC(═O)Ph | |
| 765 | 3-Cl-4-Me-phenylsulfonyloxy | Br | —CH₂C(═O)-phenylene-OC(═O)Buᵗ | |
| 766 | 3-Cl-4-Me-phenylsulfonyloxy | Br | —CH₂C(═O)-p-phenylene-OC(═O)Prⁱ | |
| 767 | 3-Cl-4-Me-phenylsulfonyloxy | Br | —CH₂C(═O)-o-phenylene-OC(═O)Ph | |
| 768 | 3-Cl-4-Me-phenylsulfonyloxy | I | —CH₂O(C═O)Buᵗ | |
| 769 | 3-Cl-4-Me-phenylsulfonyloxy | Br | 4-(propionyloxy)benzyl | |
| 770 | 3-Cl-4-Me-phenylsulfonyloxy | Br | 2-(ethoxycarbonyloxy)benzyl | |
| 771 | 3-Cl-4-Me-phenylsulfonyloxy | Br | —CH₂C(═O)-m-phenylene-OC(═O)Ph | |
| 772 | 3-Cl-4-Me-phenylsulfonyloxy | Br | 4-(CF₃O-benzoyl)methyl | |

TABLE 4-continued

| Cmp | R⁹ | Q | R | m.p./° C. |
|---|---|---|---|---|
| 773 | 3-Cl-4-Me-phenylsulfonyloxy | Br | —CH₂C(=O)- (2,5-dichloro-4-OC(=O)Ph-phenyl) | |
| 774 | 3-NO₂-4-Me-phenylsulfonyloxy | Br | —CH₂C(=O)-p-phenylene-OC(=O)Ph | |
| 775 | 3-NO₂-4-Me-phenylsulfonyloxy | I | —CH₂OC(=O)Ph | |
| 776 | 3-NO₂-4-Me-phenylsulfonyloxy | Br | —CH₂C(=O)-p-phenylene-OC(=O)Buᵗ | |
| 777 | 3-NO₂-4-Me-phenylsulfonyloxy | Br | —CH₂C(=O)-p-phenylene-OC(=O)Prⁱ | |
| 778 | 3-NO₂-4-Me-phenylsulfonyloxy | Br | —CH₂C(=O)-o-phenylene-OC(=O)Ph | |
| 779 | 3-NO₂-4-Me-phenylsulfonyloxy | I | —CH₂O(C=O)Buᵗ | |
| 780 | 3-NO₂-4-Me-phenylsulfonyloxy | Br | 4-(propionyloxy)benzyl | |
| 781 | 3-NO₂-4-Me-phenylsulfonyloxy | Br | 2-(ethoxycarbonyloxy)benzyl | |
| 782 | 3-NO₂-4-Me-phenylsulfonyloxy | Br | —CH₂C(=O)-m-phenylene-OC(=O)Ph | |
| 783 | 3-NO₂-4-Me-phenylsulfonyloxy | Br | 4-(CF₃O-benzoyl)methyl | |
| 784 | 3-NO₂-4-Me-phenylsulfonyloxy | Br | —CH₂C(=O)- (2,5-dichloro-4-OC(=O)Ph-phenyl) | |
| 785 | propylsulfonyloxy | Br | —CH₂C(=O)-p-phenylene-OC(=O)Ph | |
| 786 | propylsulfonyloxy | I | —CH₂OC(=O)Ph | |
| 787 | propylsulfonyloxy | Br | —CH₂C(=O)-p-phenylene-OC(=O)Buᵗ | |
| 788 | propylsulfonyloxy | Br | —CH₂C(=O)-p-phenylene-OC(=O)Prⁱ | |
| 789 | propylsulfonyloxy | Br | —CH₂C(=O)-o-phenylene-OC(=O)Ph | |
| 790 | propylsulfonyloxy | I | —CH₂O(C=O)Buᵗ | |
| 791 | propylsulfonyloxy | Br | 4-(propionyloxy)benzyl | |
| 792 | propylsulfonyloxy | Br | 2-(ethoxycarbonyloxy)benzyl | |
| 793 | propylsulfonyloxy | Br | —CH₂C(=O)-m-phenylene-OC(=O)Ph | |
| 794 | propylsulfonyloxy | Br | 4-(CF₃O-benzoyl)methyl | |

TABLE 4-continued

| Cmp | R⁹ | Q | R | m.p./° C. |
|---|---|---|---|---|
| 795 | propylsulfonyloxy | Br | —CH₂C(=O)-(2,5-dichloro-4-OC(=O)Ph-phenyl) | |
| 796 | 3-NO₂-phenylsulfonyloxy | Br | —CH₂C(=O)-p-phenylene-OC(=O)Ph | |
| 797 | 3-NO₂-phenylsulfonyloxy | I | —CH₂OC(=O)Ph | |
| 798 | 3-NO₂-phenylsulfonyloxy | Br | —CH₂C(=O)-p-phenylene-OC(=O)Buᵗ | |
| 799 | 3-NO₂-phenylsulfonyloxy | Br | —CH₂C(=O)-p-phenylene-OC(=O)Prⁱ | |
| 800 | 3-NO₂-phenylsulfonyloxy | Br | —CH₂C(=O)-o-phenylene-OC(=O)Ph | |
| 801 | 3-NO₂-phenylsulfonyloxy | I | —CH₂O(C=O)Buᵗ | |
| 802 | 3-NO₂-phenylsulfonyloxy | Br | 4-(propionyloxy)benzyl | |
| 803 | 3-NO₂-phenylsulfonyloxy | Br | 2-(ethoxycarbonyloxy)benzyl | |
| 804 | 3-NO₂-phenylsulfonyloxy | Br | —CH₂C(=O)-m-phenylene-OC(=O)Ph | |
| 805 | 3-NO₂-phenylsulfonyloxy | Br | 4-(CF₃O-benzoyl)methyl | |
| 806 | 3-NO₂-phenylsulfonyloxy | Br | —CH₂C(=O)-(2,5-dichloro-4-OC(=O)Ph-phenyl) | |
| 807 | 4-NO₂-phenylsulfonyloxy | Br | —CH₂C(=O)-p-phenylene-OC(=O)Ph | |
| 808 | 4-NO₂-phenylsulfonyloxy | I | —CH₂OC(=O)Ph | |
| 809 | 4-NO₂-phenylsulfonyloxy | Br | —CH₂C(=O)-p-phenylene-OC(=O)Buᵗ | |
| 810 | 4-NO₂-phenylsulfonyloxy | Br | —CH₂C(=O)-p-phenylene-OC(=O)Prⁱ | |
| 811 | 4-NO₂-phenylsulfonyloxy | Br | —CH₂C(=O)-o-phenylene-OC(=O)Ph | |
| 812 | 4-NO₂-phenylsulfonyloxy | I | —CH₂O(C=O)Buᵗ | |
| 813 | 4-NO₂-phenylsulfonyloxy | Br | 4-(propionyloxy)benzyl | |
| 814 | 4-NO₂-phenylsulfonyloxy | Br | 2-(ethoxycarbonyloxy)benzyl | |
| 815 | 4-NO₂-phenylsulfonyloxy | Br | —CH₂C(=O)-m-phenylene-OC(=O)Ph | |
| 816 | 4-NO₂-phenylsulfonyloxy | Br | 4-(CF₃O-benzoyl)methyl | |

TABLE 4-continued

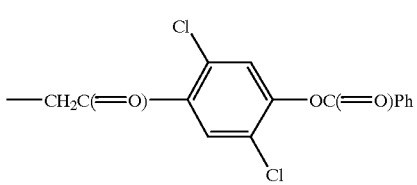

| Cmp | R⁹ | Q | R | m.p./° C. |
|---|---|---|---|---|
| 817 | 4-NO$_2$-phenylsulfonyloxy | Br | 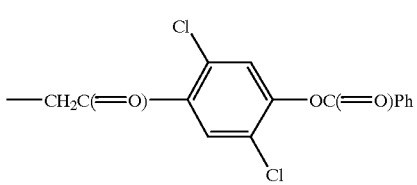 | |
| 818 | 2-NO$_2$-phenylsulfonyloxy | Br | —CH$_2$C(=O)-p-phenylene-OC(=O)Ph | |
| 819 | 2-NO$_2$-phenylsulfonyloxy | I | —CH$_2$OC(=O)Ph | |
| 820 | 2-NO$_2$-phenylsulfonyloxy | Br | —CH$_2$C(=O )-p-phenylene-OC(=O)Bu$^t$ | |
| 821 | 2-NO$_2$-phenylsulfonyloxy | Br | —CH$_2$C(=O)-p-phenylene-OC(=O)Pr$^i$ | |
| 822 | 2-NO$_2$-phenylsulfonyloxy | Br | —CH$_2$C(=O)-o-phenylene-OC(=O)Ph | |
| 823 | 2-NO$_2$-phenylsulfonyloxy | I | —CH$_2$O(C=O)Bu$^t$ | |
| 824 | 2-NO$_2$-phenylsulfonyloxy | Br | 4-(propionyloxy)benzyl | |
| 825 | 2-NO$_2$-phenylsulfonyloxy | Br | 2-(ethoxycarbonyloxy)benzyl | |
| 826 | 2-NO$_2$-phenylsulfonyloxy | Br | —CH$_2$C(=O)-m-phenylene-OC(=O)Ph | |
| 827 | 2-NO$_2$-phenylsulfonyloxy | Br | 4-(CF$_3$O-benzoyl)methyl | |
| 828 | 2-NO$_2$-phenylsulfonyloxy | Br | 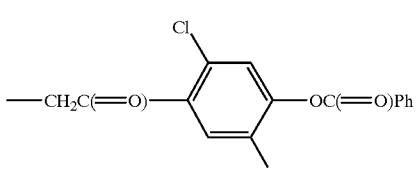 | |
| 829 | 4-I-phenylsulfonyloxy | Br | —CH$_2$C(=O)-p-phenylene-OC(=O)Ph | |
| 830 | 4-I-phenylsulfonyloxy | I | —CH$_2$OC(=O)Ph | |
| 831 | 4-I-phenylsulfonyloxy | Br | —CH$_2$C(=O)-p-phenylene-OC(=O)Bu$^t$ | |
| 832 | 4-I-phenylsulfonyloxy | Br | —CH$_2$C(=O)-p-phenylene-OC(=O)Pr$^i$ | |
| 833 | 4-I-phenylsulfonyloxy | Br | —CH$_2$C(=O)-o-phenylene-OC(=O)Ph | |
| 834 | 4-I-phenylsulfonyloxy | I | —CH$_2$O(C=O)Bu$^t$ | |
| 835 | 4-I-phenylsulfonyloxy | Br | 4-(propionyloxy)benzyl | |
| 836 | 4-1-phenylsulfonyloxy | Br | 2-(ethoxycarbonyloxy)benzyl | |
| 837 | 4-I-phenylsulfonyloxy | Br | —CH$_2$C(=O)-m-phenylene-OC(=O)Ph | |
| 838 | 4-l-phenylsulfonyloxy | Br | 4-(CF$_3$O-benzoyl)methyl | |

TABLE 4-continued

[Structure: pyrimidine with Cl, Et, NH-cyclohexyl-phenyl-OR⁹, N-R, with +Q counter-ion]

| Cmp | R⁹ | Q | R | m.p./° C. |
|---|---|---|---|---|
| 839 | 4-l-phenylsulfonyloxy | Br | —CH₂C(=O)-(2,5-dichloro-4-(OC(=O)Ph)-phenyl) | |
| 840 | isopropylsulfonyloxy | Br | —CH₂C(=O)-p-phenylene-OC(=O)Ph | |
| 841 | isopropylsulfonyloxy | I | —CH₂OC(=O)Ph | |
| 842 | isopropylsulfonyloxy | Br | —CH₂C(=O)-p-phenylene-OC(=O)Buᵗ | |
| 843 | isopropylsulfonyloxy | Br | —CH₂C(=O)-p-phenylene-OC(=O)Prⁱ | |
| 844 | isopropylsulfonyloxy | Br | —CH₂C(=O)-o-phenylene-OC(=O)Ph | |
| 845 | isopropylsulfonyloxy | I | —CH₂O(C=O)Buᵗ | |
| 846 | isopropylsulfonyloxy | Br | 4-(propionyloxy)benzyl | |
| 847 | isopropylsulfonyloxy | Br | 2-(ethoxycarbonyloxy)benzyl | |
| 848 | isopropylsulfonyloxy | Br | —CH 2C(=O)-m-phenylene-OC(=O)Ph | |
| 849 | isopropylsulfonyloxy | Br | 4-(CF₃O-benzoyl)methyl | |
| 850 | isopropylsulfonyloxy | Br | —CH₂C(=O)-(2,5-dichloro-4-(OC(=O)Ph)-phenyl) | |
| 851 | 2-CF₃O-phenylsulfonyloxy | Br | —CH₂C(=O)-p-phenylene-OC(=O)Ph | |
| 852 | 2-CF₃O-phenylsulfonyloxy | I | —CH₂OC(=O)Ph | |
| 853 | 2-CF₃O-phenylsulfonyloxy | Br | —CH₂C(=O)-p-phenylene-OC(=O)Buᵗ | |
| 854 | 2-CF₃O-phenylsulfonyloxy | Br | —CH₂C(=O)-p-phenylene-OC(=O)Prⁱ | |
| 855 | 2-CF₃O-phenylsulfonyloxy | Br | —CH₂C(=O)-o-phenylene-OC(=O)Ph | |
| 856 | 2-CF₃O-phenylsulfonyloxy | I | —CH₂O(C=O)Buᵗ | |
| 857 | 2-CF₃O-phenylsulfonyloxy | Br | 4-(propionyloxy)benzyl | |
| 858 | 2-CF₃O-phenylsulfonyloxy | Br | 2-(ethoxycarbonyloxy)benzyl | |
| 859 | 2-CF₃O-phenylsulfonyloxy | Br | —CH₂C(=O)-m-phenylene-OC(=O)Ph | |
| 860 | 2-CF₃O-phenylsulfonyloxy | Br | 4-(CF₃O-benzoyl)methyl | |

TABLE 4-continued

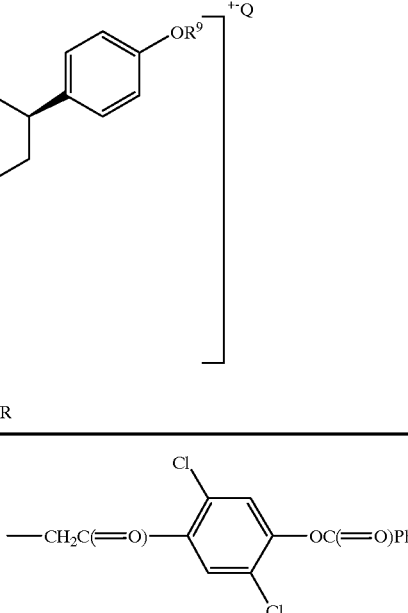

| Cmp | R⁹ | Q | R | m.p./° C. |
|---|---|---|---|---|
| 861 | 2-CF₃O-phenylsulfonyloxy | Br | 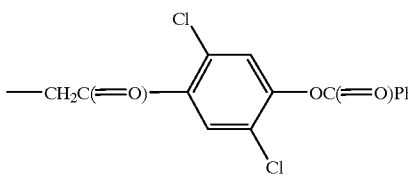 | |
| 862 | OSO₂CCl₃ | Br | —CH₂C(=O)-p-phenylene-OC(=O)Ph | |
| 863 | OSO₂CCl₃ | I | —CH₂OC(=O)Ph | |
| 864 | OSO₂CCl₃ | Br | —CH₂C(=O)-p-phenylene-OC(=O)Buᵗ | |
| 865 | OSO₂CCl₃ | Br | —CH₂C(=O)-p-phenylene-OC(=O)Prⁱ | |
| 866 | OSO₂CC₃ | Br | —CH₂C(=O)-o-phenylene-OC(=O)Ph | |
| 867 | OSO₂CCl₃ | I | —CH₂O(C=O)Buᵗ | |
| 868 | OSO₂CCl₃ | Br | 4-(propionyloxy)benzyl | |
| 869 | OSO₂CCl₃ | Br | 2-(ethoxycarbonyloxy)benzyl | |
| 870 | OSO₂CCl₃ | Br | —CH₂C(=O)-m-phenylene-OC(=O)Ph | |
| 871 | OSO₂CCl₃ | Br | 4-(CF₃O-benzoyl)methyl | |
| 872 | OSO₂CCl₃ | Br | | |
| 873 | OSO₂CCl₃ | Br | —CH₂C(=O)-p-phenylene-OC(=O)Ph | |
| 874 | OSO₂CCl₂ | I | —CH₂OC(=O)Ph | |
| 875 | OSO₂CCl₂ | Br | —CH₂C(=O)-p-phenylene-OC(=O)Buᵗ | |
| 876 | OSO₂CCl₂ | Br | —CH₂C(=O)-p-phenylene-OC(=O)Prⁱ | |
| 877 | OSO₂CCl₂ | Br | —CH₂C(=O)-o-phenylene-OC(=O)Ph | |
| 878 | OSO₂CCl₂ | I | —CH₂O(C=O)Buᵗ | |
| 879 | OSO₂CCl₂ | Br | 4-(propionyloxy)benzyl | |
| 880 | OSO₂CCl₂ | Br | 2-(ethoxycarbonyloxy)benzyl | |
| 881 | OSO₂CCl₂ | Br | —CH₂C(=O)-m-phenylene-OC(=O)Ph | |
| 882 | OSO₂CCl₂ | Br | 4-(CF₃O-benzoyl)methyl | |

TABLE 4-continued

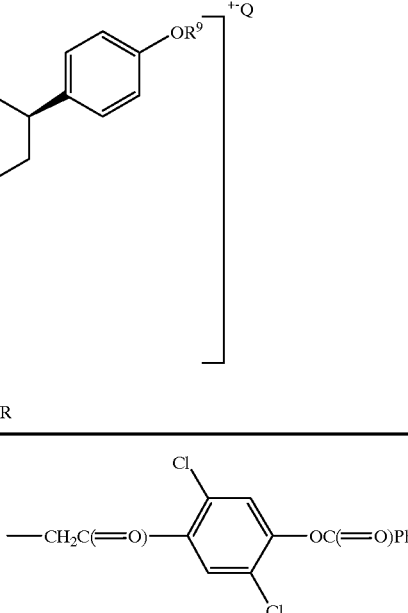

| Cmp | R⁹ | Q | R | m.p./° C. |
|---|---|---|---|---|
| 883 | OSO$_2$CCl$_3$ | Br | 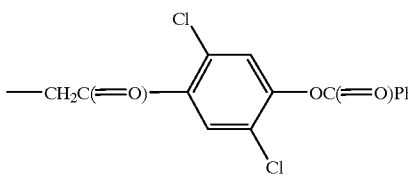 | |
| 884 | butylsulfonyloxy | Br | —CH$_2$C(=O)-p-phenylene-OC(=O)Ph | |
| 885 | butylsulfonyloxy | I | —CH$_2$OC(=O)Ph | |
| 886 | butylsulfonyloxy | Br | —CH$_2$C(=O)-p-phenylene-OC(=O)Bu$^t$ | |
| 887 | butylsulfonyloxy | Br | —CH$_2$C(=O)-p-phenylene-OC(=O)Pr$^i$ | |
| 888 | butylsulfonyloxy | Br | —CH$_2$C(=O)-o-phenylene-OC(=O)Ph | |
| 889 | butylsulfonyloxy | I | —CH$_2$O(C=O)Bu$^t$ | |
| 890 | butylsulfonyloxy | Br | 4-(propionyloxy)benzyl | |
| 891 | butylsulfonyloxy | Br | 2-(ethoxycarbonyloxy)benzyl | |
| 892 | butylsulfonyloxy | Br | —CH$_2$C(=O)-m-phenylene-OC(=O)Ph | |
| 893 | butylsulfonyloxy | Br | 4-(CF$_3$O-benzoyl)methyl | |
| 894 | butylsulfonyloxy | Br | (structure: 2,5-dichloro-phenylene with —CH$_2$C(=O)O— and —OC(=O)Ph substituents) | |
| 895 | benzylsulfonyloxy | Br | —CH$_2$C(=O)-p-phenylene-OC(=O)Ph | |
| 896 | benzylsulfonyloxy | I | —CH$_2$OC(=O)Ph | |
| 897 | benzylsulfonyloxy | Br | —CH$_2$C(=O)-p-phenylene-OC(=O)Bu$^t$ | |
| 898 | benzylsulfonyloxy | Br | —CH$_2$C(=O)-p-phenylene-OC(=O)Pr$^i$ | |
| 899 | benzylsulfonyloxy | Br | —CH$_2$C(=O)-o-phenylene-OC(=O)Ph | |
| 900 | benzylsulfonyloxy | I | —CH$_2$O(C=O)Bu$^t$ | |
| 901 | benzylsulfonyloxy | Br | 4-(propionyloxy)benzyl | |
| 902 | benzylsulfonyloxy | Br | 2-(ethoxycarbonyloxy)benzyl | |
| 903 | benzylsulfonyloxy | Br | —CH$_2$C(=O)-m-phenylene-OC(=O)Ph | |
| 904 | benzylsulfonyloxy | Br | 4-(CF$_3$O-benzoyl)methyl | |

TABLE 4-continued

[Structure: pyrimidine with Cl, Et, R substituents, NH-cyclohexyl-phenyl-OR⁹, with +Q counterion]

| Cmp | R⁹ | Q | R | m.p./° C. |
|---|---|---|---|---|
| 905 | benzylsulfonyloxy | Br | [2,5-dichloro-4-(OC(=O)Ph)phenyl attached via —CH₂C(=O)O—] | |
| 906 | octylsulfonyloxy | Br | —CH₂C(=O)-p-phenylene-OC(=O)Ph | |
| 907 | octylsulfonyloxy | I | —CH₂OC(=O)Ph | |
| 908 | octylsulfonyloxy | Br | —CH₂C(=O)-p-phenylene-OC(=O)Bu$^t$ | |
| 909 | octylsulfonyloxy | Br | —CH₂C(=O)-p-phenylene-OC(=O)Pr$^i$ | |
| 910 | octylsulfonyloxy | Br | —CH₂C(=O)-o-phenylene-OC(=O)Ph | |
| 911 | octylsulfonyloxy | I | —CH₂O(C=O)Bu$^t$ | |
| 912 | octylsulfonyloxy | Br | 4-(propionyloxy)benzyl | |
| 913 | octylsulfonyloxy | Br | 2-(ethoxycarbonyloxy)benzyl | |
| 914 | octylsulfonyloxy | Br | —CH₂C(=O)-m-phenylene-OC(=O)Ph | |
| 915 | octylsulfonyloxy | Br | 4-(CF₃O-benzoyl)methyl | |
| 916 | octylsulfonyloxy | Br | [2,5-dichloro-4-(OC(=O)Ph)phenyl attached via —CH₂C(=O)O—] | |
| 917 | 2-NO₂-benzylsulfonyloxy | Br | —CH₂C(=O)-p-phenylene-OC(=O)Ph | |
| 918 | 2-NO₂-benzylsulfonyloxy | I | —CH₂OC(=O)Ph | |
| 919 | 2-NO₂-benzylsulfonyloxy | Br | —CH₂C(=O)-p-phenylene-OC(=O)Bu$^t$ | |
| 920 | 2-NO₂-benzylsulfonyloxy | Br | —CH₂C(=O)-p-phenylene-OC(=O)Pr$^i$ | |
| 921 | 2-NO₂-benzylsulfonyloxy | Br | —CH₂C(=O)-o-phenylene-OC(=O)Ph | |
| 922 | 2-NO₂-benzylsulfonyloxy | I | —CH₂O(C=O)Bu$^t$ | |
| 923 | 2-NO₂-benzylsulfonyloxy | Br | 4-(propionyloxy)benzyl | |
| 924 | 2-NO₂-benzylsulfonyloxy | Br | 2-(ethoxycarbonyloxy)benzyl | |
| 925 | 2-NO₂-benzylsulfonyloxy | Br | —CH₂C(=O)-m-phenylene-OC(=O)Ph | |
| 926 | 2-NO₂-benzylsulfonyloxy | Br | 4-(CF₃O-benzoyl)methyl | |

TABLE 4-continued

[Structure: pyrimidine with Cl, Et substituents, NH linked to trans-cyclohexyl-phenyl-OR⁹, N-R, counterion ⁺Q]

| Cmp | R⁹ | Q | R | m.p./° C. |
|---|---|---|---|---|
| 927 | 2-NO₂-benzylsulfonyloxy | Br | —CH₂C(=O)-(2,5-dichloro-phenylene)-OC(=O)Ph | |
| 928 | 5-Br-thienyl-2-sulfonyloxy | Br | —CH₂C(=O)-p-phenylene-OC(=O)Ph | |
| 929 | 5-Br-thienyl-2-sulfonyloxy | I | —CH₂OC(=O)Ph | |
| 930 | 5-Br-thienyl-2-sulfonyloxy | Br | —CH₂C(=O)-p-phenylene-OC(=O)Buᵗ | |
| 931 | 5-Br-thienyl-2-sulfonyloxy | Br | —CH₂C(=O)-p-phenylene-OC(=O)Prⁱ | |
| 932 | 5-Br-thienyl-2-sulfonyloxy | Br | —CH₂C(=O)-o-phenylene-OC(=O)Ph | |
| 933 | 5-Br-thienyl-2-sulfonyloxy | I | —CH₂O (C=O)Buᵗ | |
| 934 | 5-Br-thienyl-2-sulfonyloxy | Br | 4-(propionyloxy)benzyl | |
| 935 | 5-Br-thienyl-2-sulfonyloxy | Br | 2-(ethoxycarbonyloxy)benzyl | |
| 936 | 5-Br-thienyl-2-sulfonyloxy | Br | —CH₂C(=O)-m-phenylene-OC(=O)Ph | |
| 937 | 5-Br-thienyl-2-sulfonyloxy | Br | 4-(CF₃O-benzyl)methyl | |
| 938 | 5-Br-thienyl-2-sulfonyloxy | Br | —CH₂C(=O)-(2,5-dichloro-phenylene)-OC(=O)Ph | |
| 939 | 3,5-dimethylisoxazol-4-yl-SO₂-O— | Br | —CH₂C(=O)-p-phenylene-OC(=O)Ph | |
| 940 | 3,5-dimethylisoxazol-4-yl-SO₂-O— | I | —CH₂OC(=O)Ph | |

TABLE 4-continued

| Cmp | R⁹ | Q | R | m.p./° C. |
|---|---|---|---|---|
| 941 | —OSO₂-(3,5-dimethylisoxazol-4-yl) | Br | —CH₂C(=O)-p-phenylene-OC(=O)Buᵗ | |
| 942 | —OSO₂-(3,5-dimethylisoxazol-4-yl) | Br | —CH₂C(=O)-p-phenylene-OC(=O)Prⁱ | |
| 943 | —OSO₂-(3,5-dimethylisoxazol-4-yl) | Br | —CH₂C(=O)-o-phenylene-OC(=O)Ph | |
| 944 | —OSO₂-(3,5-dimethylisoxazol-4-yl) | I | —CH₂O(C=O)Buᵗ | |
| 945 | —OSO₂-(3,5-dimethylisoxazol-4-yl) | Br | 4-(propionyloxy)benzyl | |
| 946 | —OSO₂-(3,5-dimethylisoxazol-4-yl) | Br | 2-(ethoxycarbonyloxy)benzyl | |

TABLE 4-continued

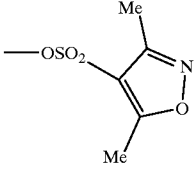

| Cmp | R⁹ | Q | R | m.p./° C. |
|---|---|---|---|---|
| 947 | 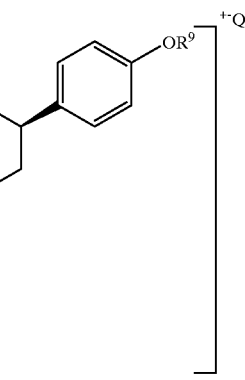 | Br | —CH₂C(=O)-m-phenylene-OC(=O)Ph | |
| 948 | 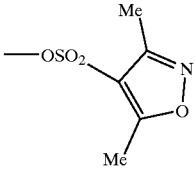 | Br | 4-(CF₃O-benzoyl)methyl | |
| 949 | 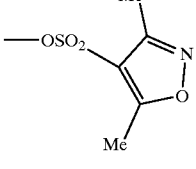 | Br | 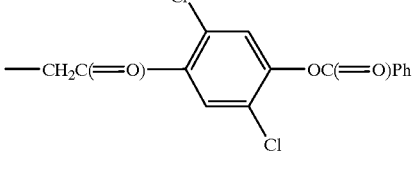 | |
| 950 | —OSO₂NMe₂ | Br | —CH₂C(=O)-p-phenylene-OC(=O)Ph | |
| 951 | —OSO₂NMe₂ | I | —CH₂OC(=O)Ph | |
| 952 | —OSO₂NMe₂ | Br | —CH₂C(=O)-p-phenylene-OC(=O)Buᵗ | |
| 953 | —OSO₂NMe₂ | Br | —CH₂C(=O)-p-phenylene-OC(=O)Prⁱ | |
| 954 | —OSO₂NMe₂ | Br | —CH₂C(=O)-o-phenylene-OC(=O)Ph | |
| 955 | —OSO₂NMe₂ | I | —CH₂O(C=O)Buᵗ | |
| 956 | —OSO₂NMe₂ | Br | 4-(propionyloxy)benzyl | |
| 957 | —OSO₂NMe₂ | Br | 2-(ethoxycarbonyloxy)benzyl | |
| 958 | —OSO₂NMe₂ | Br | —CH₂C(=O)-m-phenylene-OC(=O)Ph | |
| 959 | —OSO₂NMe₂ | Br | 4-(CF₃O-benzoyl)methyl | |
| 960 | —OSO₂NMe₂ | Br | 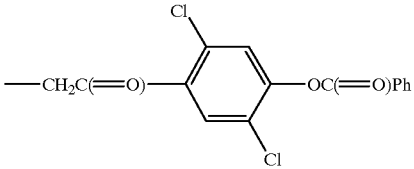 | |

TABLE 4-continued

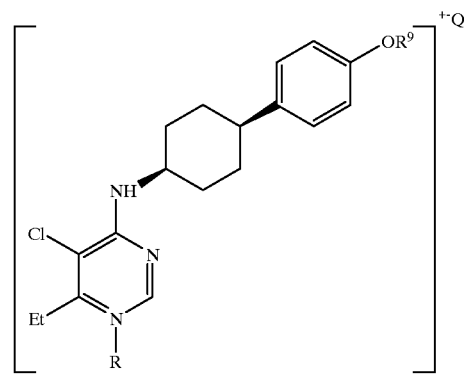

| Cmp | R⁹ | Q | R | m.p./° C. |
|---|---|---|---|---|
| 961 | Me, N, —OSO₂—thiazole—NHC(=O)Me (4-Me, 2-NHC(=O)Me thiazole-5-ylsulfonyloxy) | Br | —CH₂C(=O)-p-phenylene-OC(=O)Ph | |
| 962 | Me, N, —OSO₂—thiazole—NHC(=O)Me | I | —CH₂OC(=O)Ph | |
| 963 | Me, N, —OSO₂—thiazole—NHC(=O)Me | Br | —CH₂C(=O)-p-phenylene-OC(=O)Bu$^t$ | |
| 964 | Me, N, —OSO₂—thiazole—NHC(=O)Me | Br | —CH₂C(=O)-p-phenylene-OC(=O)Pr$^i$ | |
| 965 | Me, N, —OSO₂—thiazole—NHC(=O)Me | Br | —CH₂C(=O)-o-phenylene-OC(=O)Ph | |
| 966 | Me, N, —OSO₂—thiazole—NHC(=O)Me | I | —CH₂O(C=O)Bu$^t$ | |
| 967 | Me, N, —OSO₂—thiazole—NHC(=O)Me | Br | 4-(propionyloxy)benzyl | |
| 968 | Me, N, —OSO₂—thiazole—NHC(=O)Me | Br | 2-(ethoxycarbonyloxy)benzyl | |

TABLE 4-continued

| Cmp | R⁹ | Q | R | m.p./° C. |
|---|---|---|---|---|
| 969 | 4-Me-2-(NHC(=O)Me)-thiazol-5-yl-OSO₂– | Br | —CH₂C(=O)-m-phenylene- | |
| 970 | 4-Me-2-(NHC(=O)Me)-thiazol-5-yl-OSO₂– | Br | 4-(CF₃O-benzoyl)methyl | |
| 971 | 4-Me-2-(NHC(=O)Me)-thiazol-5-yl-OSO₂– | Br | —CH₂C(=O)-(2,5-dichloro-4-(OC(=O)Ph))phenyl | |
| 972 | —OP(O)Me₂ | Br | —CH₂C(=O)-p-phenylene-OC(=O)Ph | |
| 973 | —OP(O)Me₂ | I | —CH₂OC(=O)Ph | |
| 974 | —OP(O)Me₂ | Br | —CH₂C(=O)-p-phenylene-OC(=O)Buᵗ | |
| 975 | —OP(O)Me₂ | Br | —CH₂C(=O)-p-phenylene-OC(=O)Prⁱ | |
| 976 | —OP(O)Me₂ | Br | —CH₂C(=O)-o-phenylene-OC(=O)Ph | |
| 977 | —OP(O)Me₂ | I | —CH₂O(C=O)Buᵗ | |
| 978 | —OP(O)Me₂ | Br | 4-(propionyloxy)benzyl | |
| 979 | —OP(O)Me₂ | Br | 2-(ethoxycarbonyloxy)benzyl | |
| 980 | —OP(O)Me₂ | Br | —CH₂C(=O)-m-phenylene-OC(=O)Ph | |
| 981 | —OP(O)Me₂ | Br | 4-(CF₃O-benzoyl)methyl | |
| 982 | —OP(O)Me₂ | Br | —CH₂C(=O)-(2,5-dichloro-4-(OC(=O)Ph))phenyl | |
| 983 | —OP(O)Et₂ | Br | —CH₂C(=O)-p-phenylene-OC(=O)Ph | |
| 984 | —OP(O)Et₂ | I | —CH₂OC(=O)Ph | |
| 985 | —OP(O)Et₂ | Br | —CH₂C(=O)-p-phenylene-OC(=O)Buᵗ | |
| 986 | —OP(O)Et₂ | Br | —CH₂C(=O)-p-phenylene-OC(=O)Prⁱ | |
| 987 | —OP(O)Et₂ | Br | —CH₂C(=O)-o-phenylene-OC(=O)Ph | |

TABLE 4-continued

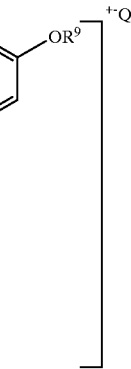

| Cmp | R⁹ | Q | R | m.p./° C. |
|---|---|---|---|---|
| 988 | —OP(O)Et₂ | I | —CH₂O(C=O)Buᵗ | |
| 989 | —OP(O)Et₂ | Br | 4-(propionyloxy)benzyl | |
| 990 | —OP(O)Et₂ | Br | 2-(ethoxycarbonyloxy)benzyl | |
| 991 | —OP(O)Et₂ | Br | —CH₂C(=O)-m-phenylene-OC(=O)Ph | |
| 992 | —OP(O)Et₂ | Br | 4-(CF₃O-benzoyl)methyl | |
| 993 | —OP(O)Et₂ | Br | 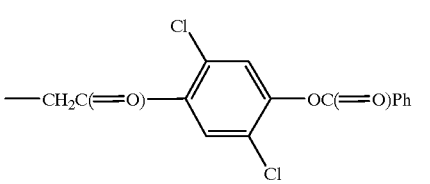 | |
| 994 | —OP(O)Ph₂ | Br | —CH₂C(=O)-p-phenylene-OC(=O)Ph | |
| 995 | —OP(O)Ph₂ | I | —CH₂OC(=O)Ph | |
| 996 | —OP(O)Ph₂ | Br | —CH₂C(=O)-p-phenylene-OC(=O)Buᵗ | |
| 997 | —OP(O)Ph₂ | Br | —CH₂C(=O)-p-phenylene-OC(=O)Prⁱ | |
| 998 | —OP(O)Ph₂ | Br | —CH₂C(=O)-o-phenylene-OC(=O)Ph | |
| 999 | —OP(O)Ph₂ | I | —CH₂O(C=O)Buᵗ | |
| 1000 | —OP(O)Ph₂ | Br | 4-(propionyloxy)benzyl | |
| 1001 | —OP(O)Ph₂ | Br | 2-(ethoxycarbonyloxy)benzyl | |
| 1002 | —OP(O)Ph₂ | Br | —CH₂C(=O)-m-phenylene-OC(=O)Ph | |
| 1003 | —OP(O)Ph₂ | Br | 4-(CF₃O-benzoyl)methyl | |
| 1004 | —OP(O)Ph₂ | Br | 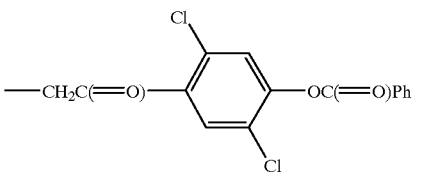 | |
| 1005 | —OP(O)(Me)Ph | Br | —CH₂C(=O)-p-phenylene-OC(=O)Ph | |
| 1006 | —OP(O)(Me)Ph | I | —CH₂OC(=O)Ph | |
| 1007 | —OP(O)(Me)Ph | Br | —CH₂C(=O)-p-phenylene-OC(=O)Buᵗ | |
| 1008 | —OP(O)(Me)Ph | Br | —CH₂C(=O)-p-phenylene-OC(=O)Prⁱ | |
| 1009 | —OP(O)(Me)Ph | Br | —CH₂C(=O)-o-phenylene-OC(=O)Ph | |
| 1010 | —OP(O)(Me)Ph | I | —CH₂O(C=O)Buᵗ | |
| 1011 | —OP(O)(Me)Ph | Br | 4-(propionyloxy)benzyl | |
| 1012 | —OP(O)(Me)Ph | Br | 2-(ethoxycarbonyloxy)benzyl | |
| 1013 | —OP(O)(Me)Ph | Br | —CH₂C(=O)-m-phenylene-OC(=O)Ph | |
| 1014 | —OP(O)(Me)Ph | Br | 4-(CF₃O-benzoyl)methyl | |

TABLE 4-continued

| Cmp | R⁹ | Q | R | m.p./° C. |
|---|---|---|---|---|
| 1015 | —OP(O)(Me)Ph | Br | 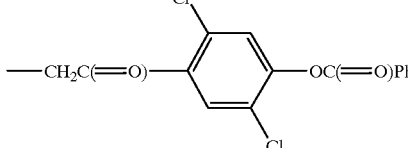 | |
| 1016 | —OP(O)(cyclohexyl)₂ | Br | —CH₂C(=O)-p-phenylene-OC(=O)Ph | |
| 1017 | —OP(O)(cyclohexyl)₂ | I | —CH₂OC(=O)Ph | |
| 1018 | —OP(O)(cyclohexyl)₂ | Br | —CH₂C(=O)-p-phenylene-OC(=O)Buᵗ | |
| 1019 | —OP(O)(cyclohexyl)₂ | Br | —CH₂C(=O)-p-phenylene-OC(=O)Prⁱ | |
| 1020 | —OP(O)(cyclohexyl)₂ | Br | —CH₂C(=O)-o-phenylene-OC(=O)Ph | |
| 1021 | —OP(O)(cyclohexyl)₂ | I | —CH₂O(C=O)Buᵗ | |
| 1022 | —OP(O)(cyclohexyl)₂ | Br | 4-(propionyloxy)benzyl | |
| 1023 | —OP(O)(cyclohexyl)₂ | Br | 2-(ethoxycarbonyloxy)benzyl | |
| 1024 | —OP(O)(cyclohexyl)₂ | Br | —CH₂C(=O)-m-phenylene-OC(=O)Ph | |
| 1025 | —OP(O)(cyclohexyl)₂ | Br | 4-(CF₃O-benzoyl)methyl | |
| 1026 | —OP(O)(cyclohexyl)₂ | Br | 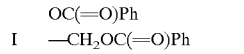 | |
| 1027 | —OP(O)(methoxy)₂ | Br | —CH₂C(=O)-p-phenylene-OC(=O)Ph | |
| 1028 | —OP(O)(methoxy)₂ | I | —CH₂OC(=O)Ph | |
| 1029 | —OP(O)(methoxy)₂ | Br | —CH₂C(=O)-p-phenylene-OC(=O)Buᵗ | |
| 1030 | —OP(O)(methoxy)₂ | Br | —CH₂C(=O)-p-phenylene-OC(=O)Prⁱ | |
| 1031 | —OP(O)(methoxy)₂ | Br | —CH₂C(=O)-o-phenylene-OC(=O)Ph | |
| 1032 | —OP(O)(methoxy)₂ | I | —CH₂O(C=O)Buᵗ | |
| 1033 | —OP(O)(methoxy)₂ | Br | 4-(propionyloxy)benzyl | |
| 1034 | —OP(O)(methoxy)₂ | Br | 2-(ethoxycarbonyloxy)benzyl | |
| 1035 | —OP(O)(methoxy)₂ | Br | —CH₂C(=O)-m-phenylene-OC(=O)Ph | |
| 1036 | —OP(O)(methoxy)₂ | Br | 4-(CF₃O-benzoyl)methyl | |

TABLE 4-continued

[Structure: pyrimidine with Cl, Et, and R on N; NH linked to cyclohexyl-phenyl-OR⁹ group; charge +Q]

| Cmp | R⁹ | Q | R | m.p./° C. |
|---|---|---|---|---|
| 1037 | —OP(O)(methoxy)₂ | Br | —CH₂C(=O)-[2,5-dichloro-4-(OC(=O)Ph)phenyl] | |
| 1038 | —OP(O)(ethoxy)₂ | Br | —CH₂C(=O)-p-phenylene-OC(=O)Ph | |
| 1039 | —OP(O)(ethoxy)₂ | I | —CH₂OC(=O)Ph | |
| 1040 | —OP(O)(ethoxy)₂ | Br | —CH₂C(=O)-p-phenylene-OC(=O)Buᵗ | |
| 1041 | —OP(O)(ethoxy)₂ | Br | —CH₂C(=O)-p-phenylene-OC(=O)Prⁱ | |
| 1042 | —OP(O)(ethoxy)₂ | Br | —CH₂C(=O)-o-phenylene-OC(=O)Ph | |
| 1043 | —OP(O)(ethoxy)₂ | I | —CH₂O(C=O)Buᵗ | |
| 1044 | —OP(O)(ethoxy)₂ | Br | 4-(propionyloxy)benzyl | |
| 1045 | —OP(O)(ethoxy)₂ | Br | 2-(ethoxycarbonyloxy)benzyl | |
| 1046 | —OP(O)(ethoxy)₂ | Br | —CH₂C(=O)-m-phenylene-OC(=O)Ph | |
| 1047 | —OP(O)(ethoxy)₂ | Br | 4-(CF₃O-benzoyl)methyl | |
| 1048 | —OP(O)(ethoxy)₂ | Br | —CH₂C(=O)-[2,5-dichloro-4-(OC(=O)Ph)phenyl] | |
| 1049 | —OP(O)(propoxy)₂ | Br | —CH₂C(=O)-p-phenylene-OC(=O)Ph | |
| 1050 | —OP(O)(propoxy)₂ | I | —CH₂OC(=O)Ph | |
| 1051 | —OP(O)(propoxy)₂ | Br | —CH₂C(=O)-p-phenylene-OC(=O)Buᵗ | |
| 1052 | —OP(O)(propoxy)₂ | Br | —CH₂C(=O)-p-phenylene-OC(=O)Prⁱ | |
| 1053 | —OP(O)(propoxy)₂ | Br | —CH₂C(=O)-o-phenylene-OC(=O)Ph | |
| 1054 | —OP(O)(propoxy)₂ | I | —CH₂O(C=O)Buᵗ | |
| 1055 | —OP(O)(propoxy)₂ | Br | 4-(propionyloxy)benzyl | |
| 1056 | —OP(O)(propoxy)₂ | Br | 2-(ethoxycarbonyloxy)benzyl | |
| 1057 | —OP(O)(propoxy)₂ | Br | —CH₂C(=O)-m-phenylene-OC(=O)Ph | |
| 1058 | —OP(O)(propoxy)₂ | Br | 4-(CF₃O-benzoyl)methyl | |

TABLE 4-continued

| Cmp | R⁹ | Q | R | m.p./° C. |
|---|---|---|---|---|
| 1059 | —OP(O)(propoxy)₂ | Br | (2,5-dichloro-4-(benzoyloxy)phenyl)-C(=O)CH₂— | |
| 1060 | —OP(O)(isopropoxy)₂ | Br | —CH₂C(=O)-p-phenylene-OC(=O)Ph | |
| 1061 | —OP(O)(isopropoxy)₂ | I | —CH₂OC(=O)Ph | |
| 1062 | —OP(O)(isopropoxy)₂ | Br | —CH₂C(=O)-p-phenylene-OC(=O)Buᵗ | |
| 1063 | —OP(O)(isopropoxy)₂ | Br | —CH₂C(=O)-p-phenylene-OC(=O)Prⁱ | |
| 1064 | —OP(O)(isopropoxy)₂ | Br | —CH₂C(=O)-o-phenylene-OC(=O)Ph | |
| 1065 | —OP(O)(isopropoxy)₂ | I | —CH₂O(C=O)Buᵗ | |
| 1066 | —OP(O)(isopropoxy)₂ | Br | 4-(propionyloxy)benzyl | |
| 1067 | —OP(O)(isopropoxy)₂ | Br | 2-(ethoxycarbonyloxy)benzyl | |
| 1068 | —OP(O)(isopropoxy)₂ | Br | —CH₂C(=O)-m-phenylene-OC(=O)Ph | |
| 1069 | —OP(O)(isopropoxy)₂ | Br | 4-(CF₃O-benzoyl)methyl | |
| 1070 | —OP(O)(isopropoxy)₂ | Br | (2,5-dichloro-4-(benzoyloxy)phenyl)-C(=O)CH₂— | |
| 1071 | —OP(O)(butoxy)₂ | Br | —CH₂C(=O)-p-phenylene-OC(=O)Ph | |
| 1072 | —OP(O)(butoxy)₂ | I | —CH₂OC(=O)Ph | |
| 1073 | —OP(O)(butoxy)₂ | Br | —CH₂C(=O)-p-phenylene-OC(=O)Buᵗ | |
| 1074 | —OP(O)(butoxy)₂ | Br | —CH₂C(=O)-p-phenylene-OC(=O)Prⁱ | |
| 1075 | —OP(O)(butoxy)₂ | Br | —CH₂C(=O)-o-phenylene-OC(=O)Ph | |
| 1076 | —OP(O)(butoxy)₂ | I | —CH₂O(C=O)Buᵗ | |
| 1077 | —OP(O)(butoxy)₂ | Br | 4-(propionyloxy)benzyl | |
| 1078 | —OP(O)(butoxy)₂ | Br | 2-(ethoxycarbonyloxy)benzyl | |
| 1079 | —OP(O)(butoxy)₂ | Br | —CH₂C(=O)-m-phenylene-OC(=O)Ph | |
| 1080 | —OP(O)(butoxy)₂ | Br | 4-(CF₃O-benzoyl)methyl | |

TABLE 4-continued

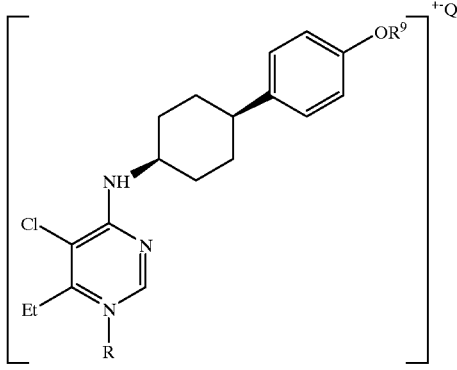

| Cmp | R⁹ | Q | R | m.p./° C. |
|---|---|---|---|---|
| 1081 | —OP(O)(butoxy)₂ | Br | 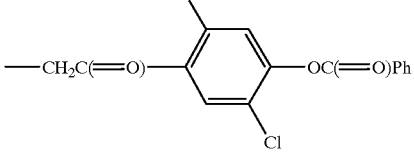 | |
| 1082 | —OP(O)(pentoxy)₂ | Br | —CH₂C(=O)-p-phenylene-OC(=O)Ph | |
| 1083 | —OP(O)(pentoxy)₂ | I | —CH₂OC(=O)Ph | |
| 1084 | —OP(O)(pentoxy)₂ | Br | —CH₂C(=O)-p-phenylene-OC(=O)Buᵗ | |
| 1085 | —OP(O)(pentoxy)₂ | Br | —CH₂C(=O)-p-phenylene-OC(=O)Prⁱ | |
| 1086 | —OP(O)(pentoxy)₂ | Br | —CH₂C(=O)-o-phenylene-OC(=O)Ph | |
| 1087 | —OP(O)(pentoxy)₂ | I | —CH₂O(C=O)Buᵗ | |
| 1088 | —OP(O)(pentoxy)₂ | Br | 4-(propionyloxy)benzyl | |
| 1089 | —OP(O)(pentoxy)₂ | Br | 2-(ethoxycarbonyloxy)benzyl | |
| 1090 | —OP(O)(pentoxy)₂ | Br | —CH₂C(=O)-m-phenylene-OC(=O)Ph | |
| 1091 | —OP(O)(pentoxy)₂ | Br | 4-(CF₃O-benzoyl)methyl | |
| 1092 | —OP(O)(pentoxy)₂ | Br | 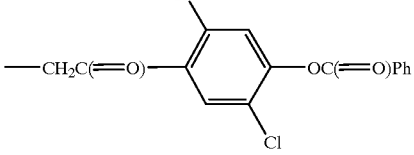 | |
| 1093 | —OP(O)(phenoxy)₂ | Br | —CH₂C(=O)-p-phenylene-OC(=O)Ph | |
| 1094 | —OP(O)(phenoxy)₂ | I | —CH₂OC(=O)Ph | |
| 1095 | —OP(O)(phenoxy)₂ | Br | —CH₂C(=O)-p-phenylene-OC(=O)Buᵗ | |
| 1096 | —OP(O)(phenoxy)₂ | Br | —CH₂C(=O)-p-phenylene-OC(=O)Prⁱ | |
| 1097 | —OP(O)(phenoxy)₂ | Br | —CH₂C(=O)-o-phenylene-OC(=O)Ph | |
| 1098 | —OP(O)(phenoxy)₂ | I | —CH₂O(C=O)Buᵗ | |
| 1099 | —OP(O)(phenoxy)₂ | Br | 4-(propionyloxy)benzyl | |
| 1100 | —OP(O)(phenoxy)₂ | Br | 2-(ethoxycarbonyloxy)benzyl | |
| 1101 | —OP(O)(phenoxy)₂ | Br | —CH₂C(=O)-m-phenylene-OC(=O)Ph | |
| 1102 | —OP(O)(phenoxy)₂ | Br | 4-(CF₃O-benzoyl)methyl | |

TABLE 4-continued

| Cmp | R⁹ | Q | R | m.p./° C. |
|---|---|---|---|---|
| 1103 | —OP(O)(phenoxy)₂ | Br | [structure: —CH₂C(=O)- attached to 2,5-dichloro-phenylene-OC(=O)Ph] | |
| 1104 | —OP(O)(4-Cl-phenoxy)₂ | Br | —CH₂C(=O)-p-phenylene-OC(=O)Ph | |
| 1105 | —OP(O)(4-Cl-phenoxy)₂ | I | —CH₂OC(=O)Ph | |
| 1106 | —OP(O)(4-Cl-phenoxy)₂ | Br | —CH₂C(=O)-p-phenylene-OC(=O)Buᵗ | |
| 1107 | —OP(O)(4-Cl-phenoxy)₂ | Br | —CH₂C(=O)-p-phenylene-OC(=O)Prⁱ | |
| 1108 | —OP(O)(4-Cl-phenoxy)₂ | Br | —CH₂C(=O)-o-phenylene-OC(=O)Ph | |
| 1109 | —OP(O)(4-Cl-phenoxy)₂ | I | —CH₂O(C=O)Buᵗ | |
| 1110 | —OP(O)(4-Cl-phenoxy)₂ | Br | 4-(propionyloxy)benzyl | |
| 1111 | —OP(O)(4-Cl-phenoxy)₂ | Br | 2-(ethoxycarbonyloxy)benzyl | |
| 1112 | —OP(O)(4-Cl-phenoxy)₂ | Br | —CH₂C(=O)-m-phenylene-OC(=O)Ph | |
| 1113 | —OP(O)(4-Cl-phenoxy)₂ | Br | 4-(CF₃O-benzoyl)methyl | |
| 1114 | —OP(O)(4-Cl-phenoxy)₂ | Br | [structure: —CH₂C(=O)- attached to 2,5-dichloro-phenylene-OC(=O)Ph] | |
| 1115 | —OP(O)(4-toloxy)₂ | Br | —CH₂C(=O)-p-phenylene-OC(=O)Ph | |
| 1116 | —OP(O)(4-toloxy)₂ | I | —CH₂OC(=O)Ph | |
| 1117 | —OP(O)(4-toloxy)₂ | Br | —CH₂C(=O)-p-phenylene-OC(=O)Buᵗ | |
| 1118 | —OP(O)(4-toloxy)₂ | Br | —CH₂C(=O)-p-phenylene-OC(=O)Prⁱ | |
| 1119 | —OP(O)(4-toloxy)₂ | Br | —CH₂C(=O)-o-phenylene-OC(=O)Ph | |
| 1120 | —OP(O)(4-toloxy)₂ | I | —CH₂O(C=O)Buᵗ | |
| 1121 | —OP(O)(4-toloxy)₂ | Br | 4-(propionyloxy)benzyl | |
| 1122 | —OP(O)(4-toloxy)₂ | Br | 2-(ethoxycarbonyloxy)benzyl | |
| 1123 | —OP(O)(4-toloxy)₂ | Br | —CH₂C(=O)-m-phenylene-OC(=O)Ph | |
| 1124 | —OP(O)(4-toloxy)₂ | Br | 4-(CF₃O-benzoyl)methyl | |

TABLE 4-continued

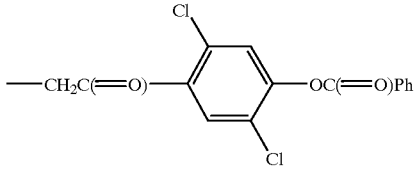

| Cmp | R⁹ | Q | R | m.p./° C. |
|---|---|---|---|---|
| 1125 | —OP(O)(4-toloxy)₂ | Br | —CH₂C(=O)-(2,5-dichloro-4-(OC(=O)Ph)phenyl) | |
| 1126 | —OP(O)(NMe₂)₂ | Br | —CH₂C(=O)-p-phenylene-OC(=O)Ph | |
| 1127 | —OP(O)(NMe₂)₂ | I  | —CH₂OC(=O)Ph | |
| 1128 | —OP(O)(NMe₂)₂ | Br | —CH₂C(=O)-p-phenylene-OC(=O)Buᵗ | |
| 1129 | —OP(O)(NMe₂)₂ | Br | —CH₂C(=O)-p-phenylene-OC(=O)Prⁱ | |
| 1130 | —OP(O)(NMe₂)₂ | Br | —CH₂C(=O)-o-phenylene-OC(=O)Ph | |
| 1131 | —OP(O)(NMe₂)₂ | I  | —CH₂O(C=O)Buᵗ | |
| 1132 | —OP(O)(NMe₂)₂ | Br | 4-(propionyloxy)benzyl | |
| 1133 | —OP(O)(NMe₂)₂ | Br | 2-(ethoxycarbonyloxy)benzyl | |
| 1134 | —OP(O)(NMe₂)₂ | Br | —CH₂C(=O)-m-phenylene-OC(=O)Ph | |
| 1135 | —OP(O)(NMe₂)₂ | Br | 4-(CF₃O-benzoyl)methyl | |
| 1136 | —OP(O)(NMe₂)₂ | Br | —CH₂C(=O)-(2,5-dichloro-4-(OC(=O)Ph)phenyl) | |
| 1137 | —OP(O)(NEt₂)₂ | Br | —CH₂C(=O)-p-phenylene-OC(=O)Ph | |
| 1138 | —OP(O)(NEt₂)₂ | I  | —CH₂OC(=O)Ph | |
| 1139 | —OP(O)(NEt₂)₂ | Br | —CH₂C(=O)-p-phenylene-OC(=O)Buᵗ | |
| 1140 | —OP(O)(NEt₂)₂ | Br | —CH₂C(=O)-p-phenylene-OC(=O)Prⁱ | |
| 1141 | —OP(O)(NEt₂)₂ | Br | —CH₂C(=O)-o-phenylene-OC(=O)Ph | |
| 1142 | —OP(O)(NEt₂)₂ | I  | —CH₂O(C=O)Buᵗ | |
| 1143 | —OP(O)(NEt₂)₂ | Br | 4-(propionyloxy)benzyl | |
| 1144 | —OP(O)(NEt₂)₂ | Br | 2-(ethoxycarbonyloxy)benzyl | |
| 1145 | —OP(O)(NEt₂)₂ | Br | —CH₂C(=O)-m-phenylene-OC(=O)Ph | |
| 1146 | —OP(O)(NEt₂)₂ | Br | 4-(CF₃O-benzoyl)methyl | |

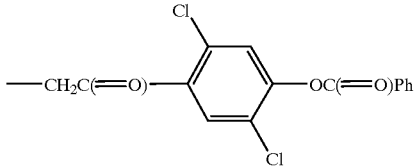

TABLE 4-continued

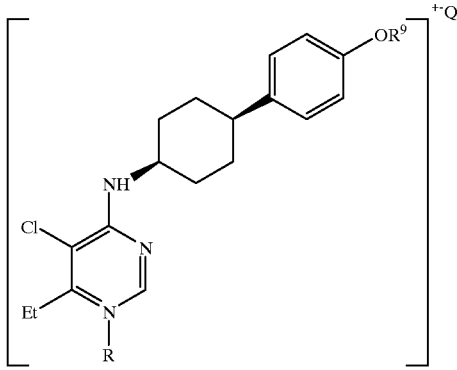

| Cmp | R⁹ | Q | R | m.p./° C. |
|---|---|---|---|---|
| 1147 | —OP(O)(NEt₂)₂ | Br | 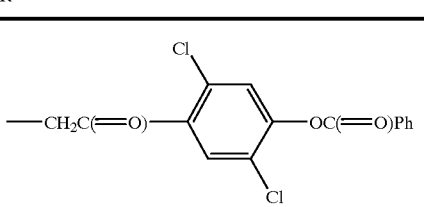 | |
| 1148 | —OP(O)(NPrⁱ₂)₂ | Br | —CH₂C(=O)-p-phenylene-OC(=O)Ph | |
| 1149 | —OP(O)(NPrⁱ₂)₂ | I | —CH₂OC(=O)Ph | |
| 1150 | —OP(O)(NPrⁱ₂)₂ | Br | —CH₂C(=O)-p-phenylene-OC(=O)Buᵗ | |
| 1151 | —OP(O)(NPrⁱ₂)₂ | Br | —CH₂C(=O)-p-phenylene-OC(=O)Prⁱ | |
| 1152 | —OP(O)(NPrⁱ₂)₂ | Br | —CH₂C(=O)-o-phenylene-OC(=O)Ph | |
| 1153 | —OP(O)(NPrⁱ₂)₂ | I | —CH₂O(C=O)Buᵗ | |
| 1154 | —OP(O)(NPrⁱ₂)₂ | Br | 4-(propionyloxy)benzyl | |
| 1155 | —OP(O)(NPrⁱ₂)₂ | Br | 2-(ethoxycarbonyloxy)benzyl | |
| 1156 | —OP(O)(NPrⁱ₂)₂ | Br | —CH₂C(=O)-m-phenylene-OC(=O)Ph | |
| 1157 | —OP(O)(NPrⁱ₂)₂ | Br | 4-(CF₃O-benzoyl)methyl | |
| 1158 | —OP(O)(NPrⁱ₂)₂ | Br | 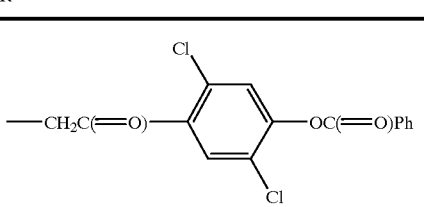 | |
| 1159 | —OP(O)(NHPh)₂ | Br | —CH₂C(=O)-p-phenylene-OC(=O)Ph | |
| 1160 | —OP(O)(NHPh)₂ | I | —CH₂OC(=O)Ph | |
| 1161 | —OP(O)(NHPh)₂ | Br | —CH₂C(=O)-p-phenylene-OC(=O)Buᵗ | |
| 1162 | —OP(O)(NHPh)₂ | Br | —CH₂C(=O)-p-phenylene-OC(=O)Prⁱ | |
| 1163 | —OP(O)(NHPh)₂ | Br | —CH₂C(=O)-o-phenylene-OC(=O)Ph | |
| 1164 | —OP(O)(NHPh)₂ | I | —CH₂O(C=O)Buᵗ | |
| 1165 | —OP(O)(NHPh)₂ | Br | 4-(propionyloxy)benzyl | |
| 1166 | —OP(O)(NHPh)₂ | Br | 2-(ethoxycarbonyloxy)benzyl | |
| 1167 | —OP(O)(NHPh)₂ | Br | —CH₂C(=O)-m-phenylene-OC(=O)Ph | |
| 1168 | —OP(O)(NHPh)₂ | Br | 4-(CF₃O-benzoyl)methyl | |

TABLE 4-continued

| Cmp | R⁹ | Q | R | m.p./° C. |
|---|---|---|---|---|
| 1169 | —OP(O)(NHPh)₂ | Br | —CH₂C(=O)-(2,5-dichloro-4-(OC(=O)Ph)phenyl) | |
| 1170 | —OP(O)(NHPh)(OPh) | Br | —CH₂C(=O)-p-phenylene-OC(=O)Ph | |
| 1171 | —OP(O)(NHPh)(OPh) | I | —CH₂OC(=O)Ph | |
| 1172 | —OP(O)(NHPh)(OPh) | Br | —CH₂C(=O)-p-phenylene-OC(=O)Buᵗ | |
| 1173 | —OP(O)(NHPh)(OPh) | Br | —CH₂C(=O)-p-phenylene-OC(=O)Prⁱ | |
| 1174 | —OP(O)(NHPh)(OPh) | Br | —CH₂C(=O)-o-phenylene-OC(=O)Ph | |
| 1175 | —OP(O)(NHPh)(OPh) | I | —CH₂O(C=O)Buᵗ | |
| 1176 | —OP(O)(NHPh)(OPh) | Br | 4-(propionyloxy)benzyl | |
| 1177 | —OP(O)(NHPh)(OPh) | Br | 2-(ethoxycarbonyloxy)benzyl | |
| 1178 | —OP(O)(NHPh)(OPh) | Br | —CH₂C(=O)-m-phenylene-OC(=O)Ph | |
| 1179 | —OP(O)(NHPh)(OPh) | Br | 4-(CF₃O-benzoyl)methyl | |
| 1180 | —OP(O)(NHPh)(OPh) | Br | —CH₂C(=O)-(2,5-dichloro-4-(OC(=O)Ph)phenyl) | |
| 1181 | —OP(S)Me₂ | Br | —CH₂C(=O)-p-phenylene-OC(=O)Ph | |
| 1182 | —OP(S)Me₂ | I | —CH₂OC(=O)Ph | |
| 1183 | —OP(S)Me₂ | Br | —CH₂C(=O)-p-phenylene-OC(=O)Buᵗ | |
| 1184 | —OP(S)Me₂ | Br | —CH₂C(=O)-p-phenylene-OC(=O)Prⁱ | |
| 1185 | —OP(S)Me₂ | Br | —CH₂C(=O)-o-phenylene-OC(=O)Ph | |
| 1186 | —OP(S)Me₂ | I | —CH₂O(C=O)Buᵗ | |
| 1187 | —OP(S)Me₂ | Br | 4-(propionyloxy)benzyl | |
| 1188 | —OP(S)Me₂ | Br | 2-(ethoxycarbonyloxy)benzyl | |
| 1189 | —OP(S)Me₂ | Br | —CH₂C(=O)-m-phenylene-OC(=O)Ph | |
| 1190 | —OP(S)Me₂ | Br | 4-(CF₃O-benzoyl)methyl | |

TABLE 4-continued

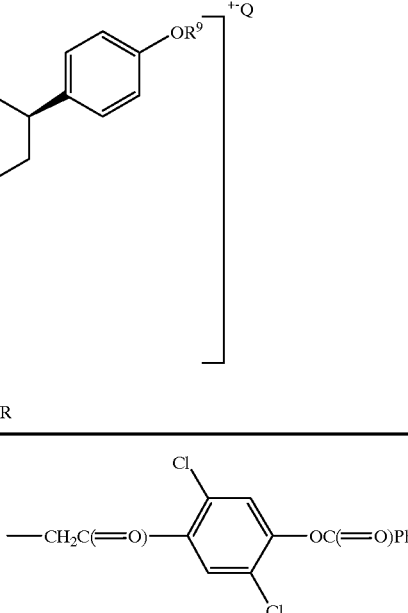

| Cmp | R⁹ | Q | R | m.p./° C. |
|---|---|---|---|---|
| 1191 | —OP(S)Me₂ | Br | 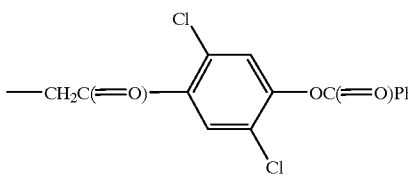 | |
| 1192 | —OP(S)Et₂ | Br | —CH₂C(=O)-p-phenylene-OC(=O)Ph | |
| 1193 | —OP(S)Et₂ | I | —CH₂OC(=O)Ph | |
| 1194 | —OP(S)Et₂ | Br | —CH₂C(=O)-p-phenylene-OC(=O)Buᵗ | |
| 1195 | —OP(S)Et₂ | Br | —CH₂C(=O)-p-phenylene-OC(=O)Prⁱ | |
| 1196 | —OP(S)Et₂ | Br | —CH₂C(=O)-o-phenylene-OC(=O)Ph | |
| 1197 | —OP(S)Et₂ | I | —CH₂O(C=O)Buᵗ | |
| 1198 | —OP(S)Et₂ | Br | 4-(propionyloxy)benzyl | |
| 1199 | —OP(S)Et₂ | Br | 2-(ethoxycarbonyloxy)benzyl | |
| 1200 | —OP(S)Et₂ | Br | —CH₂C(=O)-m-phenylene-OC(=O)Ph | |
| 1201 | —OP(S)Et₂ | Br | 4-(CF₃O-benzoyl)methyl | |
| 1202 | —OP(S)Et₂ | Br | —CH₂C(=O)—[2,5-dichloro-phenylene]—OC(=O)Ph | |
| 1203 | —OP(S)Ph₂ | Br | —CH₂C(=O)-p-phenylene-OC(=O)Ph | |
| 1204 | —OP(S)Ph₂ | I | —CH₂OC(=O)Ph | |
| 1205 | —OP(S)Ph₂ | Br | —CH₂C(=O)-p-phenylene-OC(=O)Buᵗ | |
| 1206 | —OP(S)Ph₂ | Br | —CH₂C(=O)-p-phenylene-OC(=O)Prⁱ | |
| 1207 | —OP(S)Ph₂ | Br | —CH₂C(=O)-o-phenylene-OC(=O)Ph | |
| 1208 | —OP(S)Ph₂ | I | —CH₂O(C=O)Buᵗ | |
| 1209 | —OP(S)Ph₂ | Br | 4-(propionyloxy)benzyl | |
| 1210 | —OP(S)Ph₂ | Br | 2-(ethoxycarbonyloxy)benzyl | |
| 1211 | —OP(S)Ph₂ | Br | —CH₂C(=O)-m-phenylene-OC(=O)Ph | |
| 1212 | —OP(S)Ph₂ | Br | 4-(CF₃O-benzoyl)methyl | |

TABLE 4-continued

| Cmp | R⁹ | Q | R | m.p./° C. |
|---|---|---|---|---|
| 1213 | —OP(S)Ph₂ | Br | —CH₂C(=O)-(2,5-dichloro-4-(OC(=O)Ph)phenyl) | |
| 1214 | —OP(S)(Me)Ph | Br | —CH₂C(=O)-p-phenylene-OC(=O)Ph | |
| 1215 | —OP(S)(Me)Ph | I | —CH₂OC(=O)Ph | |
| 1216 | —OP(S)(Me)Ph | Br | —CH₂C(=O)-p-phenylene-OC(=O)Buᵗ | |
| 1217 | —OP(S)(Me)Ph | Br | —CH₂C(=O)-p-phenylene-OC(=O)Prⁱ | |
| 1218 | —OP(S)(Me)Ph | Br | —CH₂C(=O)-o-phenylene-OC(=O)Ph | |
| 1219 | —OP(S)(Me)Ph | I | —CH₂O(C=O)Buᵗ | |
| 1220 | —OP(S)(Me)Ph | Br | 4-(propionyloxy)benzyl | |
| 1221 | —OP(S)(Me)Ph | Br | 2-(ethoxycarbonyloxy)benzyl | |
| 1222 | —OP(S)(Me)Ph | Br | —CH₂C(=O)-m-phenylene-OC(=O)Ph | |
| 1223 | —OP(S)(Me)Ph | Br | 4-(CF₃O-benzoyl)methyl | |
| 1224 | —OP(S)(Me)Ph | Br | —CH₂C(=O)-(2,5-dichloro-4-(OC(=O)Ph)phenyl) | |
| 1225 | —OP(S)(OMe)₂ | Br | —CH₂C(=O)-p-phenylene-OC=O)Ph | |
| 1226 | —OP(S)(OMe)₂ | I | —CH₂OC(=O)Ph | |
| 1227 | —OP(S)(OMe)₂ | Br | —CH₂C(=O)-p-phenylene-OC(=O)Buᵗ | |
| 1228 | —OP(S)(OMe)₂ | Br | —CH₂C(=O)-p-phenylene-OC(=O)Prⁱ | |
| 1229 | —OP(S)(OMe)₂ | Br | —CH₂C(=O)-o-phenylene-OC(=O)Ph | |
| 1230 | —OP(S)(OMe)₂ | I | —CH₂O(C=O)Buᵗ | |
| 1231 | —OP(S)(OMe)₂ | Br | 4-(propionyloxy)benzyl | |
| 1232 | —OP(S)(OMe)₂ | Br | 2-(ethoxycarbonyloxy)benzyl | |
| 1233 | —OP(S)(OMe)₂ | Br | —CH₂C(=O)-m-phenylene-OC(=O)Ph | |
| 1234 | —OP(S)(OMe)₂ | Br | 4-(CF₃O-benzoyl)methyl | |

TABLE 4-continued

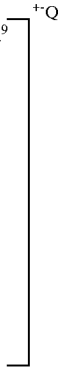

| Cmp | R⁹ | Q | R | m.p./° C. |
|---|---|---|---|---|
| 1235 | —OP(S)(OMe)₂ | Br | 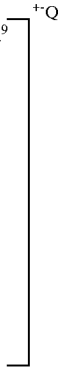 | |
| 1236 | —OP(S)(OEt)₂ | Br | —CH₂C(=O)-p-phenylene-OC(=O)Ph | |
| 1237 | —OP(S)(OEt)₂ | I | —CH₂OC(=O)Ph | |
| 1238 | —OP(S)(OEt)₂ | Br | —CH₂C(=O)-p-phenylene-OC(=O)Buᵗ | |
| 1239 | —OP(S)(OEt)₂ | Br | —CH₂C(=O)-p-phenylene-OC(=O)Prⁱ | |
| 1240 | —OP(S)(OEt)₂ | Br | —CH₂C(=O)-o-phenylene-OC(=O)Ph | |
| 1241 | —OP(S)(OEt)₂ | I | —CH₂O(C=O)Buᵗ | |
| 1242 | —OP(S)(OEt)₂ | Br | 4-(propionyloxy)benzyl | |
| 1243 | —OP(S)(OEt)₂ | Br | 2-(ethoxycarbonyloxy)benzyl | |
| 1244 | —OP(S)(OEt)₂ | Br | —CH₂C(=O)-m-phenylene-OC(=O)Ph | |
| 1245 | —OP(S)(OEt)₂ | Br | 4-(CF₃O-benzoyl)methyl | |
| 1246 | —OP(S)(OEt)₂ | Br | 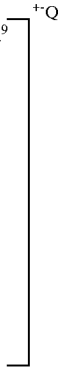 | |
| 1247 | —OP(S)(OPr)₂ | Br | —CH₂C(=O)-p-phenylene-OC(=O)Ph | |
| 1248 | —OP(S)(OPr)₂ | I | —CH₂OC(=O)Ph | |
| 1249 | —OP(S)(OPr)₂ | Br | —CH₂C(=O)-p-phenylene-OC(=O)Buᵗ | |
| 1250 | —OP(S)(OPr)₂ | Br | —CH₂C(=O)-p-phenylene-OC(=O)Prⁱ | |
| 1251 | —OP(S)(OPr)₂ | Br | —CH₂C(=O)-o-phenylene-OC(=O)Ph | |
| 1252 | —OP(S)(OPr)₂ | I | —CH₂O(C=O)Buᵗ | |
| 1253 | —OP(S)(OPr)₂ | Br | 4-(propionyloxy)benzyl | |
| 1254 | —OP(S)(OPr)₂ | Br | 2-(ethoxycarbonyloxy)benzyl | |
| 1255 | —OP(S)(OPr)₂ | Br | —CH₂C(=O)-m-phenylene-OC(=O)Ph | |
| 1256 | —OP(S)(OPr)₂ | Br | 4-(CF₃O-benzoyl)methyl | |

TABLE 4-continued

[Structure: pyrimidine with Cl, Et, N-R substituents; NH-cyclohexyl-phenyl-OR⁹ group; +Q counterion]

| Cmp | R⁹ | Q | R | m.p./° C. |
|---|---|---|---|---|
| 1257 | —OP(S)(OPr)₂ | Br | —CH₂C(=O)-[2,5-dichloro-4-(OC(=O)Ph)phenyl] | |
| 1258 | —OP(S)(OBu)₂ | Br | —CH₂C(=O)-p-phenylene-OC(=O)Ph | |
| 1259 | —OP(S)(OBu)₂ | I | —CH₂OC(=O)Ph | |
| 1260 | —OP(S)(OBu)₂ | Br | —CH₂C(=O)-p-phenylene-OC(=O)Bu$^t$ | |
| 1261 | —OP(S)(OBu)₂ | Br | —CH₂C(=O)-p-phenylene-OC(=O)Pr$^i$ | |
| 1262 | —OP(S)(OBu)₂ | Br | —CH₂C(=O)-o-phenylene-OC(=O)Ph | |
| 1263 | —OP(S)(OBu)₂ | I | —CH₂O(C=O)Bu$^t$ | |
| 1264 | —OP(S)(OBu)₂ | Br | 4-(propionyloxy)benzyl | |
| 1265 | —OP(S)(OBu)₂ | Br | 2-(ethoxycarbonyloxy)benzyl | |
| 1266 | —OP(S)(OBu)₂ | Br | —CH₂C(=O)-m-phenylene-OC(=O)Ph | |
| 1267 | —OP(S)(OBu)₂ | Br | 4-(CF₃O-benzoyl)methyl | |
| 1268 | —OP(S)(OBu)₂ | Br | —CH₂C(=O)-[2,5-dichloro-4-(OC(=O)Ph)phenyl] | |
| 1269 | —OP(S)(NMe₂)₂ | Br | —CH₂C(=O)-p-phenylene-OC(=O)Ph | |
| 1270 | —OP(S)(NMe₂)₂ | I | —CH₂OC(=O)Ph | |
| 1271 | —OP(S)(NMe₂)₂ | Br | —CH₂C(=O)-p-phenylene-OC(=O)Bu$^t$ | |
| 1272 | —OP(S)(NMe₂)₂ | Br | —CH₂C(=O)-p-phenylene-OC(=O)Pr$^i$ | |
| 1273 | —OP(S)(NMe₂)₂ | Br | —CH₂C(=O)-o-phenylene-OC(=O)Ph | |
| 1274 | —OP(S)(NMe₂)₂ | I | —CH₂O(C=O)Bu$^t$ | |

TABLE 4-continued
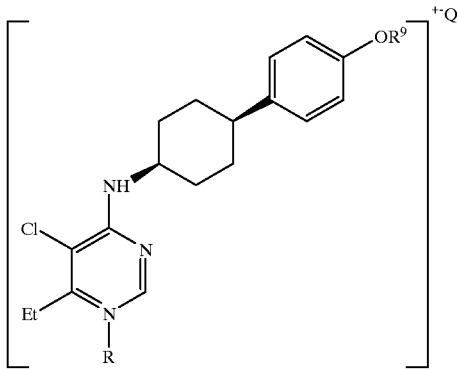
| Cmp | R⁹ | Q | R | m.p./° C. |
|---|---|---|---|---|
| 1275 | —OP(S)(NMe₂)₂ | Br | 4-(propionyloxy)benzyl | |
| 1276 | —OP(S)(NMe₂)₂ | Br | 2-(ethoxycarbonyloxy)benzyl | |
| 1277 | —OP(S)(NMe₂)₂ | Br | —CH₂C(=O)-m-phenylene-OC(=O)Ph | |
| 1278 | —OP(S)(NMe₂)₂ | Br | 4-(CF₃O-benzoyl)methyl | |
| 1279 | —OP(S)(NMe₂)₂ | Br | —CH₂C(=O)-(2,5-dichloro-4-(phenylcarbonyloxy)phenyl)— | |
TABLE 5
| Cmp | R⁹ | position | m.p./° C. |
|---|---|---|---|
| 2000 | —OSO₂Me | 2 | |
| 2001 | —OSO₂CF₃ | 2 | |
| 2002 | —OSO₂CF₃ | 3 | |
| 2003 | —OSO₂Me | 3 | |

TABLE 6

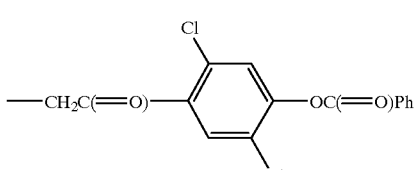

| Cmp | R⁹ | position | Q | R | m.p./° C. |
|---|---|---|---|---|---|
| 3000 | —OSO₂Me | 2 | Br | —CH₂C(=O)-p-phenylene-OC(=O)Ph | |
| 3001 | —OSO₂Me | 3 | Br | —CH₂C(=O)-p-phenylene-OC(=O)Ph | |
| 3002 | —OSO₂CF₃ | 2 | Br | —CH₂C(=O)-p-phenylene-OC(=O)Ph | |
| 3003 | —OSO₂CF₃ | 3 | Br | —CH₂C(=O)-p-phenylene-OC(=O)Ph | |
| 3004 | —OSO₂Me | 2 | I | —CH₂OC(=O)Ph | |
| 3005 | —OSO₂Me | 3 | I | —CH₂OC(=O)Ph | |
| 3006 | —OSO₂CF₃ | 2 | I | —CH₂OC(=O)Ph | |
| 3007 | —OSO₂CF₃ | 3 | I | —CH₂OC(=O)Ph | |
| 3008 | —OSO₂Me | 2 | Br | —CH₂C(=O)-o-phenylene-OC(=O)Ph | |
| 3009 | —OSO₂Me | 3 | Br | —CH₂C(=O)-o-phenylene-OC(=O)Ph | |
| 3010 | —OSO₂CF₃ | 2 | Br | —CH₂C(=O)-o-phenylene-OC(=O)Ph | |
| 3011 | —OSO₂CF₃ | 3 | Br | —CH₂C(=O)-o-phenylene-OC(=O)Ph | |
| 3012 | —OSO₂Me | 2 | Br | 4-CF₃O-phenacyl | |
| 3013 | —OSO₂Me | 3 | Br | 4-CF₃O-phenacyl | |
| 3014 | —OSO₂CF₃ | 2 | Br | 4-CF₃O-phenacyl | |
| 3015 | —OSO₂CF₃ | 3 | Br | 4-CF₃O-phenacyl | |
| 3016 | —OSO₂Me | 2 | Br | 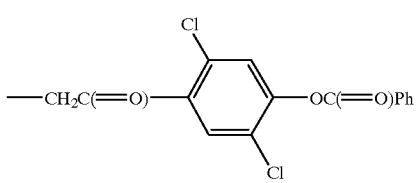 | |
| 3017 | —OSO₂Me | 3 | Br | | |
| 3018 | —OSO₂CF₃ | 2 | Br | 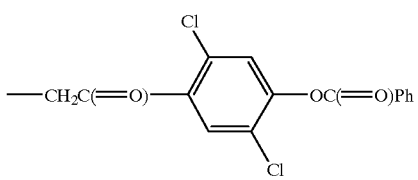 | |

TABLE 6-continued

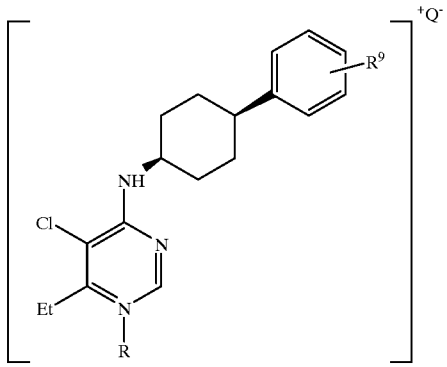

| Cmp | R⁹ | position | Q | R | m.p./° C. |
|---|---|---|---|---|---|
| 3019 | —OSO₂CF₃ | 3 | Br | 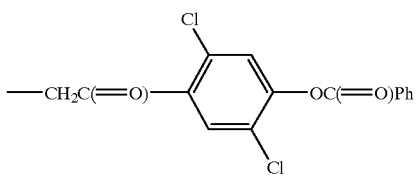 | |
| 3020 | —OSO₂Me | 2 | Br | 2-(ethoxycarbonyloxy)benzyl | |
| 3021 | —OSO₂Me | 3 | Br | 2-(ethoxycarbonyloxy)benzyl | |
| 3022 | —OSO₂CF₃ | 2 | Br | 2-(ethoxycarbonyloxy)benzyl | |
| 3023 | —OSO₂CF₃ | 3 | Br | 2-(ethoxycarbonyloxy)benzyl | |

C. BIOLOGICAL EXAMPLES

Use as Insecticide/Acaricide

Example 1

Cut stems of bean plants (*Phaseolus vulgaris*) carrying one leaf are transferred into brown bottles filled with tap water and subsequently populated with approximately 100 spider mites (*Tetranychus urticae*). The plant leaf and the spider mites are sprayed to run-off point with an aqueous solution or dispersion of the formulated preparation to be examined. After run off, plants and mites are stored in a controlled environment chamber (16 hours of light/day, 25° C., 40–60% relative humidity). After 6 days storage, the effect of the preparation on all stages of the spider mites is determined. At a concentration of 300 ppm (based on the content of active compound), compounds 1–3 12, 13, 17, 18, 21, 24–27, 29–37, 43, 44, 47, 48, 49, 50, 52, 91–98, 100–114, 116–139, 142, 144–149, 151–154, 156–161, 163–165, 169, 171, 174, 176, 178, 179, 18, 182, 184, 187, 191–197, 501 and 502 cause a mortality of 90–100%.

In a similar test, using a full population of spider mites on the leaves, compounds 4–6 and 9–11 cause a mortality of 90–100%.

Example 2

Germinated field bean seeds (*Vicia fabae*) with radicles are transferred into brown bottles filled with tap water and subsequently populated with approximately 100 black bean aphids (*Aphis fabae*). Plants and aphids are sprayed to run-off point with an aqueous dispersion or solution of the formulated preparation to be examined. After the solution has run off, plants and animals are stored in a controlled environment chamber (16 hours of light/day, 25° C., 40–60% relative humidity). After 3 days storage, the effect of the preparation on the aphids is determined. At a concentration of 300 ppm (based on the content of active compound), compounds 2, 17, 18, 19, 21, 26–32, 34–36, 46, 48, 49, 97, 105, 113, 132, 134, 135, 137, 139, 144–147, 151–154, 158–161, 182, 184, 186–188, 191, 192, 500 and 501 cause a 90–100% mortality of the aphids.

In a similar test, using a heavy infestation of aphids, after 3 days compounds 4, 6–8, 10 and 11 cause a mortality of 90–100%.

Example 3

The leaves of 12 rice plants having a stem length of 8 cm are dipped for 5 seconds into an aqueous solution or dispersion of the formulated preparation to be examined. After the solution has run off, the rice plants treated in this manner are placed in a Petri dish and populated with about 20 larvae (L3 stage) of the rice leafhopper species (*Nilaparvata lugens*). The Petri dish is sealed and then stored in a controlled environment chamber (16 hours of light/day, 25° C., 40–60% relative humidity). After 6 days storage, the mortality of the leafhopper larvae is determined. At a concentration of 300 ppm (based on the content of active compound), compounds 2, 3, 13, 17, 25–27, 29, 30, 33–36, 42, 46, 49, 50, 93, 97–99, 102–107, 110, 113, 126, 132–134, 136, 137, 139, 144–149, 151, 153, 182, 184, 185, 187, 188, 197 and 500–502 cause a mortality of 90–100%.

In a similar test, using only 10 larvae, maintained in a growing receptacle at 21° C., after 4 days compounds 6, 8 and 10 cause a mortality of 90–100%.

Example 4

A Petri dish whose bottom is covered with filter paper and which contains about 5 ml of culture medium is prepared.

Pieces of filter paper with about 30, 24-hour-old eggs of the tobacco budworm (*Heliothis virescens*) are dipped into an aqueous solution or dispersion of the formulated preparation to be examined for about 5 seconds and subsequently placed into the Petri dish. A further 200 μl of the aqueous solution are spread over the culture medium. The Petri dish is sealed and then kept at about 25° C., in a controlled environment chamber. After 6 days storage, the effect of the preparation on the eggs and the larvae which may have hatched from these is determined. At a concentration of 300 ppm (based on the content of active compound), compounds 2, 3, 13, 17, 26, 28–31, 46, 145–146 197, and 500–502 cause a mortality of 90–100%.

Example 5

A Petri dish whose bottom is covered with filter paper and which contains about 5 ml of culture medium is prepared. Ten L2 larvae of the Egyptian cotton leaf worm (*Spodoptera littoralis*) are counted into a small beaker. 200 μl of an aqueous solution or dispersion of the formulated preparation to be examined are pipetted into the beaker. The treated larvae are then poured into the Petri dish and a further 200 μl of the aqueous solution are spread over the culture medium. The Petri dish is sealed and then stored at about 25° C. in a controlled environment chamber. After 6 days storage, the effect of the preparation on the larvae is determined. At a concentration of 300 ppm (based on the content of active compound), compounds 2, 3, 13, 17, 29–31, 42, 93, 104, 132, 133 and 145 cause a mortality of 90–100%.

In a similar test, using 10 L4 larvae, maintained at c. 23° C., after 4 days, compound 6 causes a mortality of 90–100%.

Example 6

A Petri dish, half of whose bottom is covered with filter paper and contains a germinated maize corn on a moist cotton pad, is prepared. About 50, 4–5-day-old eggs of the southern corn rootworm (*Diabrotica undecimpunctata*) are transferred onto the filter paper. Three drops of 200 μl of an aqueous solution or dispersion of the formulated preparation to be examined are pipetted onto the eggs, and the rest is pipetted onto the maize corn. The Petri dish is sealed and then stored at about 25° C. in a controlled environment chamber chamber. After 6 days storage, the effect of the preparation on the eggs and the larvae which may have hatched from these is determined. At a concentration of 300 ppm (based on the content of active compound), compounds 2, 3, 17, 29, 31, 126, 132, 133, 135–137, 145 and 502 cause a mortality of 90–100%.

In a similar test, using 10 L2 larvae, maintained in a growing receptacle at 26° C., after 2 days, compound 6, 8 10 and 11 cause a mortality of 90–100%.

Example 7

Part A of the test (contact activity): Approximately 5000 recently hatched, active (mobile) larvae (2nd development stage) of the root gall nematode (*Meloidogyne incognita*) are placed into a glass vessel containing an aqueous solution or dispersion of the formulated preparation to be examined (final volume 20 ml). After the nematode larvae have been continually exposed for 6 days, the percentage of the specimen which has ceased to move (been immobilised) owing to the effect of the preparation is determined by comparison with the untreated controls (percent nematicidal contact activity).

Part B of the test (soil-drench activity): For this test, the entire solution or dispersion from part A of the test (active compound and pre-treated nematode larvae) is poured into a pot filled with 60 ml of soil in which three 9-day-old cucumber plants (*Cucumis sativus*) have been planted. This drench application reduces the active compound content, based on the volume of the soil, to one third of the active compound content in part A of the test. After two weeks in a greenhouse at about 26° C. (the plants being watered twice a day), the root balls of the cucumber plants are carefully washed out from the soil mixture infested with nematodes. The number of root galls per plant is counted and compared with the infestation of untreated control plants. The reduction of infestation in percent as activity criterion is calculated using Abbott's formula (percent nematicidal soil-drench activity).

At a concentration of 3 ppm in part A of the test and 1 ppm in part B of the test, respectively, (based in each case on the content of active compound), compounds 2, 3, 17, 30, 31, 46, 117, 126, 132, 133, 135, 143, 144, 146, 500 and 502 have a 90–100% activity against the root gall nematode *Meloidogyne incognita*. In addition, compounds 3, 30, 46, 500 and 502 are active in the part A test.

Fungicide Tests

Compounds are assessed for activity against one or more of the following:

*Plasmopara viticola*: vine downy mildew

*Erysiphe graminis f.* sp. tritici: wheat powdery mildew

*Pyricularia oryzae*: rice blast

*Leptosphaeria nodorum*: glume blotch

*Pellicularia sasakii*: rice sheath blight

*Phytophthora infestans*: late tomato or potato blight

Aqueous solutions or dispersions of the compounds at the desired concentration, including a wetting agent, were applied by spray or by drenching the stem base of the test plants, as appropriate. Plants or plant parts were then inoculated with appropriate test pathogens and kept under controlled environment conditions suitable for maintaining plant growth and development of the disease. After an appropriate time, the degree of infection of the affected part of the plant was visually estimated. Compounds are assessed on a score of 1 to 3 where 1 is little or no control, 2 is moderate control and 3 is good to total control. At a concentration of 500 ppm (w/v) or less, the following compounds scored 2 or more against the fungi specified

*Plasmopara viticola*

17, 18, 23, 31, 32

*Erysiphe graminis f.* sp. tritici 17, 18, 30, 31, 500, 501

*Pyricularia oryzae*

5, 21, 28, 30, 32

*Leptosphaeria nodorum*

3, 17, 18

*Pellicularia sasakii*

17

*Phytophthora infestans*

3, 23, 28, 30, 31, 32

What is claimed is:
1. A compound of formula I, N-oxides or salts

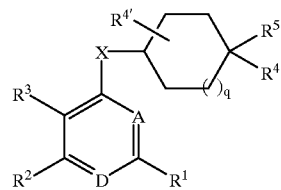 (I)

in which
q is 0, 1 or 2
$R^1$ is hydrogen, halogen, $(C_1-C_8)$-alkyl, $(C_1-C_8)$-haloalkyl, $(C_1-C_8)$-alkoxy or $(C_3-C_6)$-cycloalkyl;
$R^2$ and $R^3$ are identical or different and are each hydrogen, $(C_1-C_8)$-alkyl, $(C_2-C_8)$-alkenyl, $(C_2-C_8)$-alkynyl, $(C_1-C_8)$-alkoxy, halogen, hydroxy, cyano, nitro, thiocyanato, $(C_1-C_8)$-alkoxycarbonyl, $(C_1-C_8)$-alkylthio, $(C_1-C_8)$-alkylsulfinyl, $(C_1-C_8)$-alkylsulfonyl, amino, $(C_1-C_8)$-alkylamino, $(C_1-C_8)$-dialkylamino or $(C_3-C_6)$-cycloalkyl, and in which in the alkyl, cycloalkyl, alkenyl, alkynyl, alkoxy, alkynyl, alkanoyl, alkoxycarbonyl, alkylthio, alkylsulfinyl, alkylsulfonyl, alkylamino or dialkylamino, groups, a saturated carbon unit can be replaced by oxygen, $S(O)_x$, where x=0, 1 or 2 or by dimethylsilyl and further in these groups up to 3 hydrogen atoms can be replaced by halogen and in the case of fluorine also all hydrogen atoms can be replaced by fluorine; or
$R^2$ and $R^3$ together with the carbon atoms to which they are attached form an unsaturated 5- or 6-membered carbocyclic ring which may, if it is a 5-membered ring, contain an oxygen or sulfur atom instead of $CH_2$, or which may, if it is a 6-membered ring, contain one or two nitrogen atoms instead of one or two CH units, and which may be substituted by 1, 2 or 3 identical or different radicals, these radicals being $(C_1-C_4)$-alkyl, $(C_1-C_4)$-haloalkyl, halogen, $(C_1-C_4)$-alkoxy or $(C_1-C_4)$-haloalkoxy; or
$R^2$ and $R^3$ together with the carbon atoms to which they are attached form a saturated 5-, 6- or 7-membered carbocyclic ring which may contain oxygen and/or sulfur instead of one or two $CH_2$ groups and which may be substituted by 1, 2 or 3 $(C_1-C_4)$-alkyl groups;
A is CH and D is $N^+R \times 1/n \ Q^{n-}$ or
A is N and D is $N^+R \times 1/n \ Q^{n-}$ or
A is CH or N and D is N or
A is $N^+R \times 1/n \ Q^{n-}$ and D is N,
R is $CR^6R^7D^aR^8$,
$Q^{n-}$ is an inorganic or organic anion, n being 1, 2, 3 or 4;
X is NH, O or $S(O)_q$, (q is 0, 1 or 2);
$R^4$ and $R^{4'}$, which may be the same or different, are hydrogen, halogen, $(C_1-C_4)$-alkyl, $(C_1-C_4)$-halogenalkyl, $(C_1-C_4)$-alkoxy or $(C_1-C_4)$-alkylthio;
$R^5$ is the group

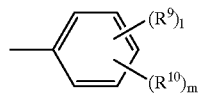

l is 1, 2, 3, 4 or 5;
m is 0, 1, 2, 3 or 4, each $R^9$, which may be the same or different from any other $R^9$, is $(C_2-C_8)$-haloalkenyloxy, $(C_2-C_8)$-haloalkynyl, $(C_2-C_8)$-haloalkynyloxy, $(C_1-C_4)$-haloalkoxy-$(C_1-C_4)$-haloalkoxy, oxiran-2-ylmethoxy, oxetan-2-ylmethoxy, isopropylidenoamino-oxy, isopropylidenamino-oxy-$(C_1-C_4)$-alkoxy, formyl, $—SF_5$, hydroxy or heterocyclyloxy, in which the last named group may be substituted by up to three of the same or different $D^1R^{12}$, cyano, nitro or halogen, or
$R^9$ is a group $Z—R^{11}$, in which
Z is $OSO_2$, $NR^{13}SO_2$, $UC(=W)V$, $U^1P(W^1)(V^1R^{11})V^2$, $SO_2NR^{13}$, $SO_2O$, $NR^{13}SO_2NR^{13}$, $OSO_2NR^{13}$, $NR^{13}SO_2O$, $Si(OR)^{13}R^{13}$, $N(O)R^{13}$, $NR^{13}O$, $NR^{13}NR^{13}$, $N=N$, $N=$, $NR^{13}—N=$, $D^1—N=$ and
$U^1$ is a direct bond, oxygen, $NR^{13}$ or sulfur,
U is oxygen, $NR^{13}$ or sulfur, or when W or V is $NR^{13}$ or sulfur, it can also be a direct bond,
W is oxygen, $NR^{130}$ or sulfur, and
$R^{130}$ is hydrogen, nitro, cyano, optionally substituted alkyl, optionally substituted acyloxy, optionally substituted aryl, optionally substituted heteroaryl, hydroxy, optionally substituted alkoxy, optionally substituted aryloxy, optionally substituted heteroaryloxy, mono- or disubstituted amino;
$W^1$ is oxygen or sulfur,
V, $V^1$, $V^2$, independently of each other are a direct bond, $NR^{13}$, oxygen or sulfur,
each $R^{13}$, which may be the same or different from any other $R^{13}$, is hydroxy, alkyl, optionally substituted alkoxy, optionally substituted aryloxy, optionally substituted aryl, optionally substituted heteroaryl, optionally substituted heteroaryloxy, mono- or disubstituted amino, optionally substituted acyl or optionally substituted acyloxy,
$R^{11}$ is $(C_1-C_{20})$-alkyl, $(C_2-C_{20})$-alkenyl, $(C_2-C_{20})$-alkynyl, $(C_3-C_8)$-cycloalkyl or $(C_4-C_8)$-cycloalkenyl, in which groups optionally one or more, generally up to three, $CH_2$-groups can be replaced by carbonyl-, thiocarbonyl or O, S, SO, $SO_2$, $NR^{13}$ or $SiR^{16}R^{17}$, and these groups may be substituted by up to three of the same or different $D^2R^{14}$, cyano, nitro or halogen, or
$R^{11}$ is hydrogen, aryl or heterocyclyl, in which the last named group may be substituted by up to three of the same or different $D^3R^{15}$, cyano, nitro or halogen, or when V is $NR^{13}$, $R^{13}$ and $R^{11}$ can together form a 4- to 8-membered ring, in which one or two $CH_2$-groups, is replaced by oxygen; $S(O)_t$, where t=0, 1 or 2, or $NR^{19}$, in which
$D^1$, $D^2$ and $D^3$, independently of each other, are a direct bond, oxygen, $S(O)_k$, $SO_2O$, $OSO_2$, CO, OCO, COO, $NR^{13'}$, $SO_2—NR^{13'}$, $NR^{13'}SO_2$, $ONR^{13'}$, $NR^{13'}O$, $NR^{13'}CO$, $CONR^{13'}$ or $SiR^{16}R^{17}$, and k=0, 1 or 2 and $R^{13'}$ has the same meaning as $R^{13}$,
$R^{16}$, $R^{17}$, independently of each other, are $(C_1-C_4)$-alkyl;
$R^{12}$, $R^{14}$ and $R^{15}$ are hydrogen, $C_1-C_8$-alkyl, $C_2-C_8$-alkenyl, $C_2-C_8$-alkynyl, $C_3-C_8$-cycloalkyl, $C_4-C_8$-cycloalkenyl, $C_3-C_8$-cycloalkyl-$C_1-C_4$-alkyl, $C_4-C_8$-cycloalkenyl-$C_1-C_4$-alkyl, aryl, heterocyclyl, aryl-$C_1-C_4$-alkyl or heterocyclyl-$C_1-C_4$-alkyl, in which in any alkyl-, alkenyl- and alkynyl based groups optionally one or more, $CH_2$-group can be replaced by hetero atom units O or S, the alkyl, alkenyl- and alkynyl groups, with or without the named varations, can also be optionally substituted by one or more of the same or different groups selected from halogen, hydroxy and cyano and in the case of the last named 8 groups, the cycloaliphatic, aromatic or heterocyclic rings are unsubstituted or substituted by one or more of the same or different substituents $R^{18}$;
$R^{18}$ is $(C_1-C_4)$-alkyl, $(C_1-C_4)$-haloalkyl, $(C_1-C_4)$-alkoxy, $(C_1-C_4)$-haloalkoxy, cyano, nitro or halogen;
$R^{19}$ is hydrogen, $(C_1-C_8)$-alkyl, $(C_1-C_4)$-haloalkyl, $(C_1-C_4)$-alkoxy, $(C_1-C_4)$-alkylthio, $(C_3-C_5)$-cycloalkyl, ($C_2$–$C_4$)-alkenyl, ($C_2$–$C_4$)-alkynyl, ($C_1$–$C_4$)-alkanoyl, ($C_2$–$C_4$)-haloalkanoyl, ($C_2$–$C_4$)-alkoxyalkyl, phenyl-($C_1$–$C_4$)-alkyl or phenyl and the phenyl groups are unsubstituted or substituted by one or more of the same or different substituents $R^{20}$, $R^{20}$ is ($C_1$–$C_4$)-alkyl, ($C_1$–$C_4$)-haloalkyl, ($C_1$–$C_4$)-alkoxy, ($C_1$–$C_4$)-alkylthio, halogen or cyano;

$R^{10}$ is cyano, nitro, halogen, $C_1$–$C_8$-alkyl, $C_2$–$C_8$-alkenyl, $C_2$–$C_8$-alkynyl, $C_3$–$C_8$-cycloalkyl, $C_4$–$C_8$-cycloalkenyl, $C_3$–$C_8$-cycloalkyl-$C_1$–$C_4$-alkyl, $C_4$–$C_8$-cycloalkenyl-$C_1$–$C_4$-alkyl, aryl, heterocyclyl, aryl-$C_1$–$C_4$-alkyl or heterocyclyl-$C_1$–$C_4$-alkyl in which in any alkyl-, alkenyl- and alkynyl based groups optionally one or more, $CH_2$- group can be replaced by hetero atom units O or S, the alkyl, alkenyl- and alkynyl groups, with or without the named varations, can also be optionally substituted by one or more of the same or different groups selected from halogen, hydroxy and cyano and in the case of of the last named 8 groups, the cycloaliphatic, aromatic or heterocyclic rings are unsubstituted or substituted by one or more of the same or different substituents $R^{21}$, $R^{21}$ has the same meaning as $R^{18}$, or two adjacent $R^9$ and/or $R^{10}$ groups together with the carbon atoms two which they are attached can form an unsaturated 5- or 6-membered carbocyclic ring, which in a 5 membered ring, a $CH_2$ can be replaced by an oxygen- or sulfur atom and in a 6 membered ring, one or two CH units can be replaced by one or two nitrogen atoms or substituted by 1, 2 or 3 of the same or different groups selected from ($C_1$–$C_4$)-alkyl, ($C_1$–$C_4$)-haloalkyl, halogen, ($C_1$–$C_4$)-alkoxy or ($C_1$–$C_4$)-haloalkoxy; or two adjacent $R^9$ and/or $R^{10}$ groups together with the carbon atoms to which they are attached can form a saturated 5- or 6- or 7 membered carbocyclic ring, in which, one or two $CH_2$ units can be replaced by one or two oxygen and/or sulfur and can be substituted by 1, 2 or 3 ($C_1$–$C_4$)-alkyl groups, and further when A is CH and D is $N^+R \times 1/n$ $Q^{n-}$ or A is N and D is $N^+R \times 1/n$ Q or A is $N^+R \times 1/n$ $Q^{n-}$ and D is N $R^9$ can also be ($C_2$–$C_6$)-alkynyl, ($C_2$–$C_6$)-alkynyloxy or ($C_2$–$C_6$)-haloalkenyl;

$R^6$ is hydrogen, halogen or $C_1$–$C_4$-alkyl or a negative charge, which can represent $Q^{n-}$ $R^7$ is hydrogen, halogen, CN, nitro, ($C_1$–$C_4$)-alkoxycarbonyl, ($C_1$–$C_4$)-alkylcarbamoyl, di-($C_1$–$C_4$)-alkylcarbamoyl, ($C_1$–$C_8$)-alkoxy, ($C_1$–$C_8$)-alkyl, ($C_2$–$C_8$)-alkenyl, ($C_2$–$C_8$)-alkynyl, aryl or ($C_3$–$C_8$)-cycloalkyl.

$D^a$ is a direct bond, $NR^{70}$, $N(O)R^{70}$, O, S, SO, $SO_2$, $C(=W^a)$, $OC(=W^a)$, $U^a(C=W^a)V^a$ where $U^a$ and $V^a$ are a direct bond, $NR^{70}$, S or O, except $V^a$ is not a bond when $U^a$ is bond or O; $SiR^{72}R^{73}$, $U^b(P=W^b)V^bV^c$, $U^b(SO_2)U^c$ where one of $U^b$ and $U^c$ is a direct bond, $NR^{70}$, S or O and the other is $NR^{70}$; $U^a(CW^a)(CW^a)V^b$, $NR^{70}$O, O $NR^{70}$, $NR^{70}$ $NR^{70}$, N=N, —N=, —$NR^{70}$— N= or —O—N=, and $W^a$ is O, S or $NR^{71}$; $W^b$ is O or S;

$U^a$, $V^b$ and $V^c$, independently of each other are a direct bond, $NR^{70}$, S or O each $R^{70}$, which may be the same or different from any other $R^{70}$, is hydrogen, hydroxy, optionally substituted alkyl, optionally substituted alkoxy, optionally substituted aryloxy, optionally substituted aryl, optionally substituted heteroaryl, optionally substituted heteroaryloxy, mono- or disubstituted amino, optionally substituted acyloxy, and may also form a 4 to 8 membered with $R^6$, $R^{112}$ OR $R^{113}$, respectively with the $D^a$, $D^{12}$ OR $D^{13}$ to which they are attached; each $R^{71}$, which may be the same or different from any other $R^{71}$, is hydrogen, nitro, cyano, hydroxy, optionally substituted alkyl, optionally substituted alkoxy, optionally substituted aryloxy, optionally substituted aryl, optionally substituted heteroaryl, optionally substituted heteroaryloxy, mono- or disubstituted amino or optionally substituted acyloxy; $R^{72}$ and $R^{73}$ are alkyl or optionally substituted aryl; and $R^8$ is hydrogen, cyano, alkyl, alkenyl, alkynyl, cycloalkyl, cycloalkenyl, aryl or heterocyclyl, in which up to three $CH_2$ units in a carbon containing group can be replaced by carbonyl-, thiocarbonyl or O, S, SO, $SO_2$, $NR^{70}$ or Si $R^{72}R^{73}$ and can also be substituted by nitro, halogen, $SF_5$ or $D^{12}R^{112}$, and in the case $D^a$ is $U^bP(=W^b)V^bV^c$, the two $R^6$ groups together with the $V^bPV^c$, to which they are attached can form a 4 to 8 membered ring, $D^{12}$ is a direct bond, $NR^{70}$, $N(O)R^{70}$, O, S, SO, $SiR^{72}R^{73}$, $U'(CW')V'$, $U^{1'}(PW^1)V^{1'}V^{2'}$, $U^{2'}(SO_2)U^{3'}$, $Si(OR^{72})R^{73}$, $Si(OR^{72})(OR^{73})$, $NR^{70}$O, $ONR^{70}$, $NR^{70}NR^{70}$, N=N, =N—, =N—NR70— =N—O—, —N=, —$NR^{70}$— N= or —O—N= and U', $U^{1'}$ V', $V^{1'}$ and $V^{2'}$, independently of each other are a direct bond, $NR^{70}$, S or O W' is O, S or $NR^{71}$;

$W^{1'}$ is O or S;

$U^{2'}$ and $U^{3'}$, independently of each other are a direct bond, $NR^{70}$ or O;

$R^{112}$ is hydrogen, cyano, alkyl, alkenyl, alkynyl, cycloalkyl, cycloalkenyl, aryl or heterocyclyl, in which up to $CH_2$ units in a carbon containing group can be replaced by carbonyl-, thiocarbonyl or O, S, SO, $SO_2$, $NR^{70}$ or $SiR^{72}R^{73}$ and can also be substituted by nitro, halogen, $SF_5$ or $D^{13}R^{113}$ and in which two adjacent $D^{12}R^{112}$ together with the carbons to which they are attached can form a condensed ring comprising 4 to 6 ring atoms which can be substituted one or more halogen or $C_1$–$C_4$-alkyl; is a negative charge for $D^{12}$=(CO)O, $(SO_2)O$, $U^{1'}(PW^{1'})$ $V^{1'}O$ which replaces the ion $Q^{n-}$; or $R^{112}$ is hydrogen when $D^{12}$ is O(CO)NH, $NR^{70}$(CO)NH, O(CS)NH, $NR^{70}$(CS)NH, (CO)NH, (CS)NH, O(CO), $NR^{70}$(CO), SO2NH;

$D^{13}$ has the same meaning as $D^{12}$ and $R^{113}$ has the same meaning as $R^{112}$.

2. A pesticidal composition comprising an effective amount of at least one compound as claimed in claim 1 together with the additives or auxiliaries which are customary for these applications.

3. A method of controlling pests, which comprises applying an effective amount of a compound as claimed in claim 1 to the pest or its locus.

* * * * *